United States Patent
Kang et al.

(10) Patent No.: US 9,935,274 B2
(45) Date of Patent: Apr. 3, 2018

(54) SUBSTITUTED 12H-INDOLO[2,3-B]QUINOXALINO[2',3':4,5] PYRROLO[3,2,1-JK]CARBAZOLES AS ORGANIC ELECTROLUMINESCENT MATERIALS

(71) Applicant: Rohm and Haas Electronic Materials Korea Ltd., Cheonan (KR)

(72) Inventors: Hee-Ryong Kang, Seoul (KR); Hyun-Ju Kang, Gwangmyeong (KR); Doo-Hyeon Moon, Hwaseong (KR); Young-Mook Lim, Cheonan (KR); Bitnari Kim, Cheonan (KR); Nam-Kyun Kim, Yongin (KR)

(73) Assignee: Rohm and Haas Electronic Materials Korea Ltd., Cheonan (KR)

( * ) Notice: Subject to any disclaimer, the term of this patent is extended or adjusted under 35 U.S.C. 154(b) by 0 days.

(21) Appl. No.: 15/324,272

(22) PCT Filed: Jul. 8, 2015

(86) PCT No.: PCT/KR2015/007059
§ 371 (c)(1),
(2) Date: Jan. 6, 2017

(87) PCT Pub. No.: WO2016/006925
PCT Pub. Date: Jan. 14, 2016

(65) Prior Publication Data
US 2017/0179406 A1    Jun. 22, 2017

(30) Foreign Application Priority Data

Jul. 9, 2014  (KR) .......... 10-2014-0086091
Jul. 6, 2015  (KR) .......... 10-2015-0096096

(51) Int. Cl.
*C07D 487/16*   (2006.01)
*H01L 51/00*    (2006.01)
*C07D 487/22*   (2006.01)
*C09K 11/02*    (2006.01)
*H01L 51/50*    (2006.01)

(52) U.S. Cl.
CPC ........ *H01L 51/0072* (2013.01); *C07D 487/22* (2013.01); *C09K 11/025* (2013.01); *H01L 51/5016* (2013.01)

(58) Field of Classification Search
CPC .................................................... C07D 487/16

USPC ........................................................ 544/338
See application file for complete search history.

(56) References Cited

U.S. PATENT DOCUMENTS

2011/0303901 A1   12/2011   Cheng et al.
2017/0125692 A1    5/2017   Kang et al.

FOREIGN PATENT DOCUMENTS

| JP | 2014073965 A | 4/2014 |
| KR | 20120087935 A | 8/2012 |
| KR | 20120095997 A | 8/2012 |
| WO | 2014104704 A1 | 7/2014 |
| WO | WO 16-006925 * | 1/2016 |
| WO | 2016036171 A1 | 3/2016 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*

* cited by examiner

*Primary Examiner* — Douglas M Willis

(57) ABSTRACT

The present invention relates to an organic compound represented by the following formula 1. The organic compound according to the present invention can produce an organic electroluminescent device having low driving voltage, excellent current and power efficiencies, and remarkably improved driving lifespan.

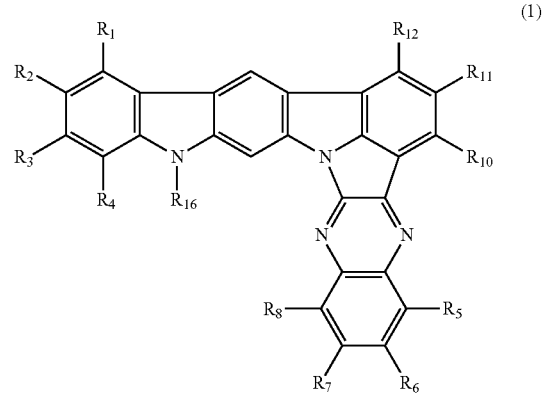

4 Claims, No Drawings

SUBSTITUTED 12H-INDOLO[2,3-B]QUINOXALINO[2',3':4,5] PYRROLO[3,2,1-JK]CARBAZOLES AS ORGANIC ELECTROLUMINESCENT MATERIALS

BACKGROUND OF THE INVENTION

Field of the Invention

The present invention relates to organic electroluminescent compounds and organic electroluminescent device comprising the same.

DESCRIPTION OF THE RELATED ART

Background Art

An electroluminescent device (EL device) is a self-light-emitting device which has advantages in that it provides a wider viewing angle, a greater contrast ratio, and a faster response time. The first organic EL device was developed by Eastman Kodak, by using small aromatic diamine molecules, and aluminum complexes as materials for forming a light-emitting layer [Appl. Phys. Lett. 51, 913, 1987].

The most important factor determining luminous efficiency in an organic EL device is light-emitting materials. Until now, fluorescent materials have been widely used as light-emitting material. However, in view of electroluminescent mechanisms, since phosphorescent materials theoretically enhance luminous efficiency by four (4) times compared to fluorescent materials, development of phosphorescent light-emitting materials is widely being researched. Iridium(III) complexes have been widely known as phosphorescent materials, including bis(2-(2'-benzothienyl)-pyridinato-N,C3')iridium(acetylacetonate) ((acac)Ir(btp)$_2$), tris(2-phenylpyridine)iridium (Ir(ppy)$_3$) and bis(4,6-difluorophenylpyridinato-N,C2)picolinate iridium (Firpic) as red, green, and blue materials, respectively.

At present, 4,4'-N,N'-dicarbazol-biphenyl (CBP) is the most widely known phosphorescent host material. Recently, Pioneer (Japan) et al. developed a high performance organic EL device using bathocuproine (BCP) and aluminum(III)bis(2-methyl-8-quinolinate)(4-phenylphenolate) (BAlq) etc., as host materials, which were known as hole blocking layer materials.

Although these materials provide good light-emitting characteristics, they have the following disadvantages: (1) Due to their low glass transition temperature and poor thermal stability, their degradation may occur during a high-temperature deposition process in a vacuum, and the lifespan of the device decreases. (2) The power efficiency of an organic EL device is given by [(π/voltage)×current efficiency], and the power efficiency is inversely proportional to the voltage. Although an organic EL device comprising phosphorescent host materials provides higher current efficiency (cd/A) than one comprising fluorescent materials, a significantly high driving voltage is necessary. Thus, there is no merit in terms of power efficiency (lm/W). (3) Further, the operational lifespan of an organic EL device is short and luminous efficiency is still required to be improved.

Meanwhile, in order to enhance its efficiency and stability, an organic EL device has a structure of a multilayer comprising a hole injection layer, a hole transport layer, a light-emitting layer, an electron transport layer, and an electron injection layer. The selection of a compound comprised in the hole transport layer is known as a method for improving the characteristics of a device such as hole transport efficiency to the light-emitting layer, luminous efficiency, lifespan, etc.

In this regard, copper phthalocyanine (CuPc), 4,4'-bis[N-(1-naphthyl)-N-phenylamino]biphenyl (NPB), N,N'-diphenyl-N,N'-bis(3-methylphenyl)-(1,1'-biphenyl)-4,4'-diamine (TPD), 4,4',4"-tris(3-methylphenylphenylamino)triphenylamine (MTDATA), etc., were used as a hole injection and transport material. However, an organic EL device using these materials is problematic in quantum efficiency and operational lifespan. It is because, when an organic EL device is driven under high current, thermal stress occurs between an anode and the hole injection layer. Thermal stress significantly reduces the operational lifespan of the device. Further, since the organic material used in the hole injection layer has very high hole mobility, the hole-electron charge balance may be broken and quantum yield (cd/A) may decrease.

Therefore, a hole transport layer for improving durability of an organic EL device still needs to be developed.

Korean Patent Appln. Laying-Open No. 2012-0087935 discloses a compound having an indolo[3,2,1-jk]carbazole backbone as an organic electroluminescent compound. Korean Patent Appln. Laying-Open No. 2012-0095997 discloses various nitrogen-containing fused heterocyclic compounds. U.S. Patent Appl. Publication No. US 2011/0303901 A1 discloses a 6H-indolo[2,3-b]quinoxaline derivative as an organic electroluminescent compound. However, the above references do not specifically disclose an organic electroluminescent compound in which two indoles are fused to a 6H-indolo[2,3-b]quinoxaline.

DISCLOSURE OF THE INVENTION

Problems to be Solved

The objective of the present invention is to provide i) an organic electroluminescent compound which can produce an organic electroluminescent device having long driving lifespan, low driving voltage, and excellent luminous efficiencies, such as current and power efficiencies, and ii) an organic electroluminescent device comprising the compound.

Solution to Problems

The present inventors found that the above objective can be achieved by an organic electroluminescent compound represented by the following formula 1 or 2:

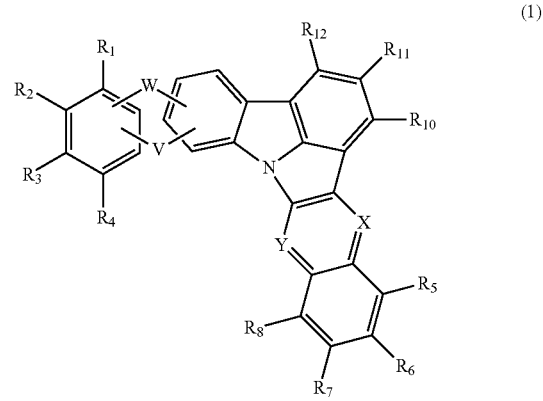

(1)

-continued

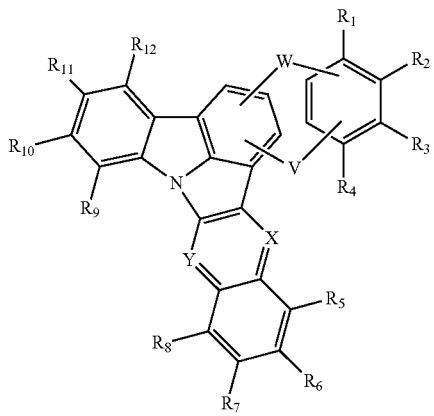

(2)

wherein

X and Y each independently represent —$CR_{13}$— or —N—, where X and Y are not simultaneously —$CR_{13}$—;

V and W each independently represent a single bond, —$CH_{14}R_{15}$—, or —$NR_{16}$—, $R_1$ to $R_{16}$ each independently represent hydrogen, deuterium, a halogen, a cyano, a substituted or unsubstituted (C1-C30)alkyl, a substituted or unsubstituted (C6-C30)aryl, a substituted or unsubstituted 3- to 30-membered heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or are linked to an adjacent substituent(s) to form a mono- or polycyclic (C3-C30) alicyclic or aromatic ring, whose carbon atom(s) may be replaced with at least one hetero atom selected from nitrogen, oxygen, and sulfur; and the heteroaryl contains at least one hetero atom selected from B, N, O, S, Si, and P.

The organic electroluminescent compound according to the present invention can manufacture an organic electroluminescent device having low driving voltage, excellent current and power efficiencies, and remarkably improved driving lifespan.

DETAILED DESCRIPTION OF THE INVENTION

Hereinafter, the present invention will be described in detail. However, the following description is intended to explain the invention, and is not meant in any way to restrict the scope of the invention.

The present invention relates to an organic electroluminescent compound of formula 1 or 2, an organic electroluminescent material comprising the compound, and an organic electroluminescent device comprising the material.

Hereinafter, the organic electroluminescent compound represented by formulae 1 and 2 will be described in detail.

Herein, "(C1-C30)alkyl" is meant to be a linear or branched alkyl having 1 to 30 carbon atoms, in which the number of carbon atoms is preferably 1 to 10, more preferably 1 to 6, and includes methyl, ethyl, n-propyl, isopropyl, n-butyl, isobutyl, tert-butyl, etc.; "(C2-C30)alkenyl" is meant to be a linear or branched alkenyl having 2 to 30 carbon atoms, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc.; "(C2-C30)alkynyl" is meant to be a linear or branched alkynyl having 2 to 30 carbon atoms, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc.; "(C3-C30)cycloalkyl" is a mono- or polycyclic hydrocarbon having 3 to 30 carbon atoms, in which the number of carbon atoms is preferably 3 to 20, more preferably 3 to 7, and includes cyclopropyl, cyclobutyl, cyclopentyl, cyclohexyl, etc.; "3- to 7-membered heterocycloalkyl" is a cycloalkyl having 3 to 7 ring backbone atoms, including at least one heteroatom selected from B, N, O, S, Si, and P, preferably O, S, and N, and includes tetrahydrofuran, pyrrolidine, thiolan, tetrahydropyran, etc.; "(C6-C30)aryl(ene)" is a monocyclic or fused ring derived from an aromatic hydrocarbon having 6 to 30 carbon atoms, in which the number of carbon atoms is preferably 6 to 20, more preferably 6 to 15, and includes phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc.; "3- to 30-membered heteroaryl(ene)" is an aryl having 3 to 30 ring backbone atoms, including at least one, preferably 1 to 4 heteroatoms selected from the group consisting of B, N, O, S, Si, and P; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. Further, "halogen" includes F, Cl, Br, and I.

Herein, "substituted" in the expression "substituted or unsubstituted" means that a hydrogen atom in a certain functional group is replaced with another atom or group, i.e. a substituent. The substituents of the substituted (C1-C30) alkyl, the substituted (C6-C30)aryl, the substituted 3- to 30-membered heteroaryl, the substituted (C3-C30)cycloalkyl, the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, and the substituted (C1-C30)alkyl (C6-C30)arylamino in $R_1$ to $R_{16}$ in formulae 1 and 2 each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 5- to 30-membered heteroaryl unsubstituted or substituted with a (C6-C30)aryl, a (C6-C30)aryl unsubstituted or substituted with a 5- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl, and preferably each independently are a (C6-C12)aryl.

In formulae 1 and 2 above, X and Y each independently represent —$CR_{13}$— or —N—, where X and Y are not simultaneously —$CR_{13}$—.

V and W each independently represent a single bond, —$CH_{14}R_{15}$—, or —$NR_{16}$—.

$R_1$ to $R_{16}$ each independently represent hydrogen, deuterium, a halogen, a cyano, a substituted or unsubstituted (C1-C30)alkyl, a substituted or unsubstituted (C6-C30)aryl, a substituted or unsubstituted 3- to 30-membered heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or are linked to an adjacent substituent(s) to form a mono- or polycyclic (C3-C30) alicyclic or aromatic ring, whose carbon atom(s) may be replaced with at least one hetero atom selected from nitrogen, oxygen, and sulfur, preferably each independently represent hydrogen, a substituted or unsubstituted (C6-C20)aryl, or a substituted or unsubstituted 5- to 20-membered heteroaryl; or are linked to an adjacent substituent(s) to form a mono- or polycyclic (C3-C20) alicyclic or aromatic ring, and more preferably each independently represent hydrogen, an unsubstituted (C6-C20)aryl, or a 5- to 20-membered heteroaryl unsubstituted or substituted with a (C6-C12)aryl; or are linked to an adjacent substituent(s) to form a mono- or polycyclic (C3-C20) aromatic ring.

According to one embodiment of the present invention, in formulae 1 and 2 above, X and Y each independently represent —$CR_{13}$— or —N—, where X and Y are not simultaneously —$CR_{13}$—; V and W each independently represent a single bond, —$CH_{14}R_{15}$—, or —$NR_{16}$—; and $R_1$ to $R_{16}$ each independently represent hydrogen, a substituted or unsubstituted (C6-C20)aryl, or a substituted or unsubstituted 5- to 20-membered heteroaryl; or are linked to an adjacent substituent(s) to form a mono- or polycyclic (C3-C20) alicyclic or aromatic ring.

According to another embodiment of the present invention, in formulae 1 and 2 above, X and Y each independently represent —$CR_{13}$— or —N—, where X and Y are not simultaneously —$CR_{13}$—; V and W each independently represent a single bond, —$CH_{14}R_{15}$—, or —$NR_{16}$—; and $R_1$ to $R_{16}$ each independently represent hydrogen, an unsubstituted (C6-C20)aryl, or a 5- to 20-membered heteroaryl unsubstituted or substituted with a (C6-C12)aryl; or are linked to an adjacent substituent(s) to form a mono- or polycyclic (C3-C20) aromatic ring.

The specific compounds of the present invention include the following compounds, but are not limited thereto:

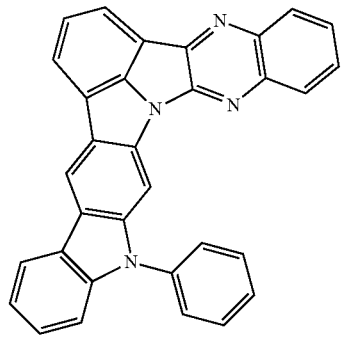

A-1

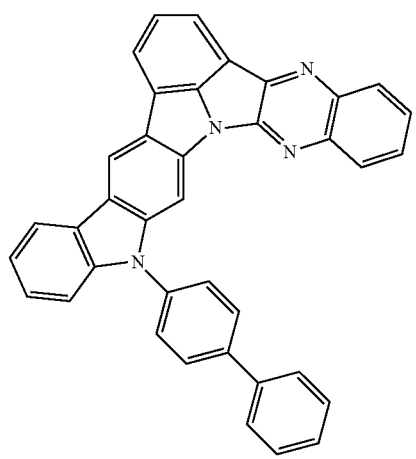

A-2

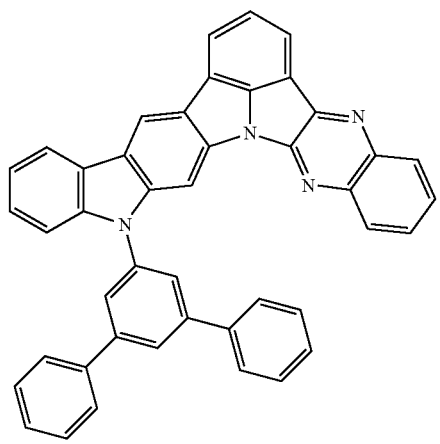

A-3

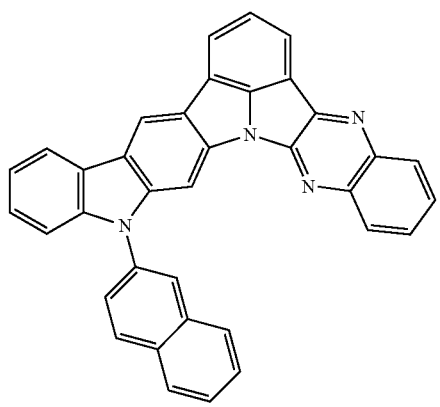

A-4

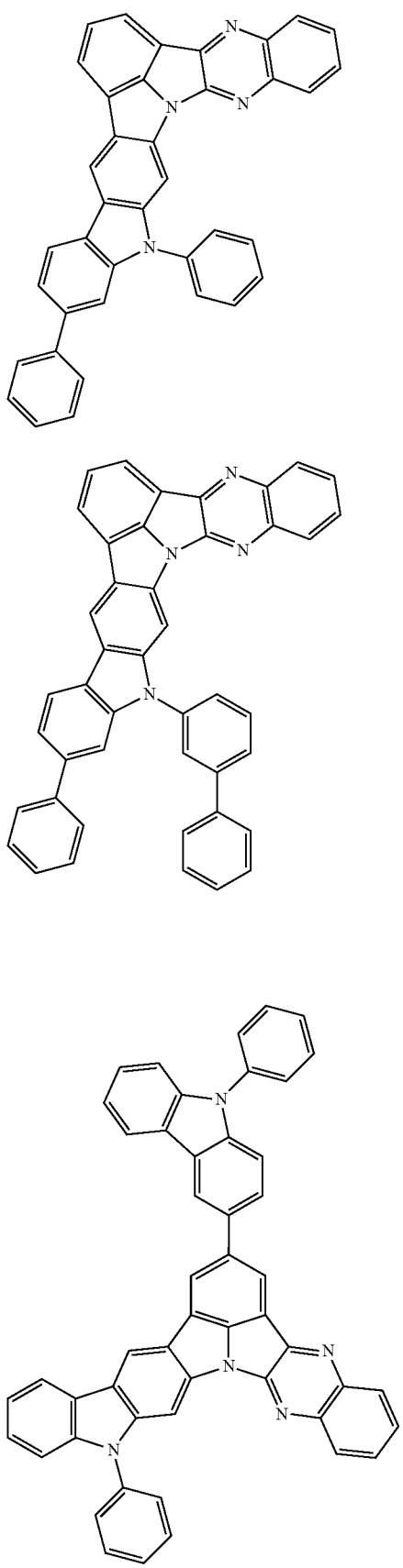
A-5
A-6
A-7
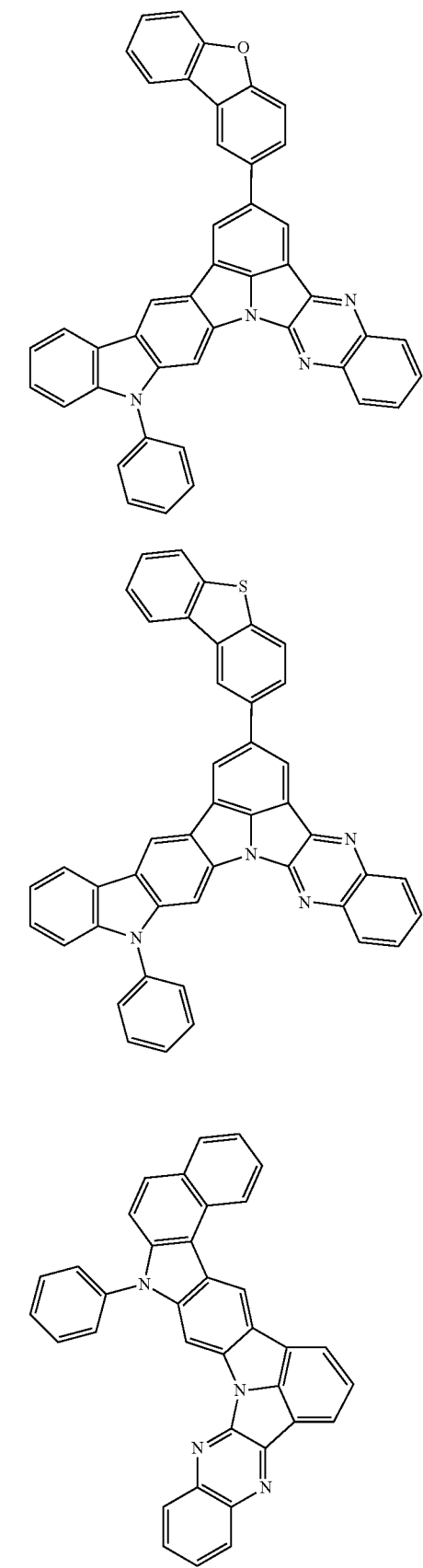
A-8
A-9
A-10

A-11
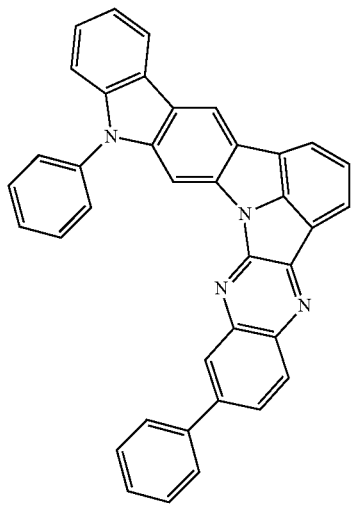
A-12
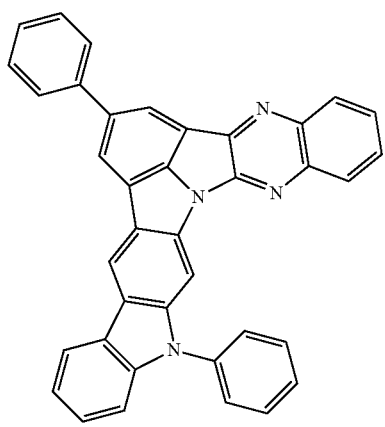
A-13
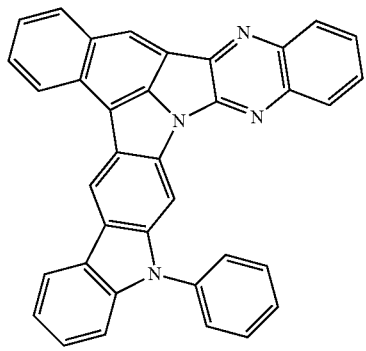
A-14
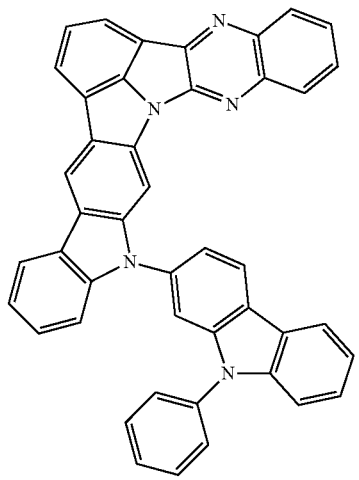
A-15
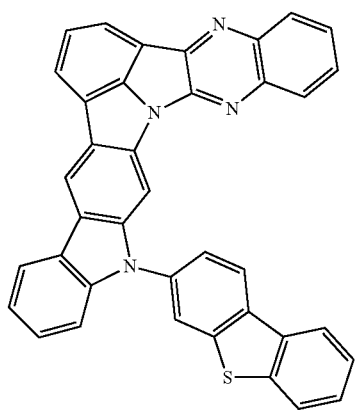
A-16
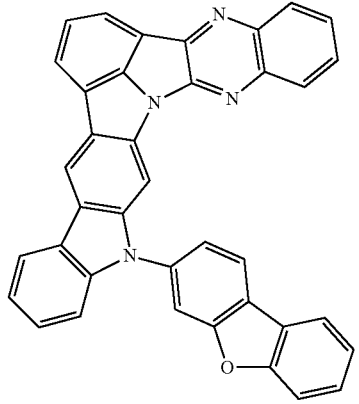

A-17
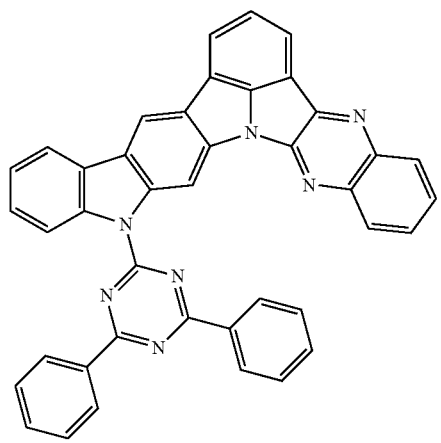
A-18
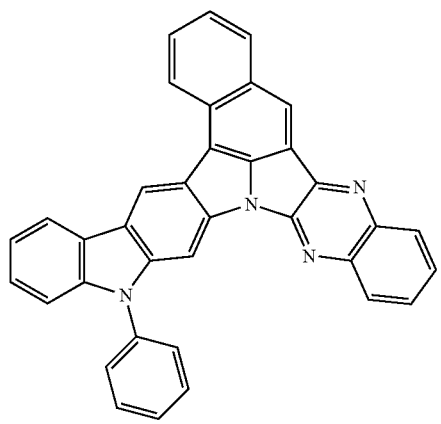
A-19
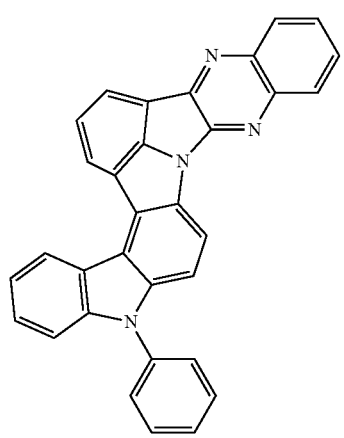
A-20
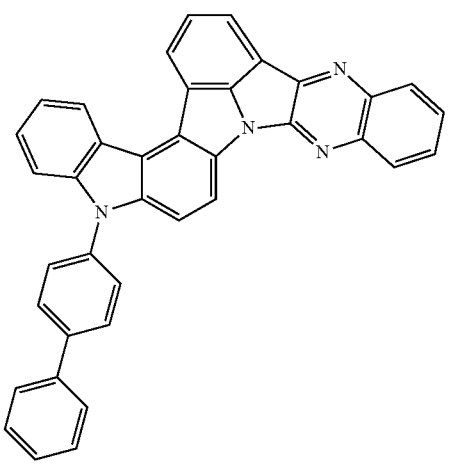
A-21
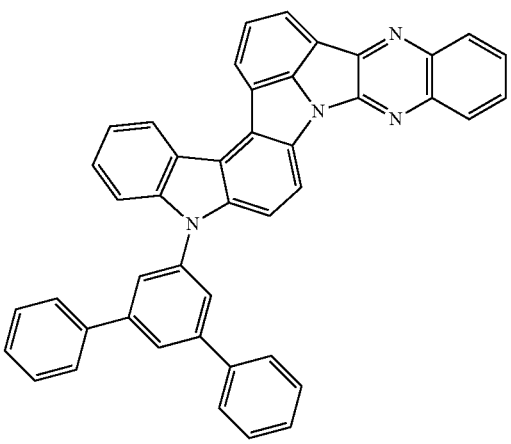
A-22
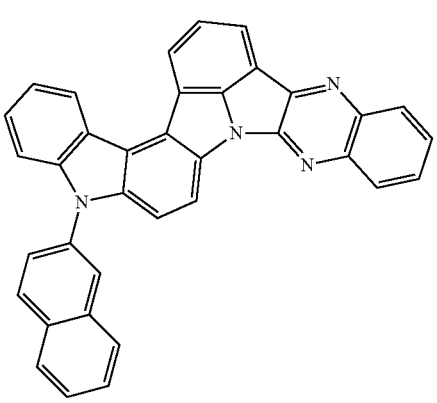

-continued
A-23
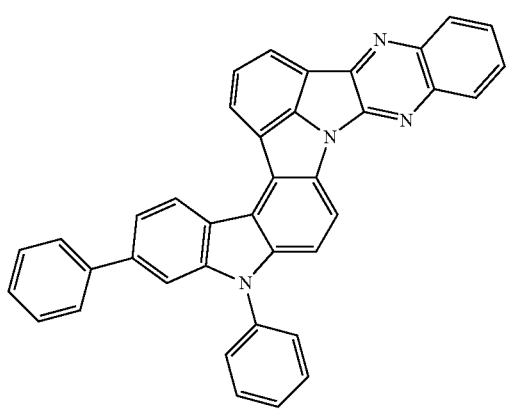
A-24
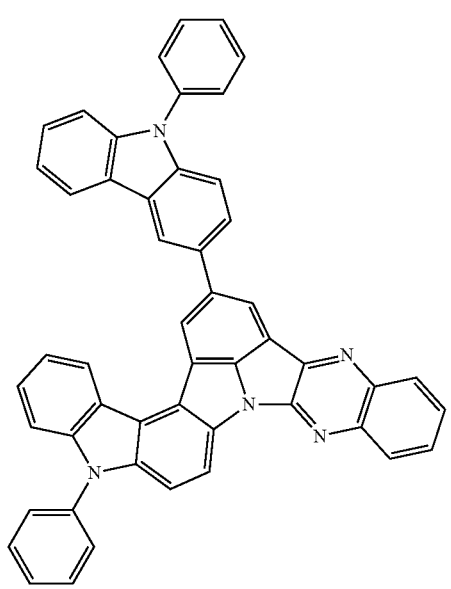
A-25
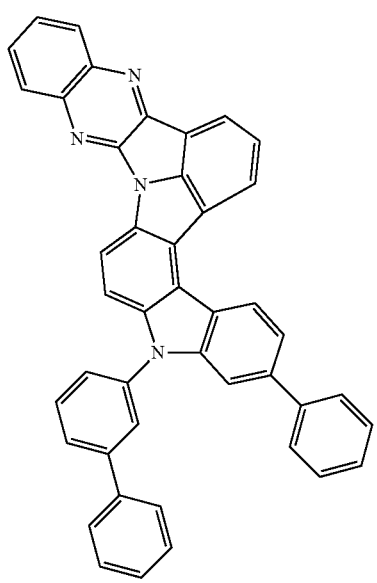
-continued
A-26
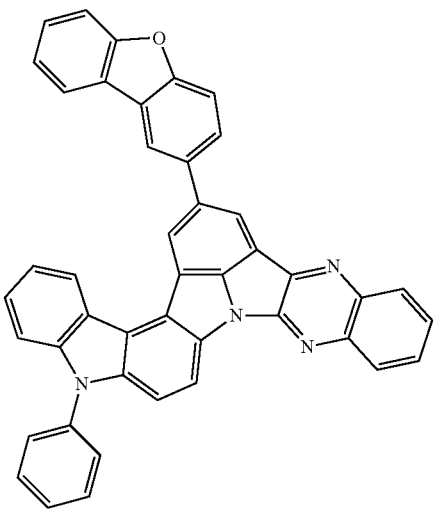
A-27
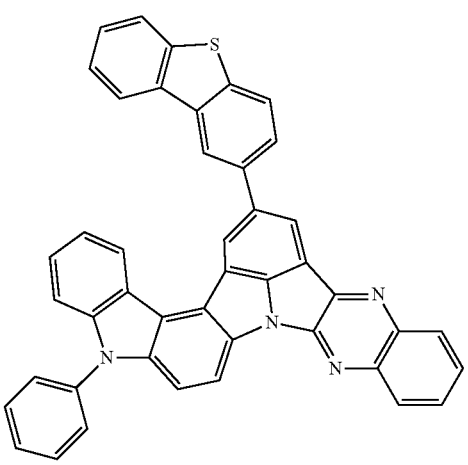
A-28
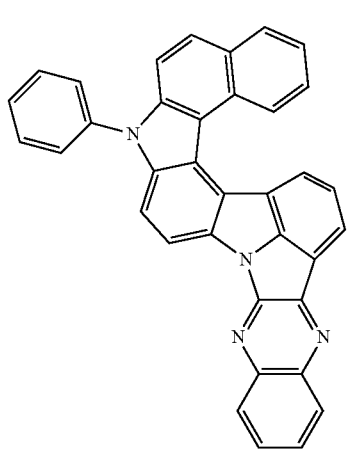

A-29
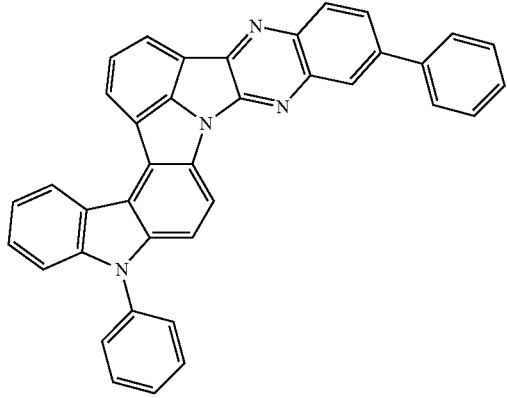
A-30
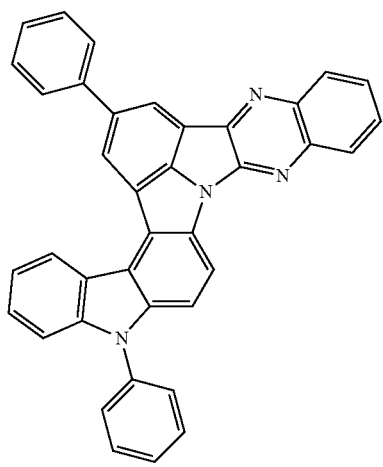
A-31
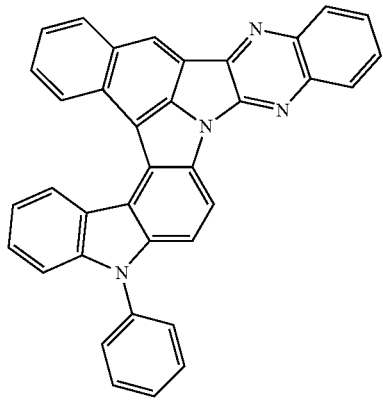
A-32
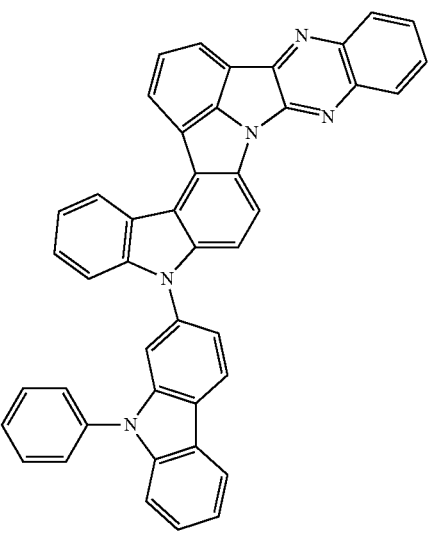
A-33
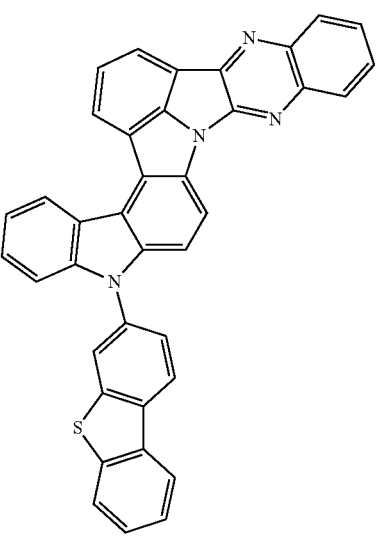
A-34
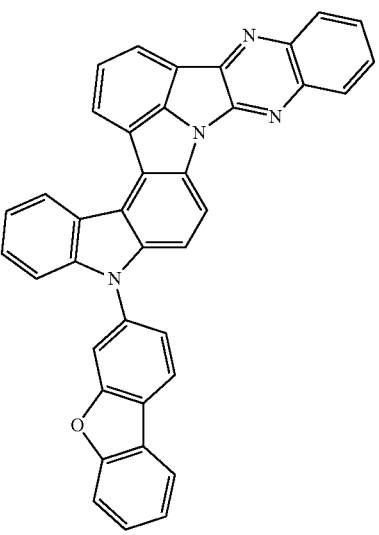

A-35
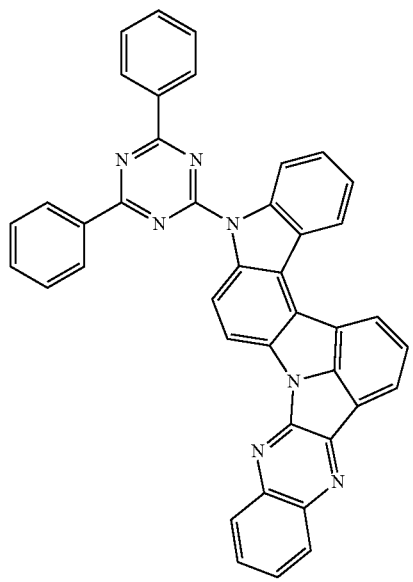
A-36
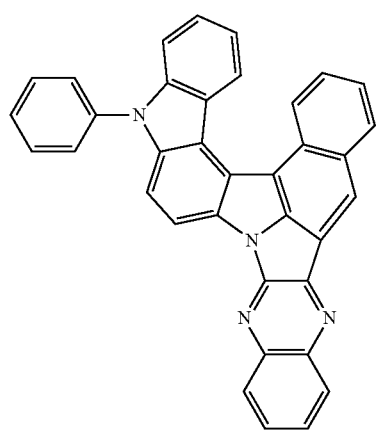
A-37
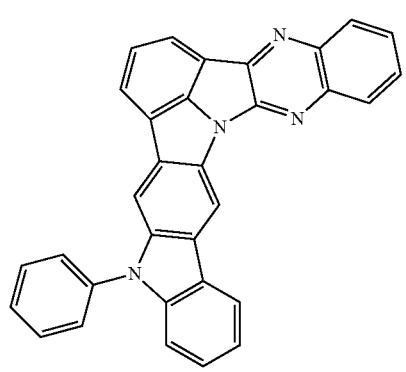
A-38
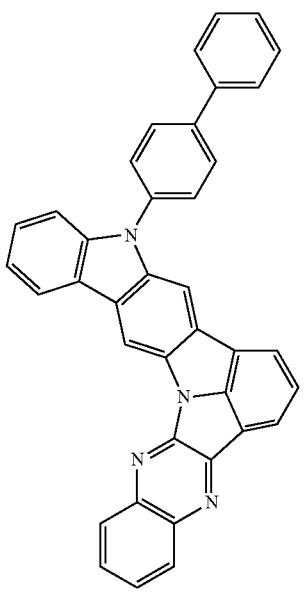
A-39
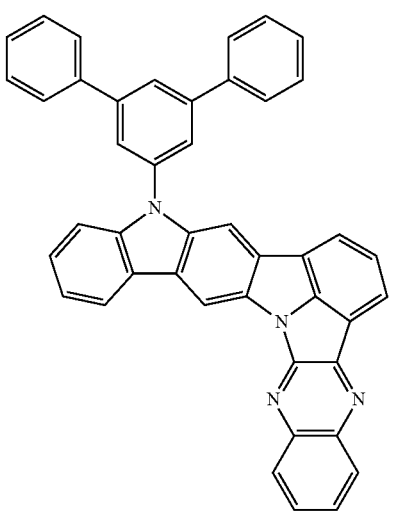
A-40
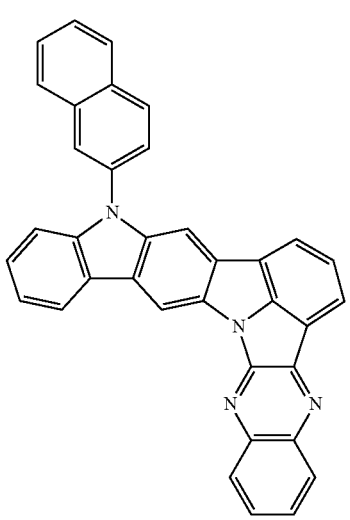

-continued
A-41
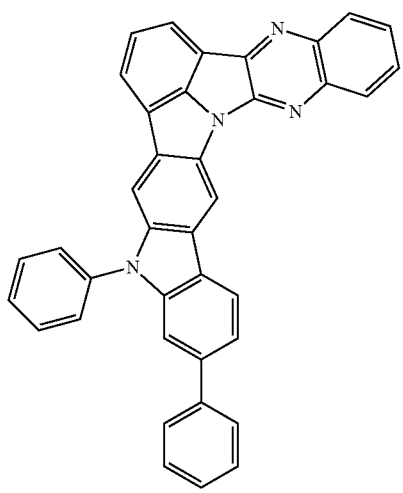
A-42
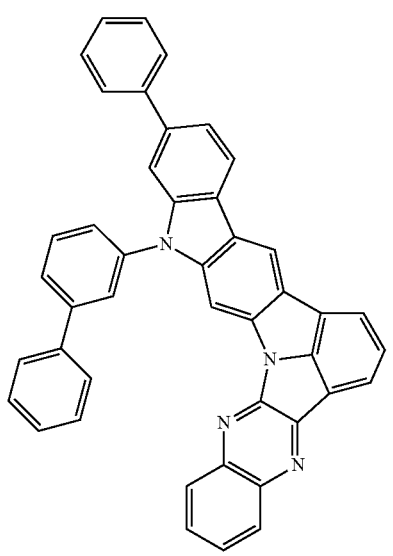
A-43
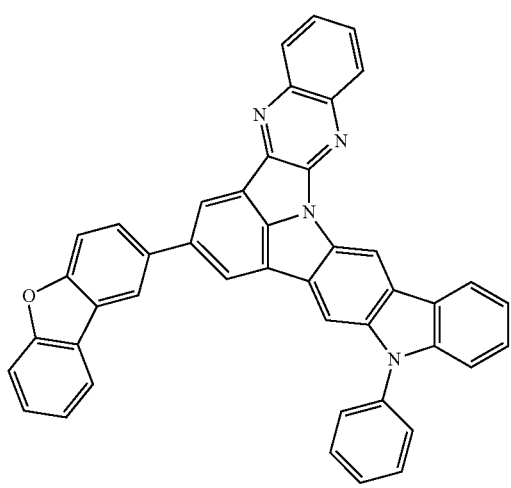
-continued
A-44
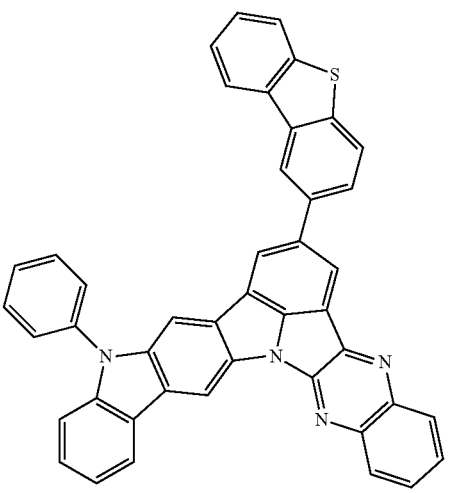
A-45
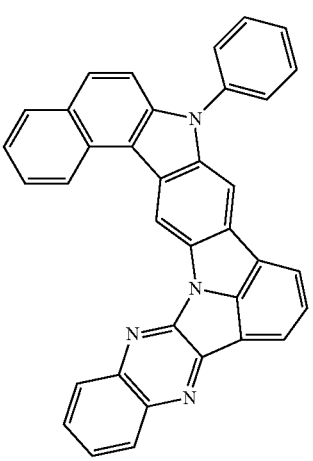
A-46
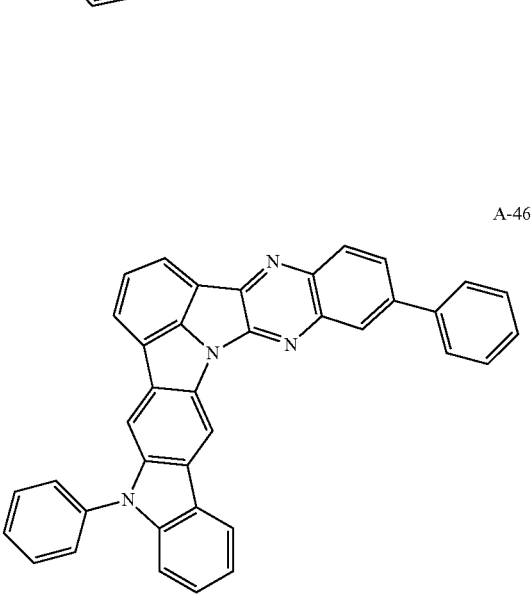

A-47
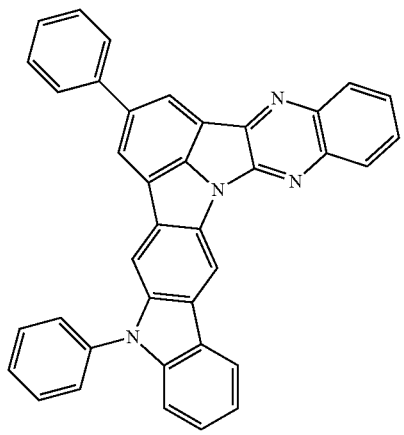
A-48
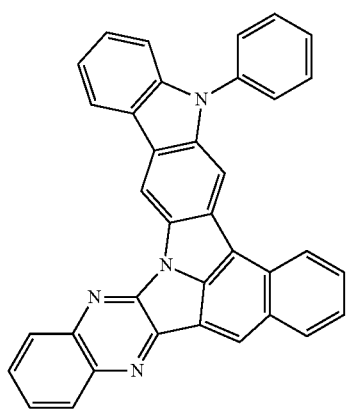
A-49
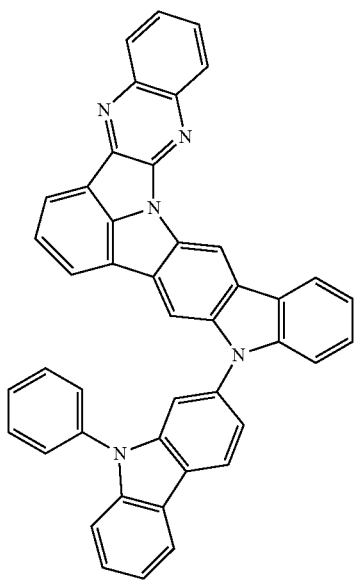
A-50
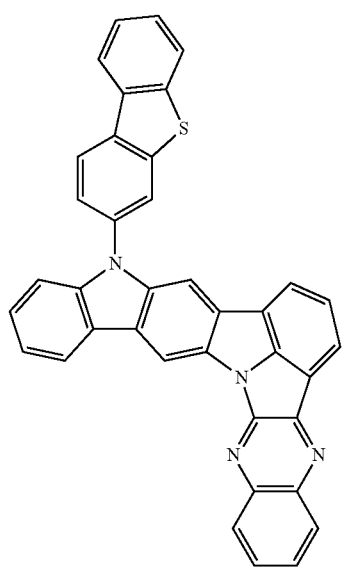
A-51
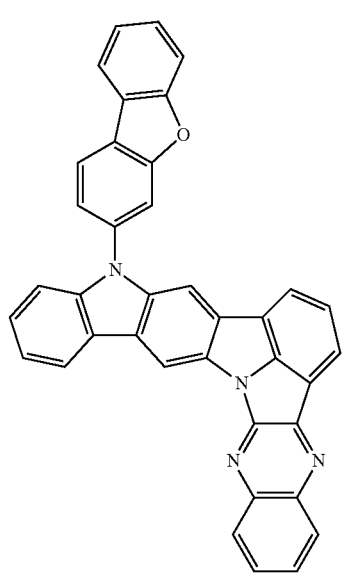
A-52
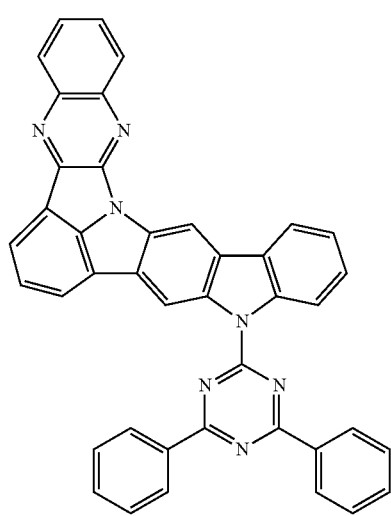

A-53
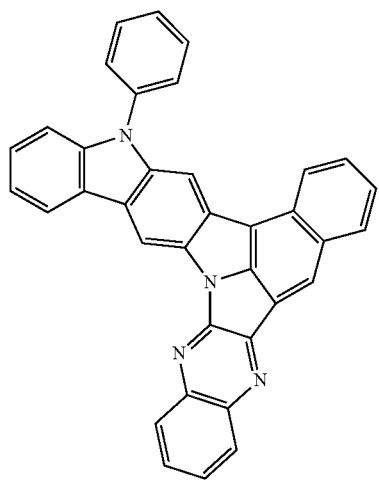
A-56
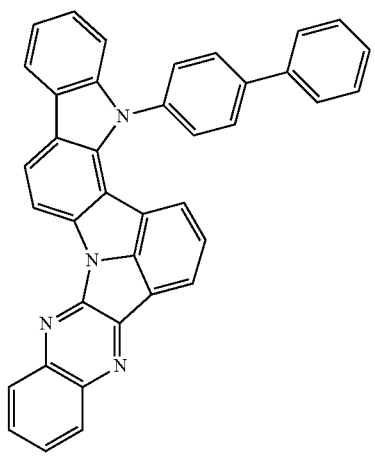
A-54
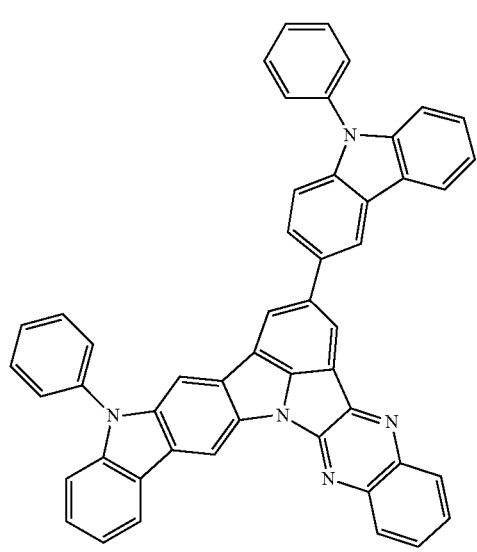
A-57
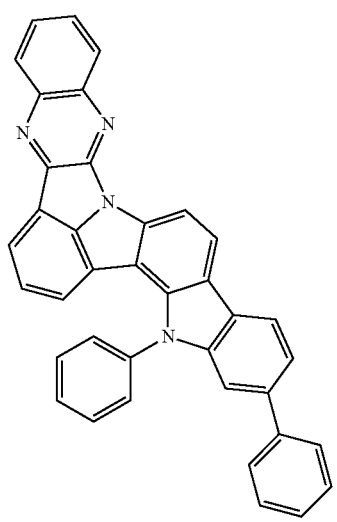
A-55
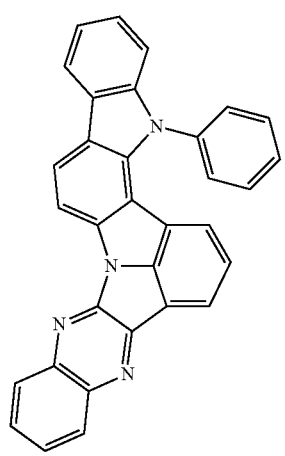
A-58
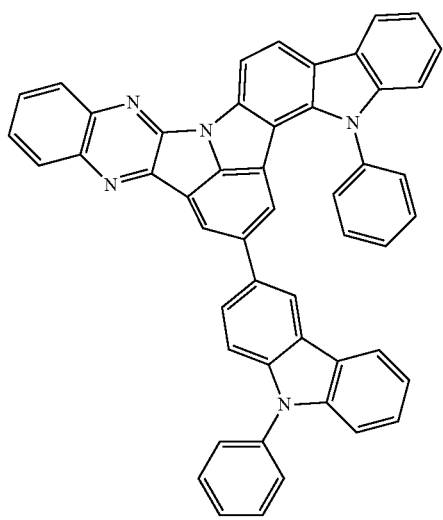

A-59
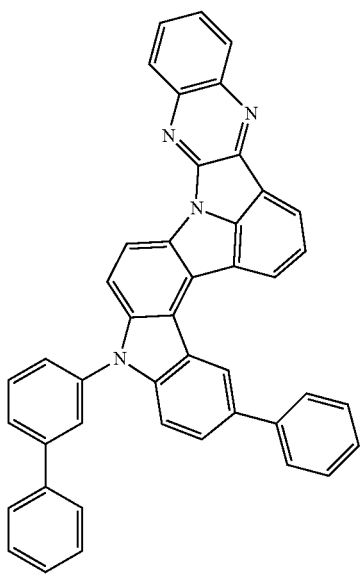
A-60
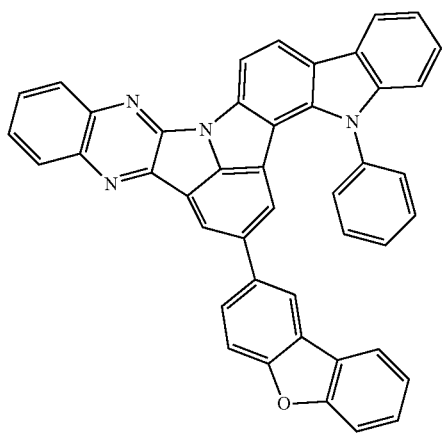
A-61
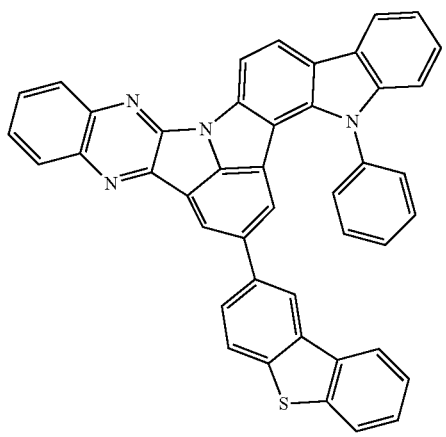
A-62
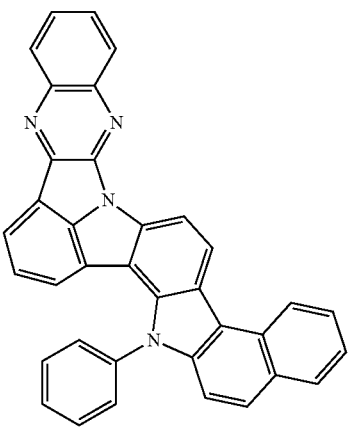
A-63
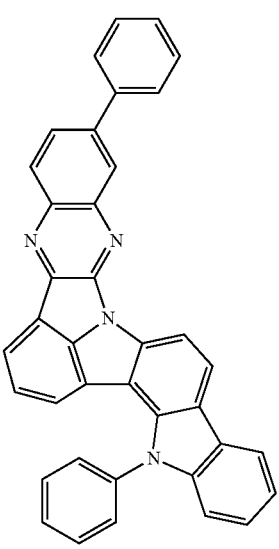
A-64
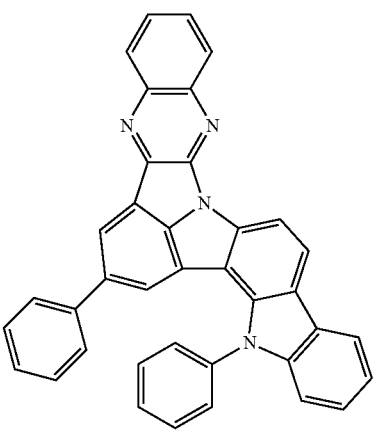

A-65
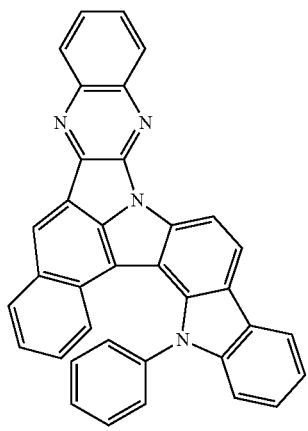
A-66
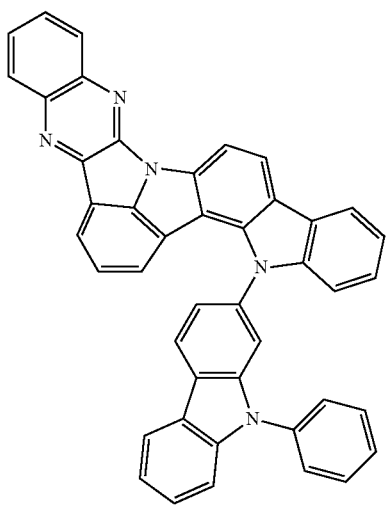
A-67
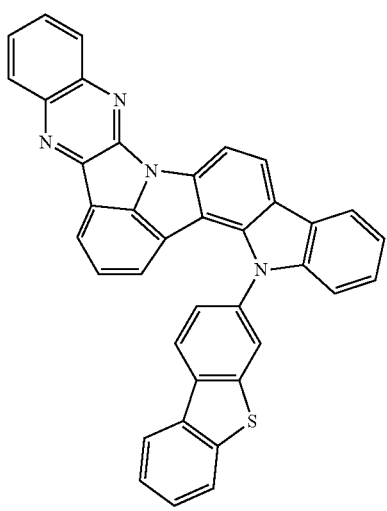
A-68
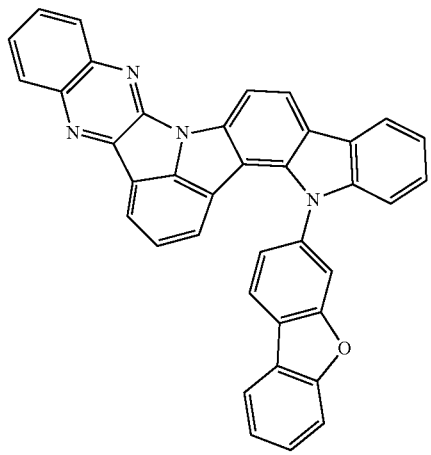
A-69
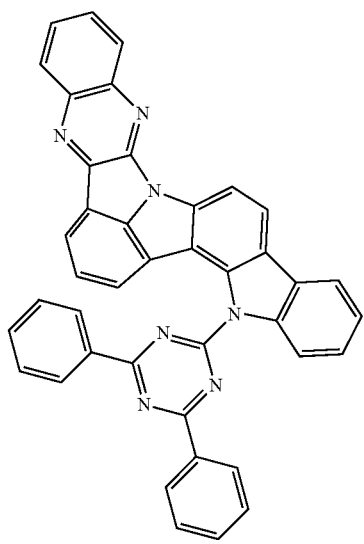
A-70
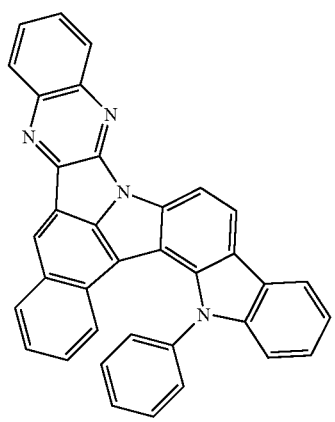

A-71
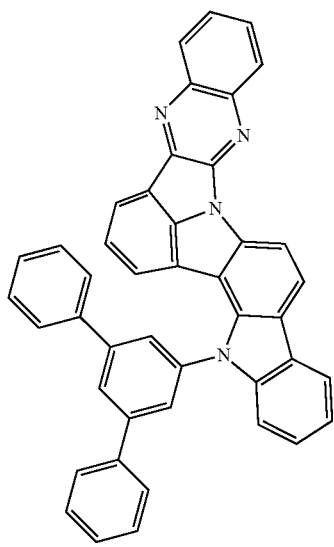
A-72
A-73
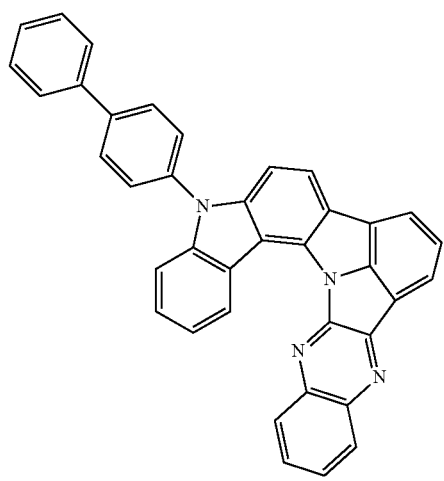
A-74
A-75
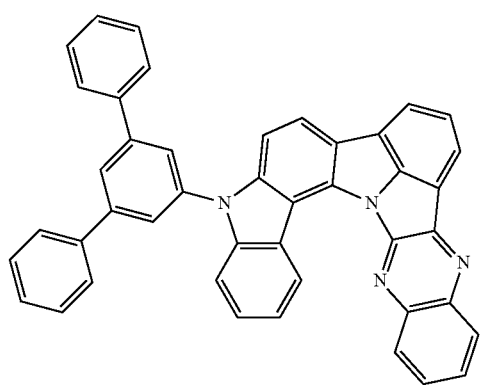
A-76
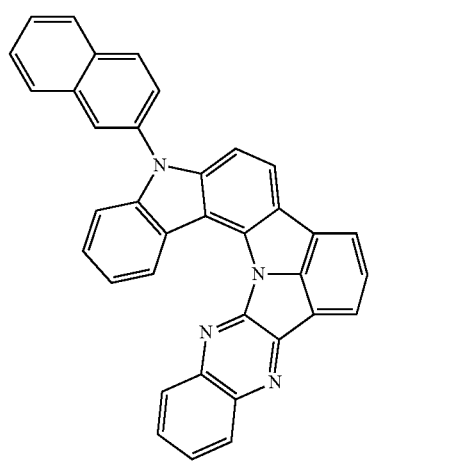

-continued
A-77
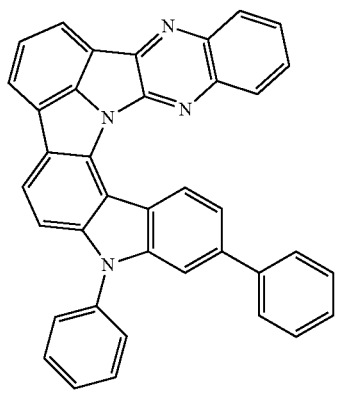
A-78
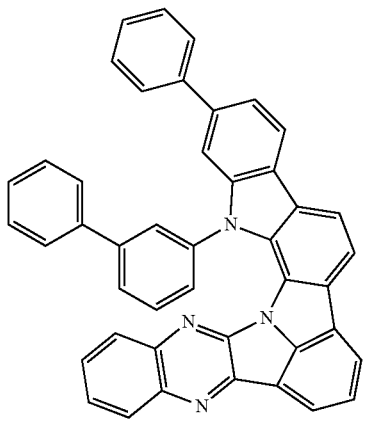
A-79
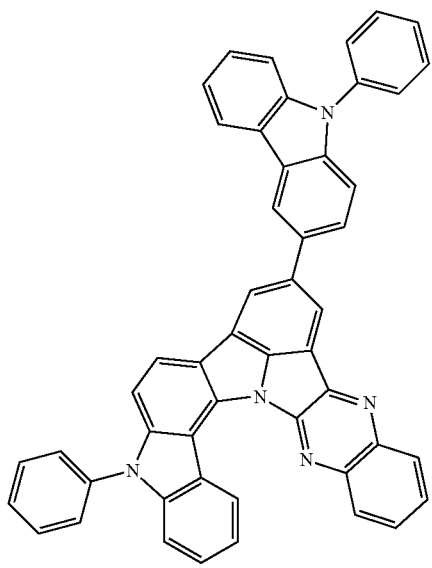
-continued
A-80
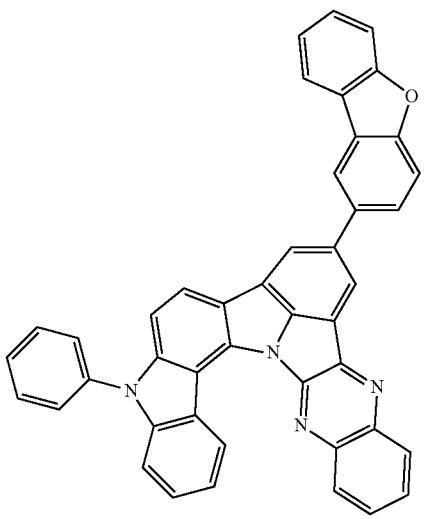
A-81
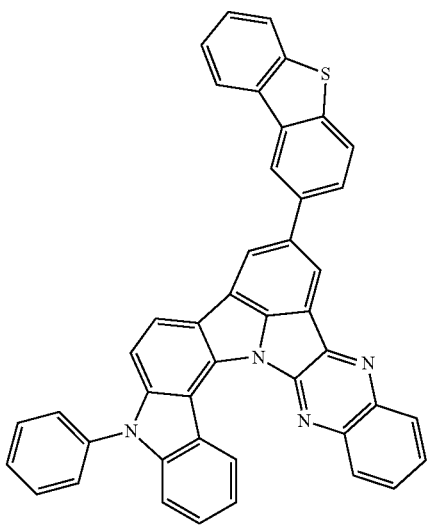
A-82
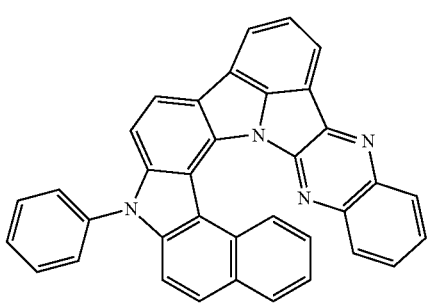

-continued
A-83
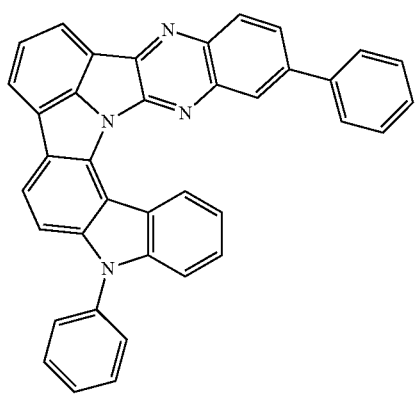
A-84
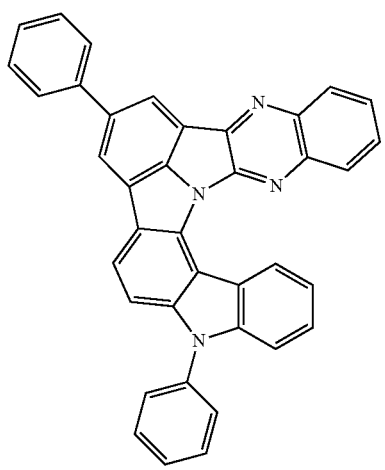
A-85
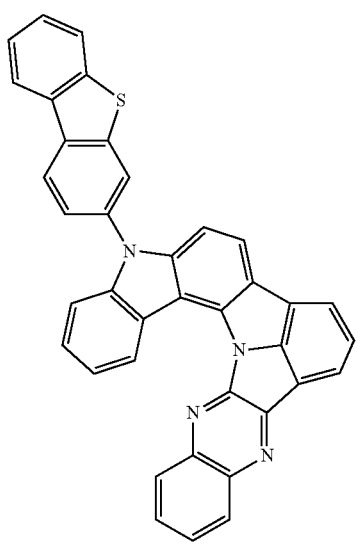
-continued
A-86
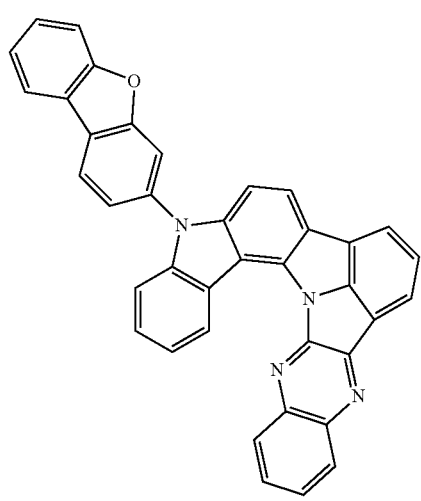
A-87
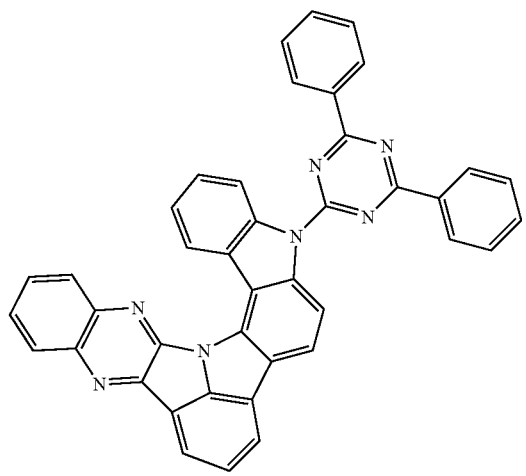
A-88
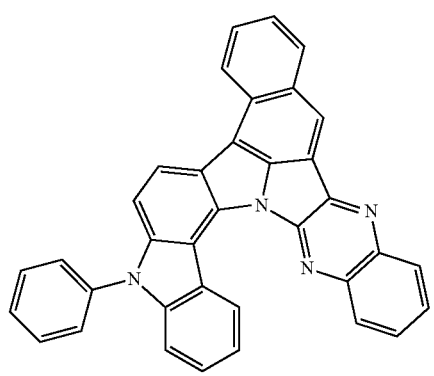

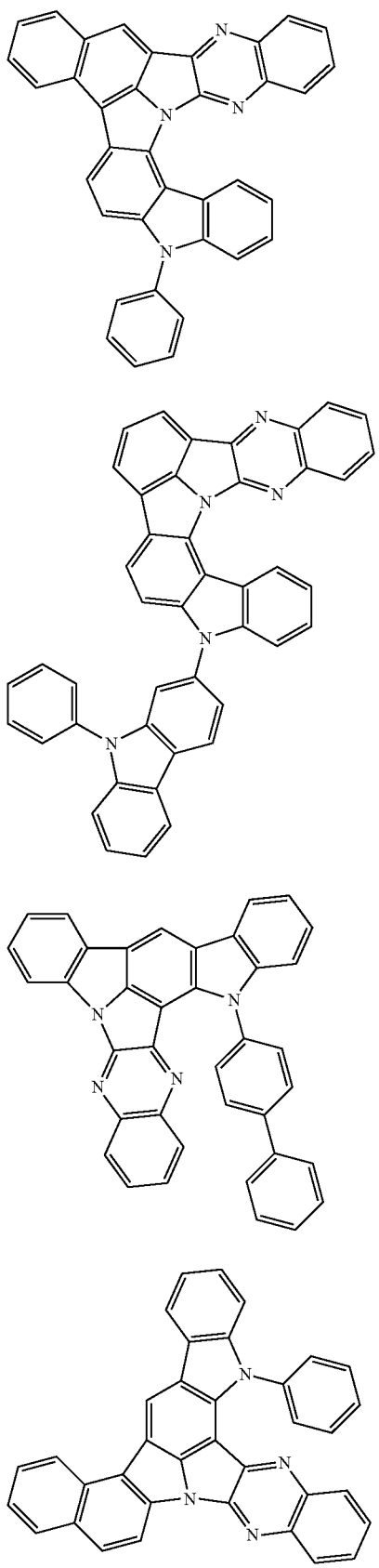
A-89
A-90
A-91
A-92
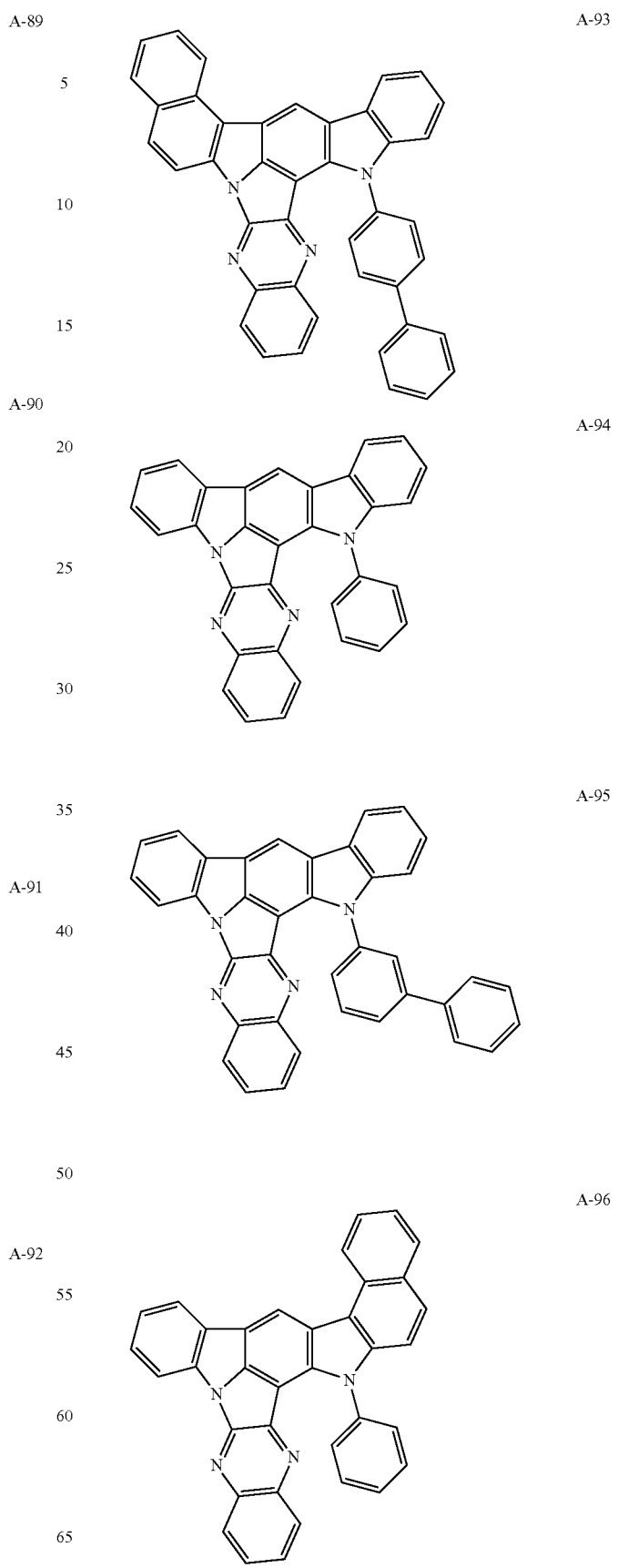
A-93
A-94
A-95
A-96

A-97
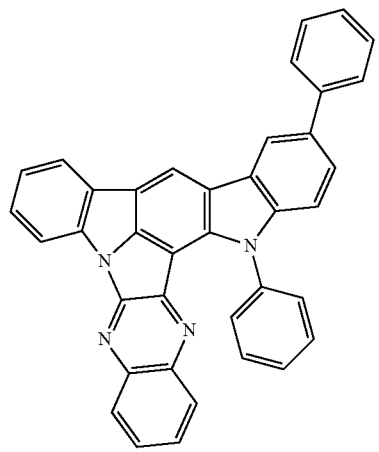
A-98
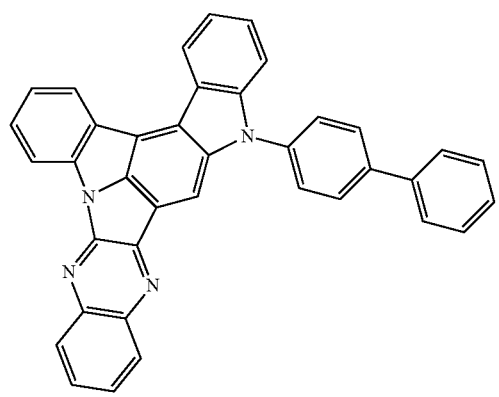
A-99
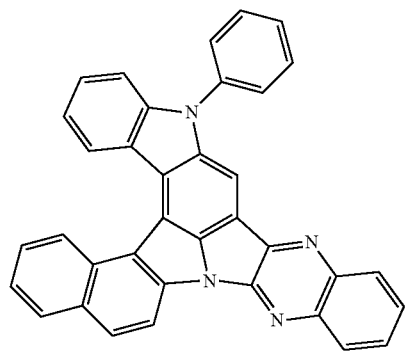
A-100
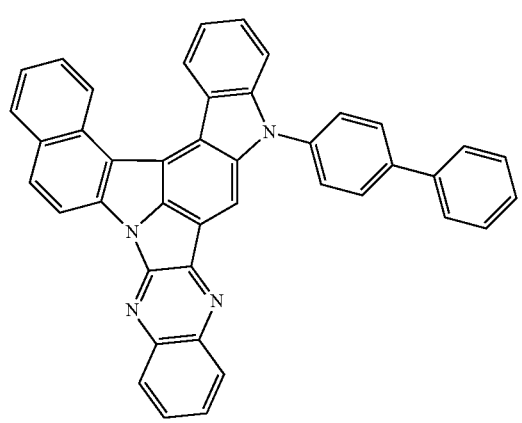
A-101
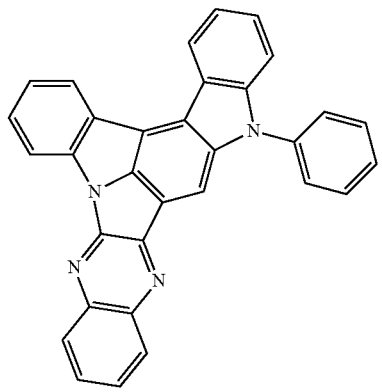
A-102
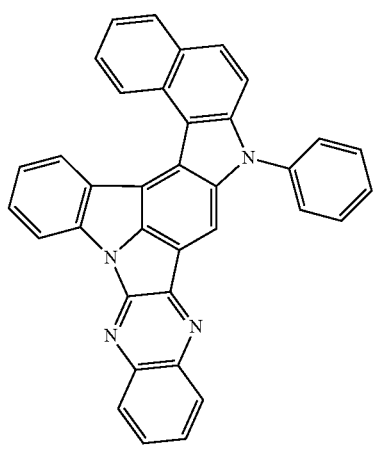
A-103

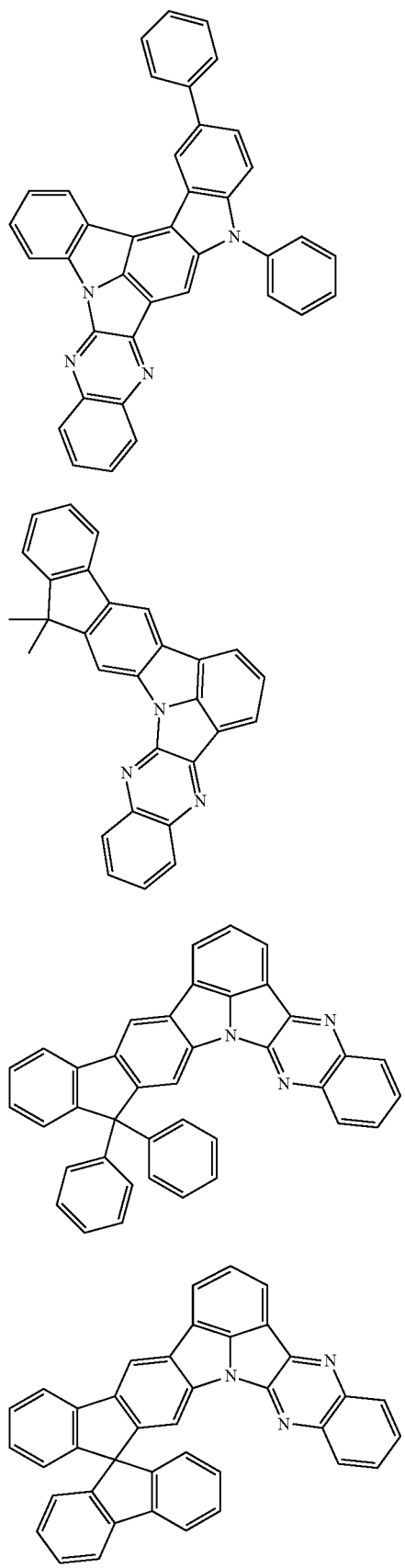
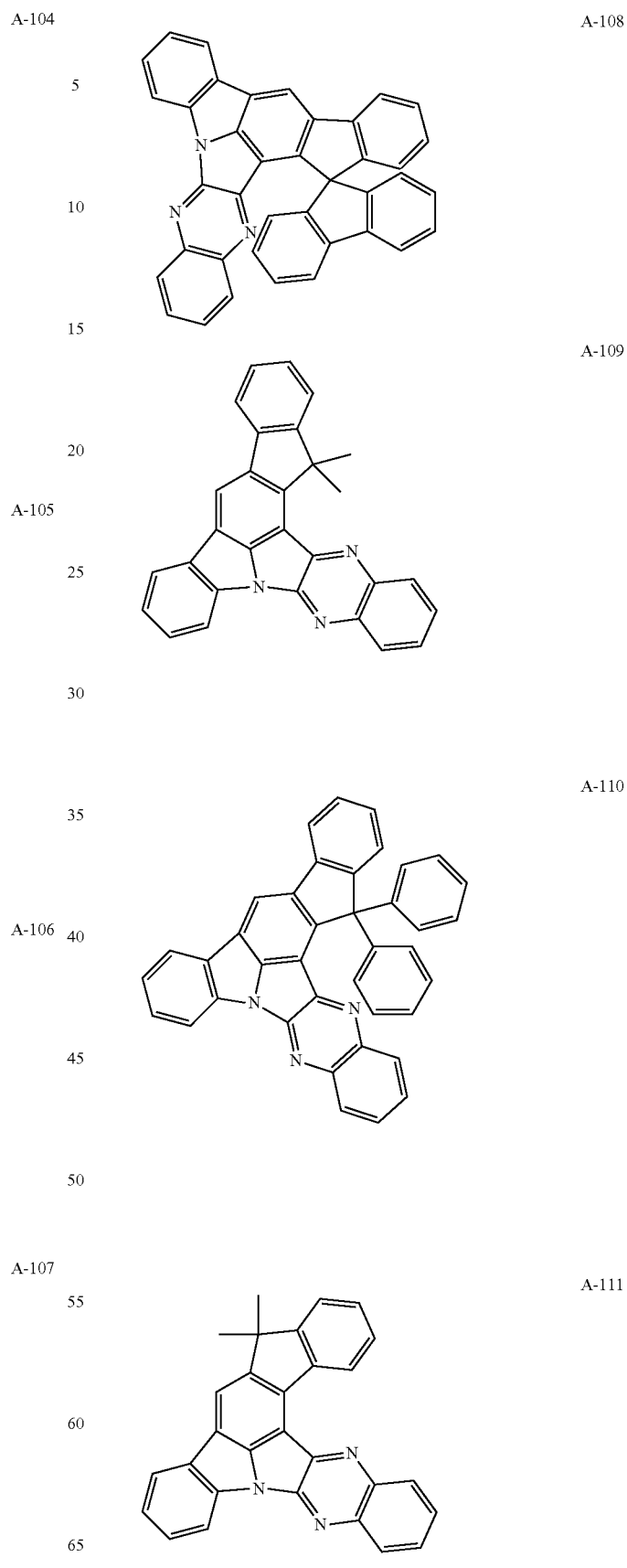

A-112
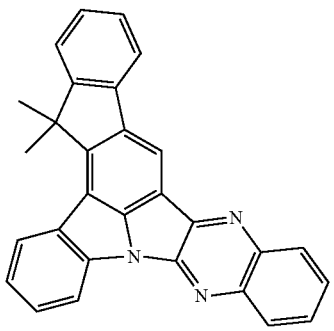
A-113
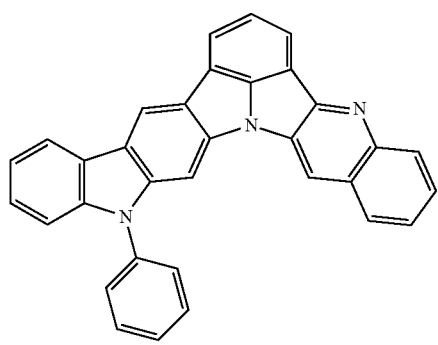
A-114
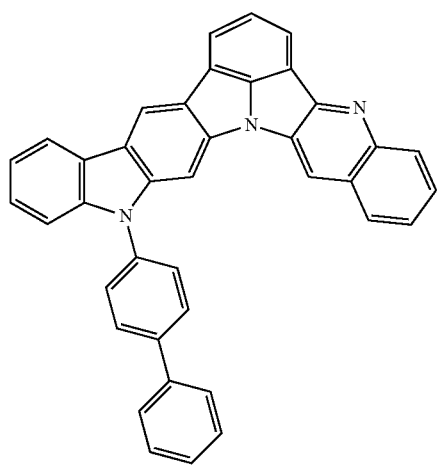
A-115
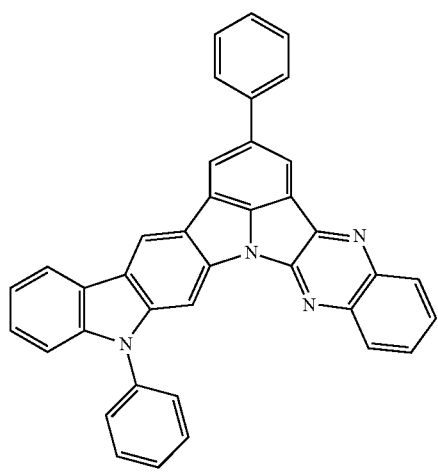
A-116
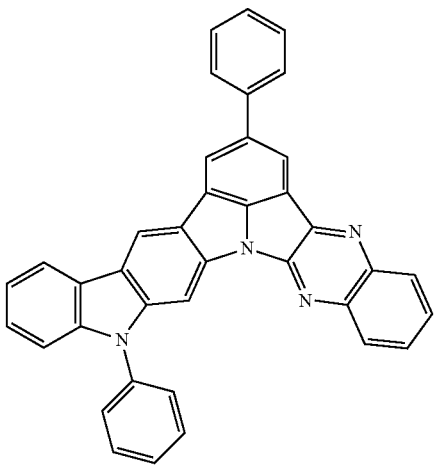
A-117
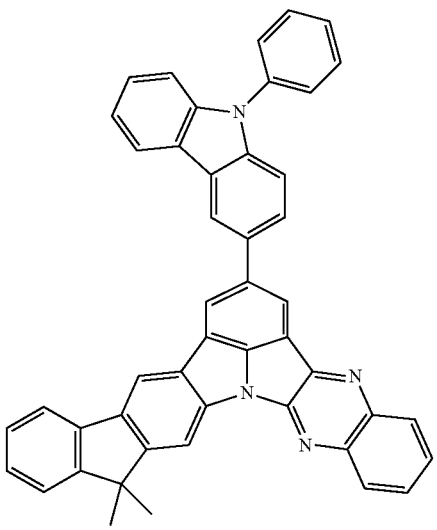
A-118
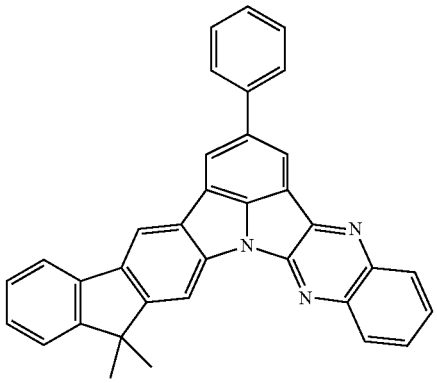

A-119
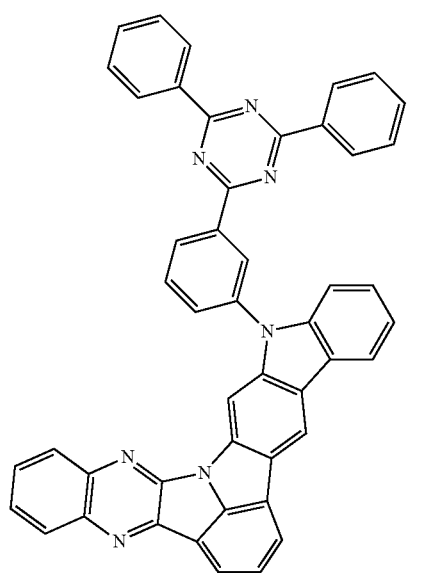
A-120
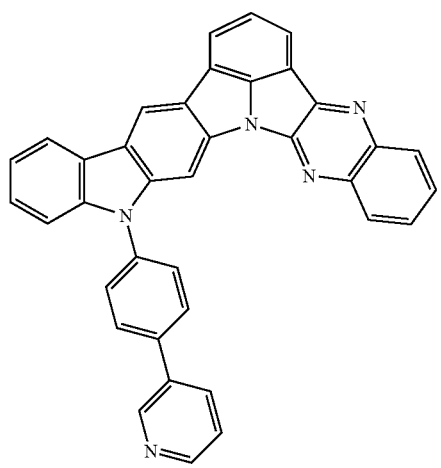
A-121
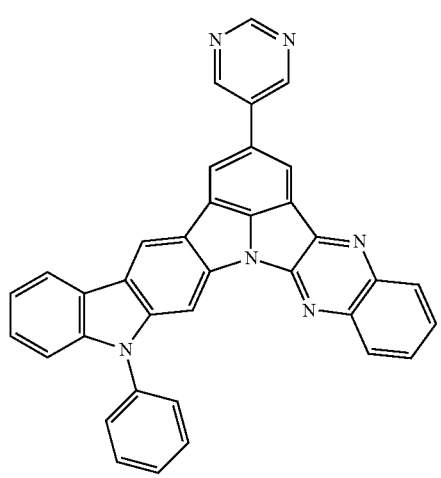
A-122
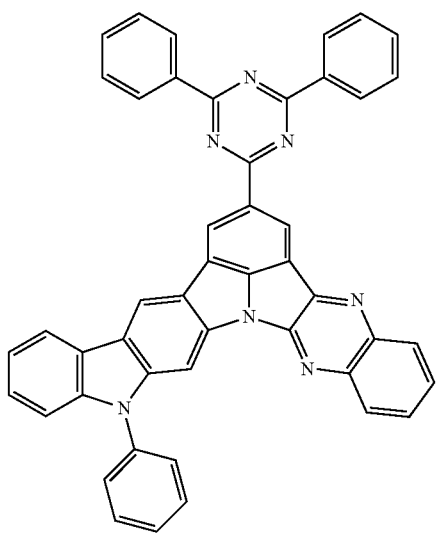
A-123
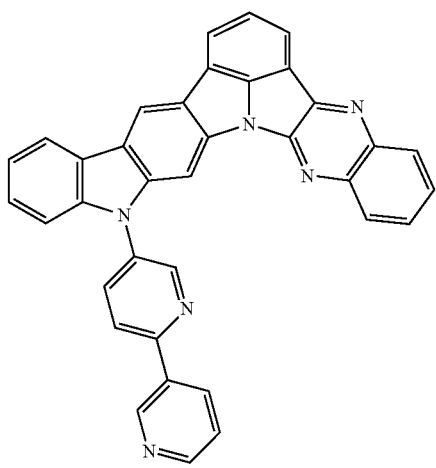
A-124
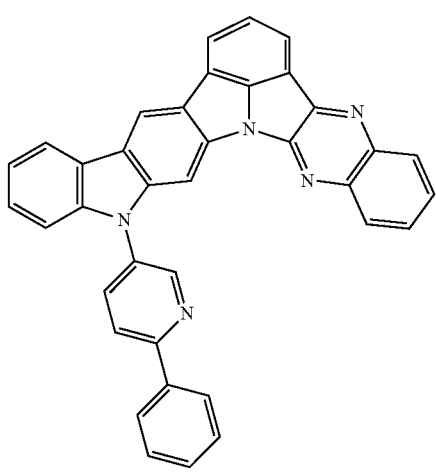
The organic electroluminescent compounds of the present invention can be prepared by a synthetic method known to a person skilled in the art. For example, they can be prepared according to the following reaction scheme.

[Reaction Scheme 1]

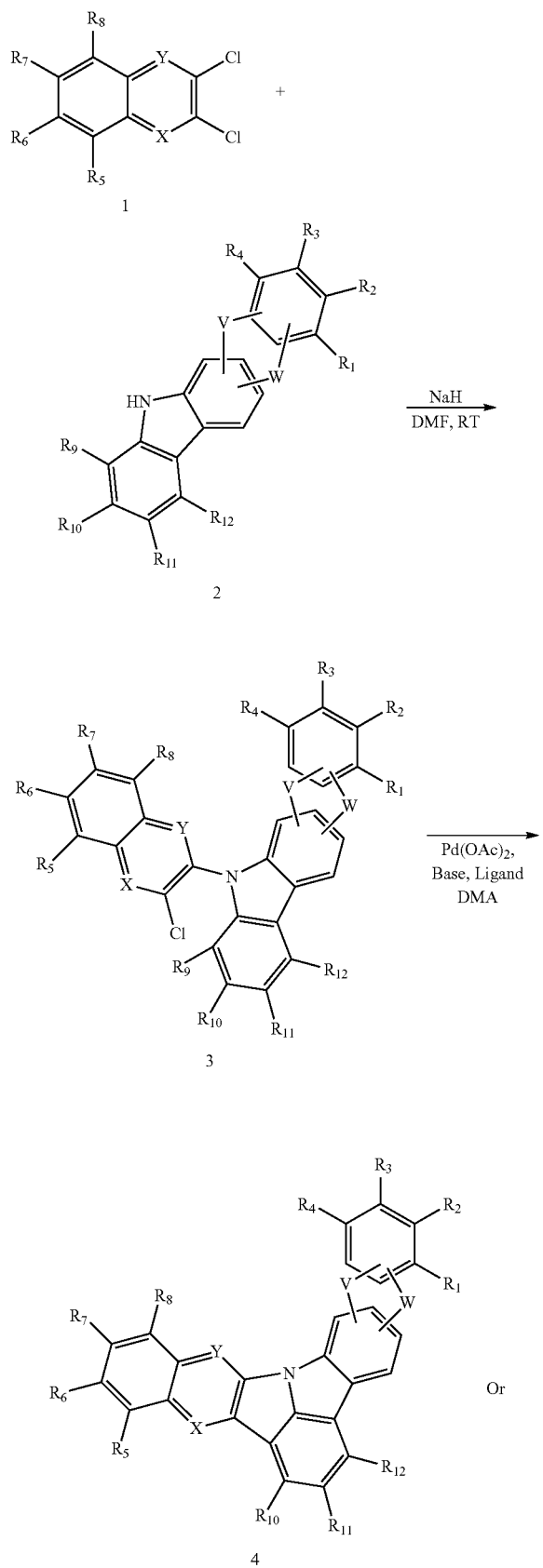

wherein $R_1$ to $R_{12}$, V, W, X, and Y are as defined in formula 1 or 2.

The present invention provides an organic electroluminescent material comprising the organic electroluminescent compound of formula 1 or 2, and an organic electroluminescent device comprising the material.

The above material can be comprised of the organic electroluminescent compound according to the present invention alone, or can further include conventional materials generally used in organic electroluminescent materials.

The organic electroluminescent device comprises a first electrode; a second electrode; and at least one organic layer between the first and second electrodes. The organic layer may comprise at least one organic electroluminescent compound of formula 1 or 2.

One of the first and second electrodes can be an anode, and the other can be a cathode. The organic layer comprises a light-emitting layer, and may further comprise at least one layer selected from the group consisting of a hole injection layer, a hole transport layer, an electron transport layer, an electron injection layer, an interlayer, a hole blocking layer, and an electron blocking layer.

The organic electroluminescent compound of formula 1 or 2 according to the present invention can be comprised in the light-emitting layer. Where used in the light-emitting layer, the organic electroluminescent compound of formula 1 or 2 according to the present invention can be comprised as a host material. Preferably, the light-emitting layer can further comprise one or more dopants. If necessary, a compound other than the organic electroluminescent compound of formula 1 or 2 according to the present invention can be additionally comprised as a second host material. Herein, the weight ratio of the first host material to the second host material is in the range of 1:99 to 99:1.

The second host material can be any of the known phosphorescent hosts. Specifically, the phosphorescent host selected from the group consisting of the compounds of formulae 11 to 15 below is preferable in terms of luminous efficiency.

$$H\text{---}(Cz\text{---}L_4)_h\text{---}M \tag{11}$$

$$H\text{---}(Cz)_i\text{---}L_4\text{---}M \tag{12}$$

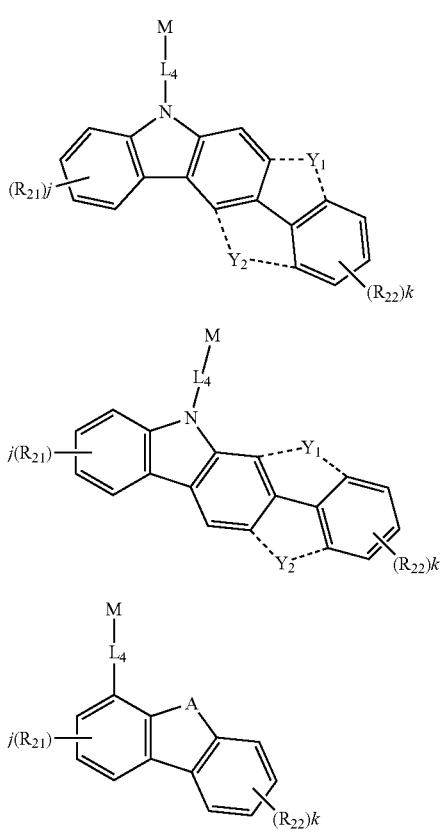

wherein Cz represents the following structure;

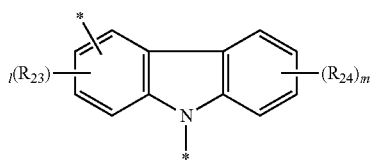

A represents —O— or —S—;

$R_{21}$ to $R_{24}$ each independently represent hydrogen, deuterium, a halogen, a substituted or unsubstituted (C1-C30)alkyl, a substituted of unsubstituted (C6-C30)aryl, a substituted or unsubstituted 5- to 30-membered heteroaryl, or —$SiR_{25}R_{26}R_{27}$;

$R_{25}$ to $R_{27}$ each independently represent a substituted or unsubstituted (C1-C30)alkyl, or a substituted or unsubstituted (C6-C30)aryl;

$L_4$ represents a single bond, a substituted or unsubstituted (C6-C30)arylene, or a substituted or unsubstituted 5- to 30-membered heteroarylene;

M represents a substituted or unsubstituted (C6-C30)aryl, or a substituted or unsubstituted 5- to 30-membered heteroaryl;

$Y_1$ and $Y_2$ each independently represent —O—, —S—, —N($R_{31}$)—, or —C($R_{32}$)($R_{33}$)—, provided that $Y_1$ and $Y_2$ do not simultaneously exist;

$R_{31}$ to $R_{33}$ each independently represent a substituted or unsubstituted (C1-C30)alkyl, a substituted or unsubstituted (C6-C30)aryl, or a substituted or unsubstituted 5- to 30-membered heteroaryl, and $R_{32}$ and $R_{33}$ may be the same or different;

h and i each independently represent an integer of 1 to 3;

j, k, l, and m each independently represent an integer of 0 to 4; and where h, i, j, k, l, or m is an integer of 2 or more, each of (Cz-$L_4$), each of (Cz), each of $R_{21}$, each of $R_{22}$, each of $R_{23}$, or each of $R_{24}$ may be the same or different.

Specifically, preferable examples of the second host material are as follows:

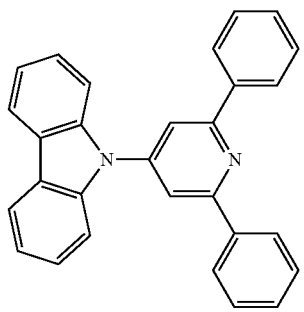

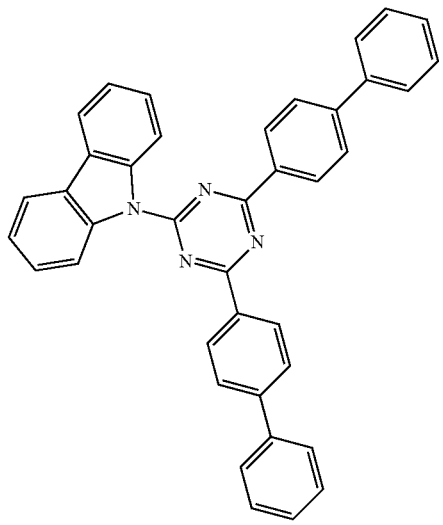

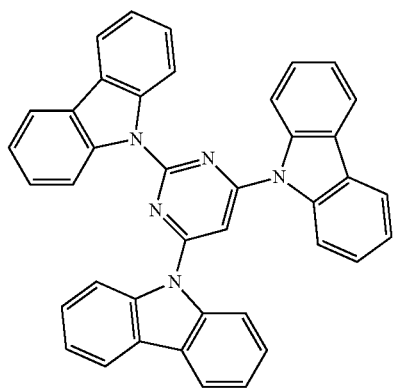

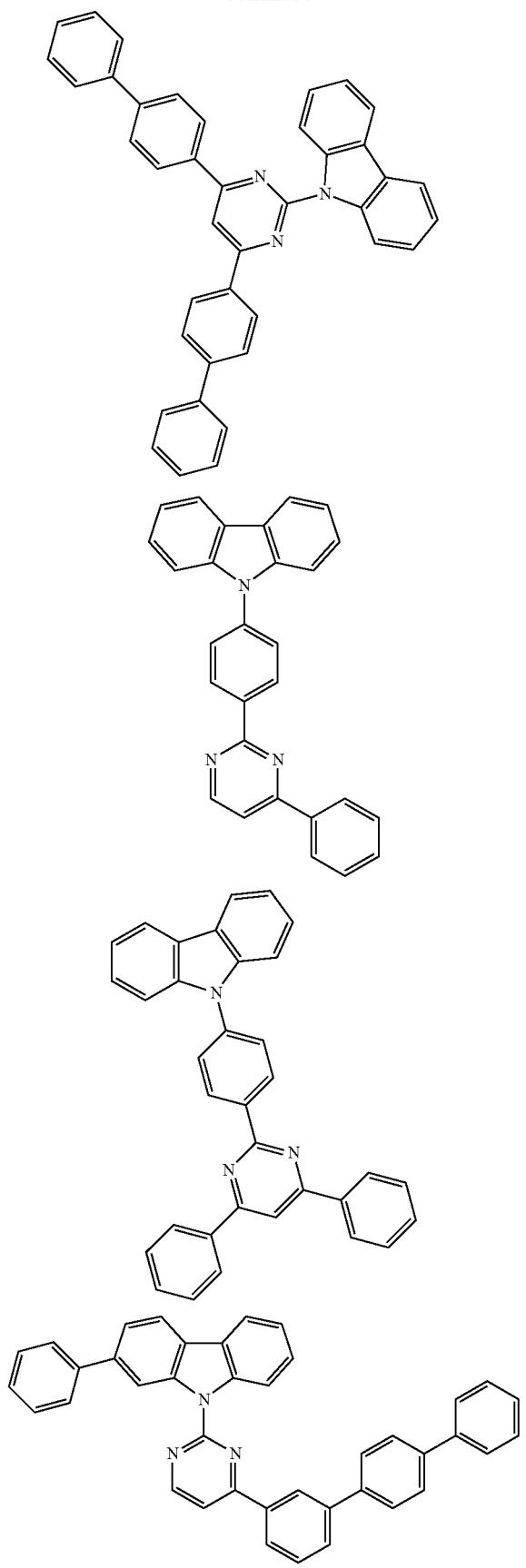
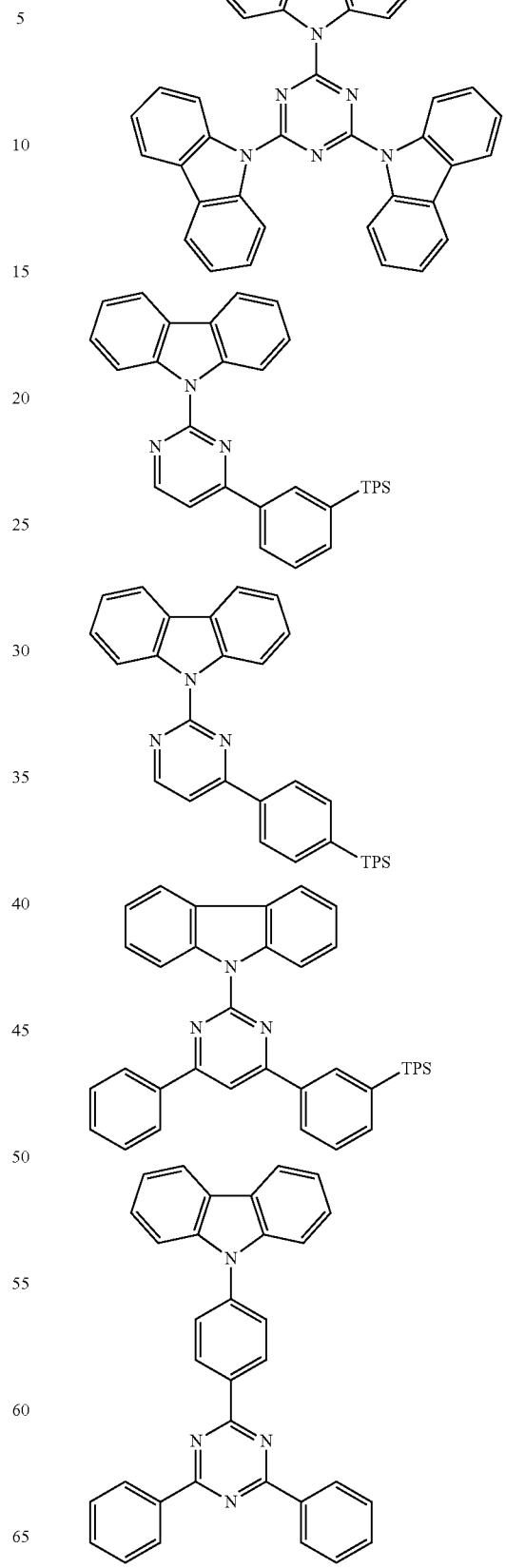

51
-continued
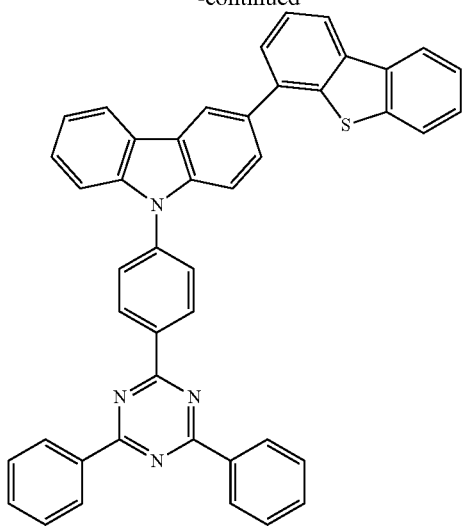
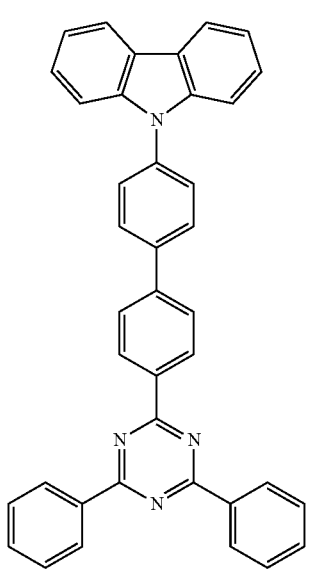
52
-continued
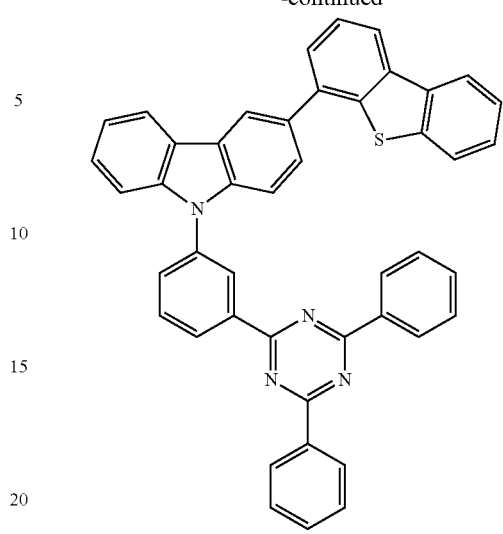
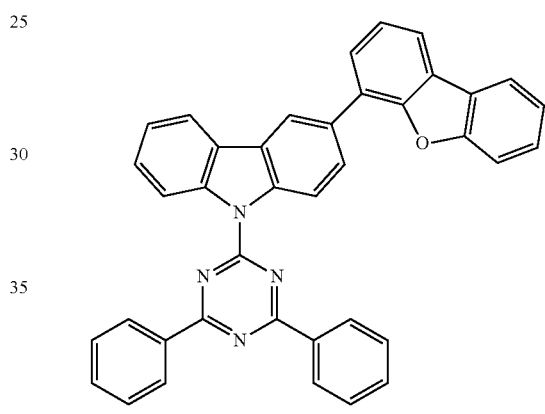
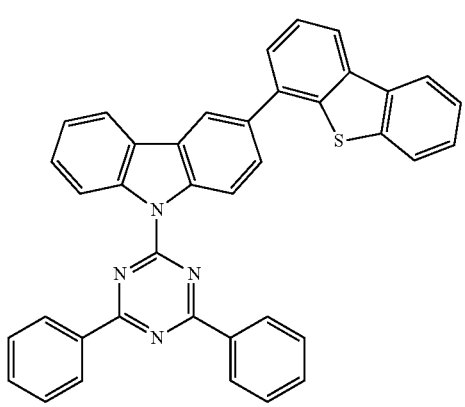
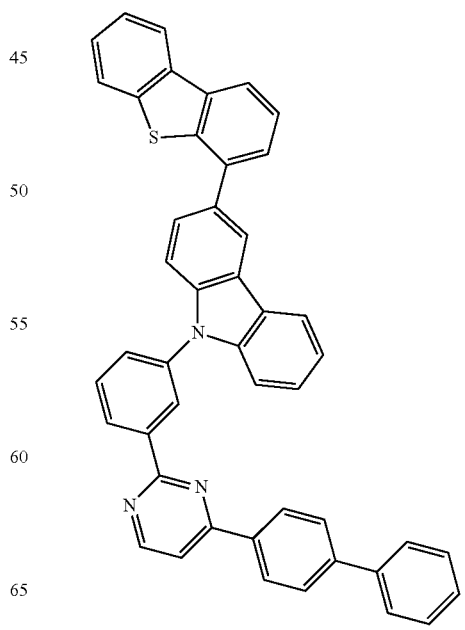

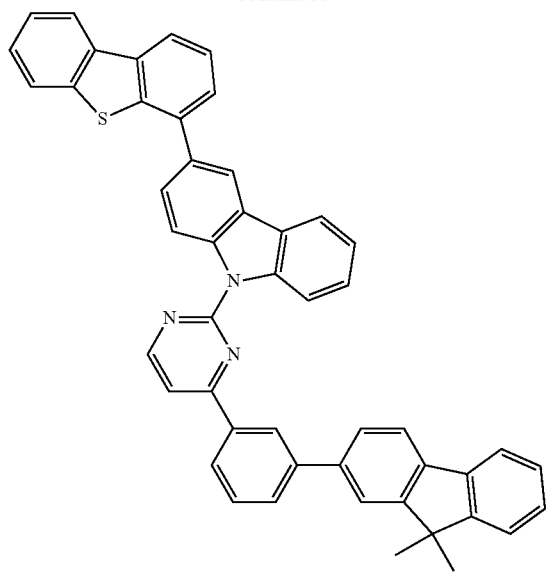
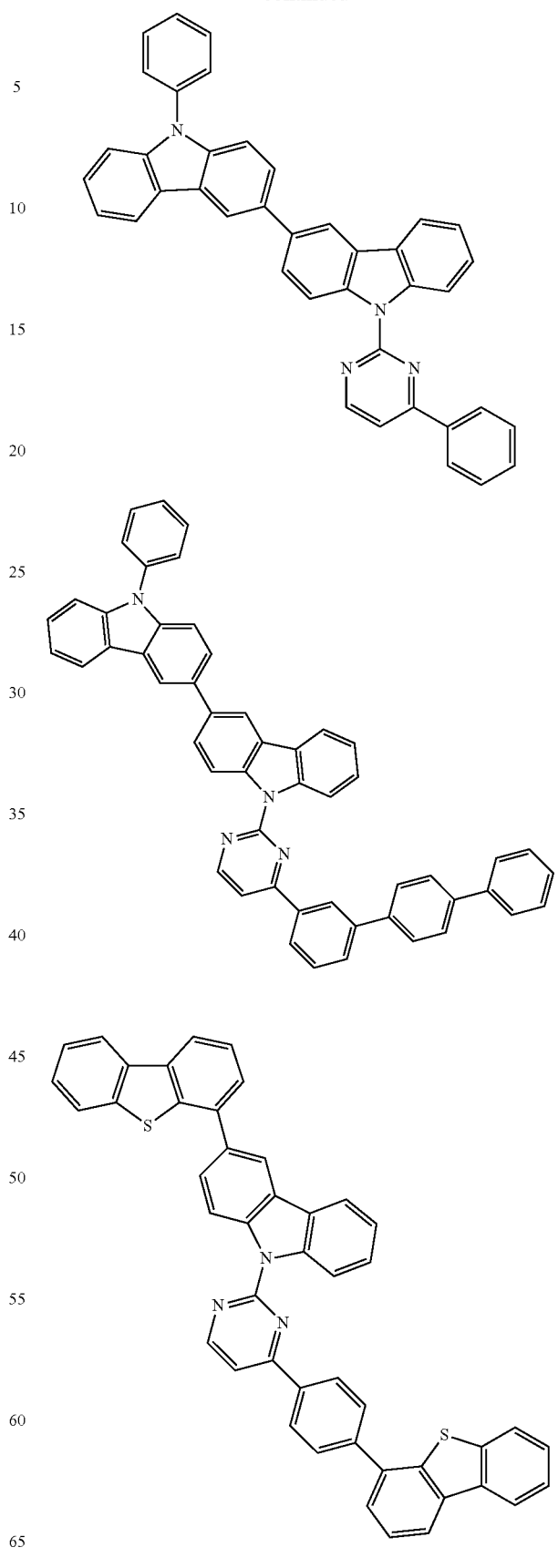

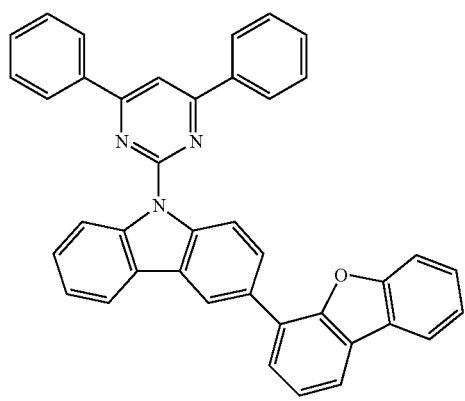
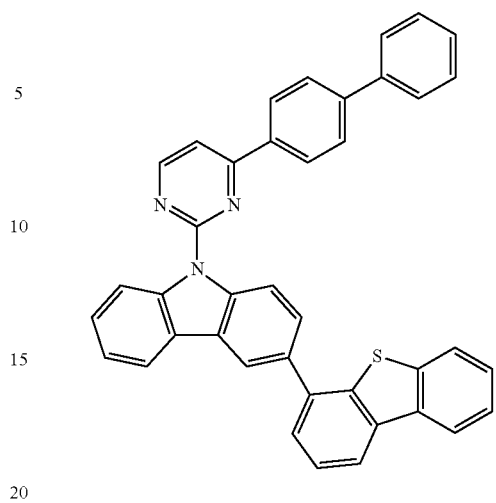
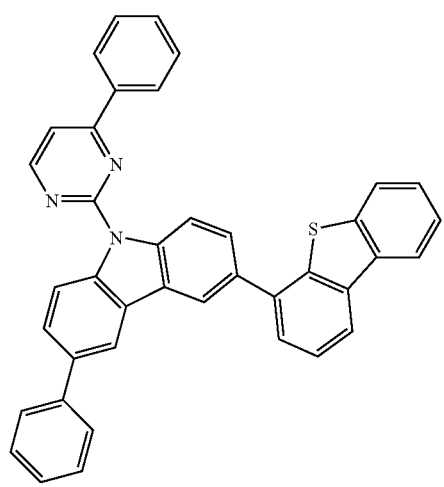
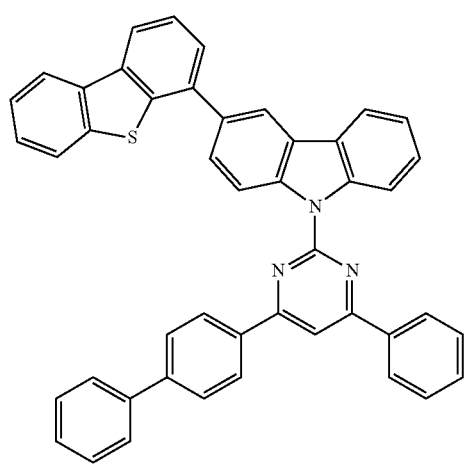

57
-continued
58
-continued
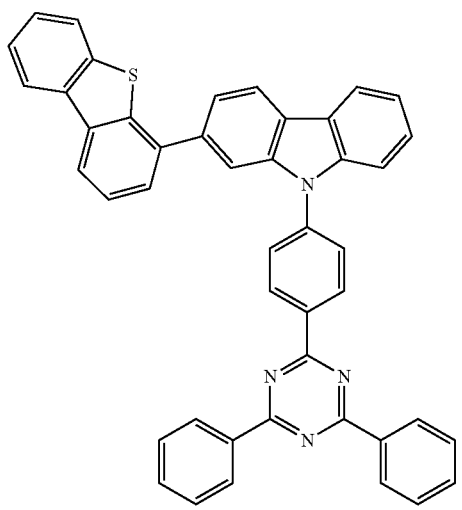
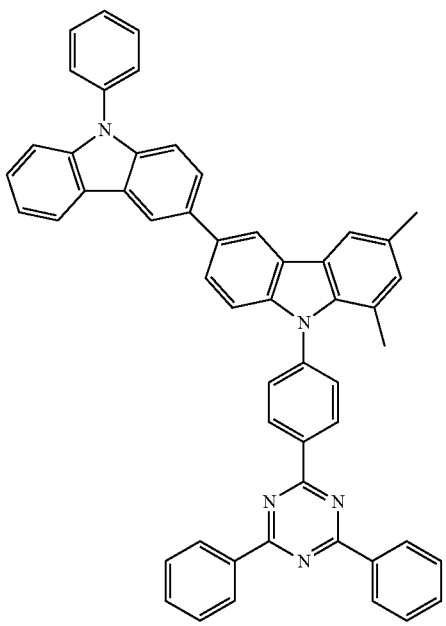
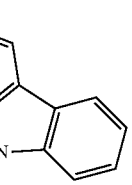
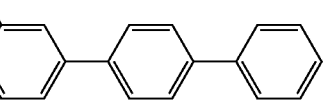
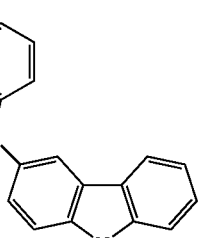
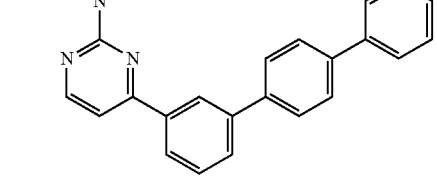

59
-continued
60
-continued
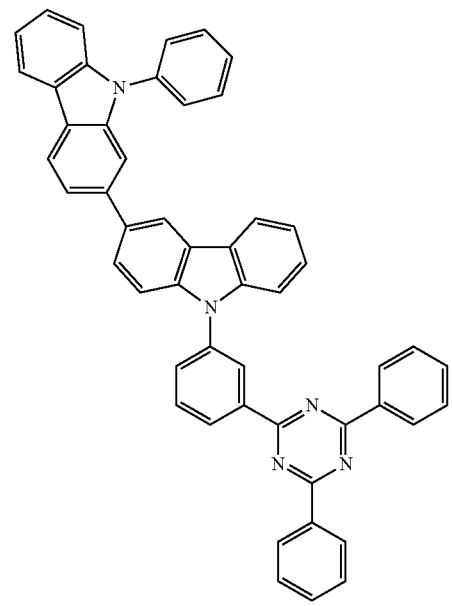
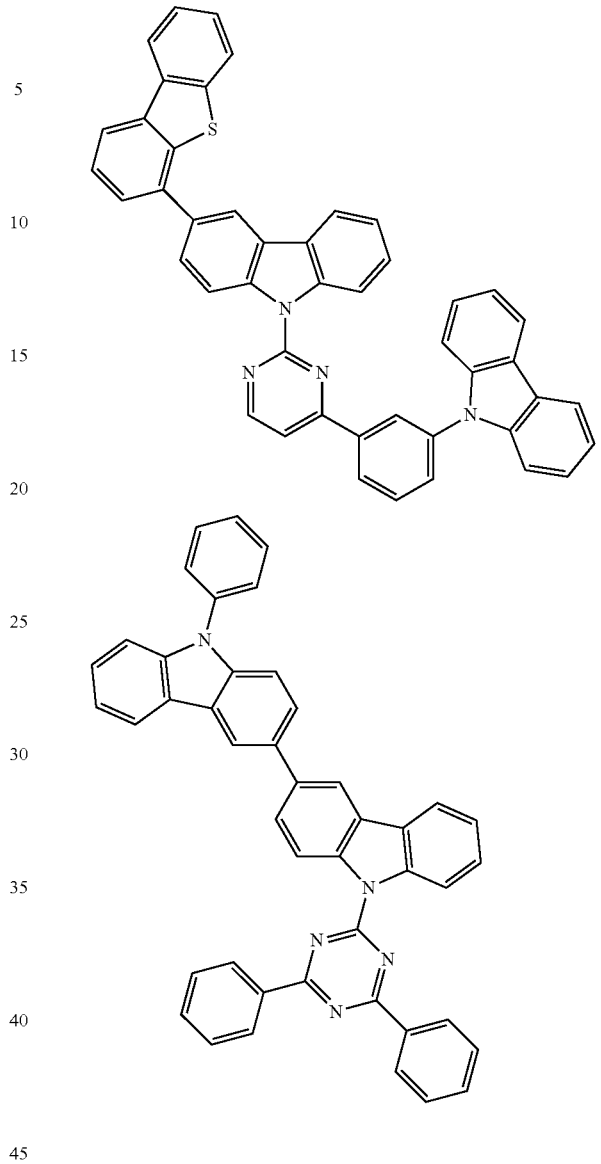
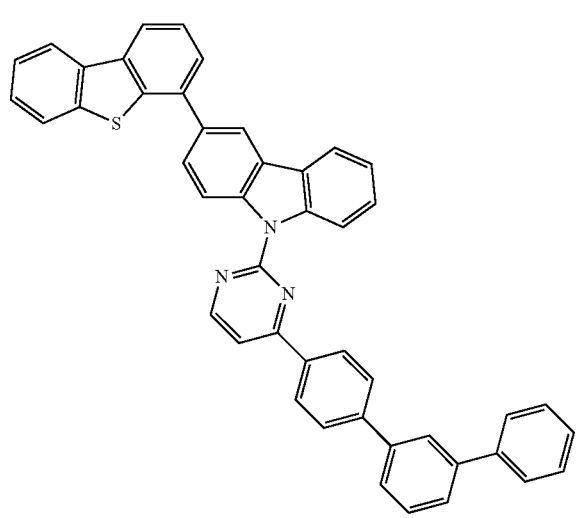

61
-continued
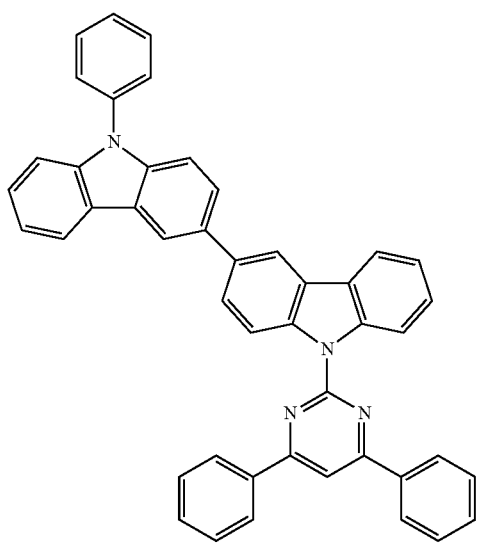
62
-continued
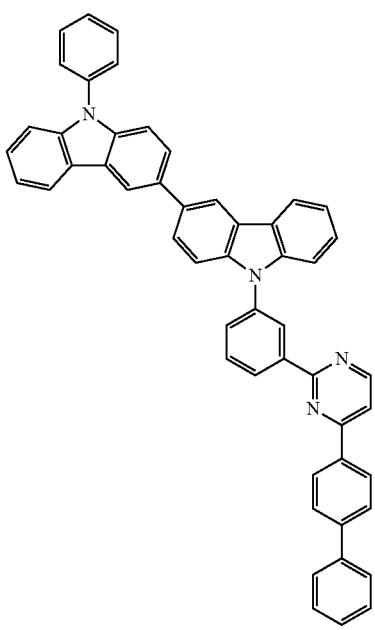
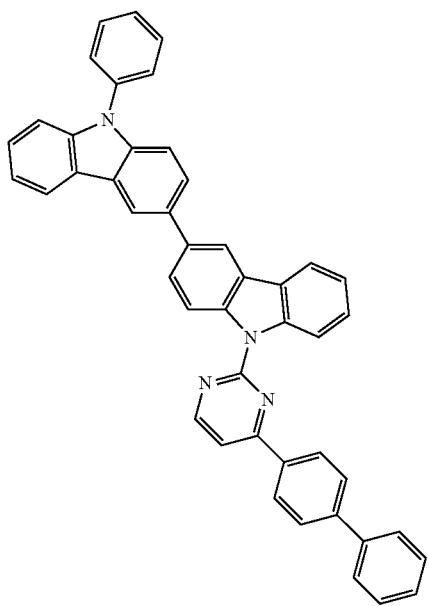
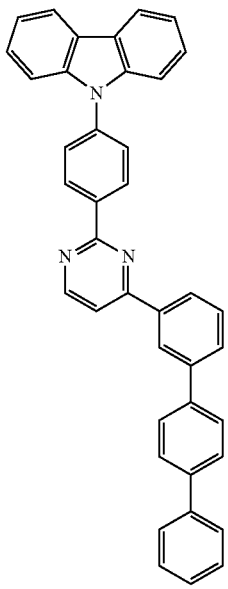

-continued
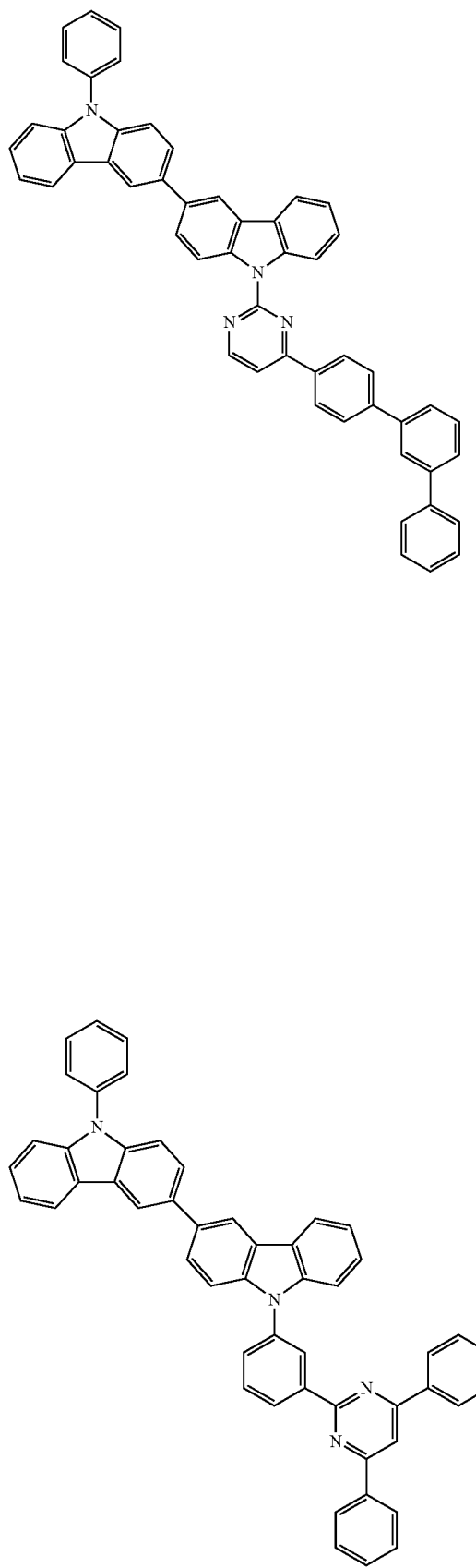
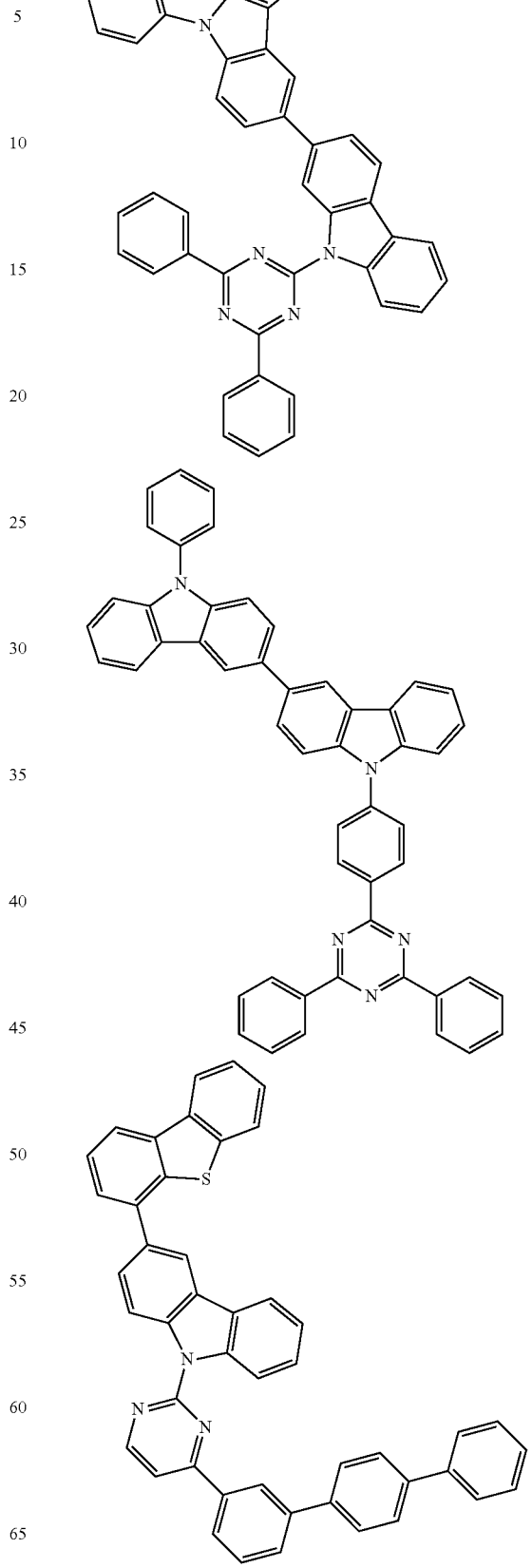

65
-continued
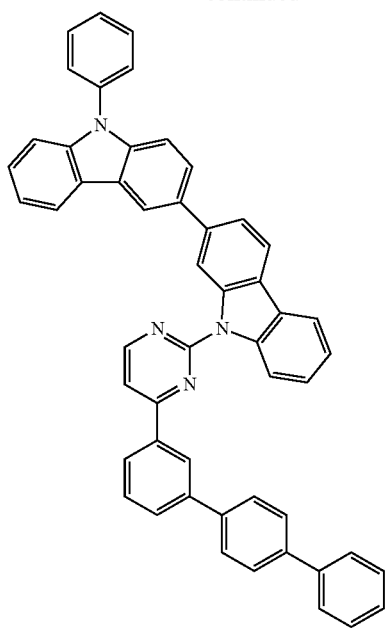
66
-continued
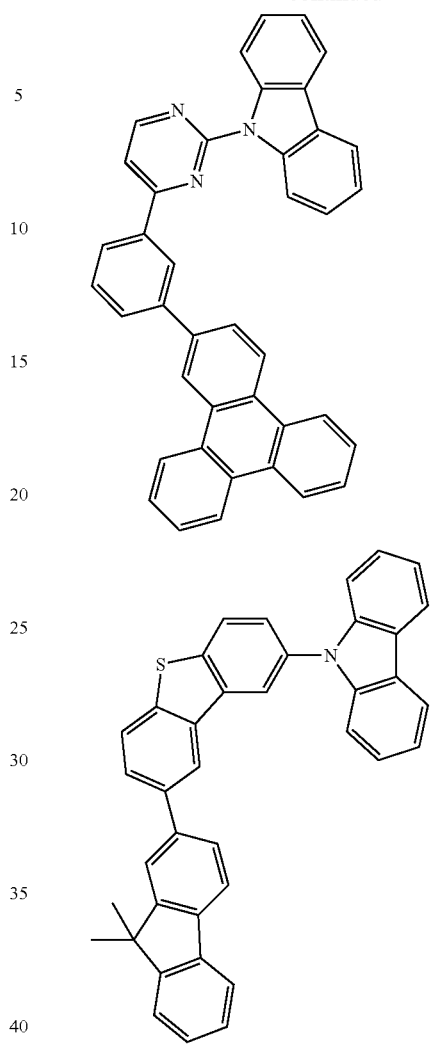
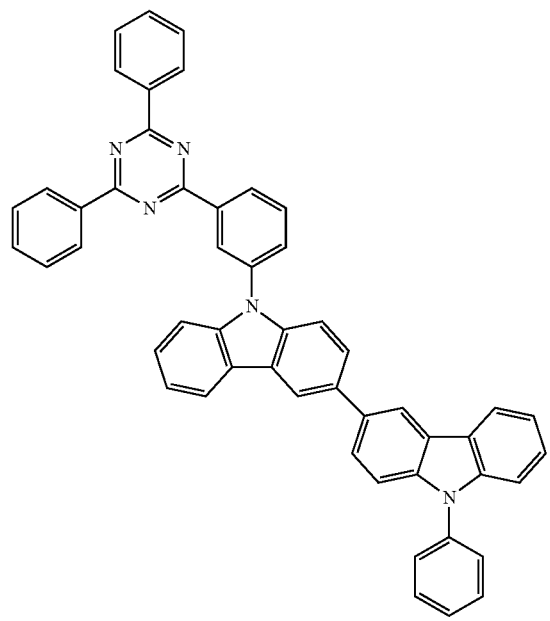
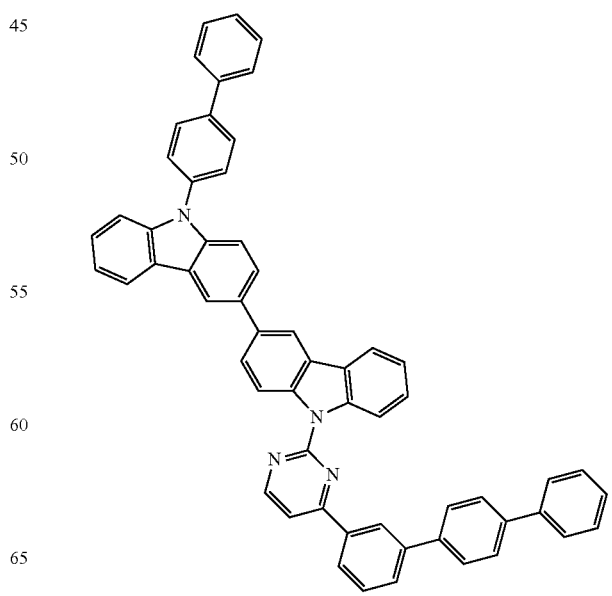

67
-continued
68
-continued
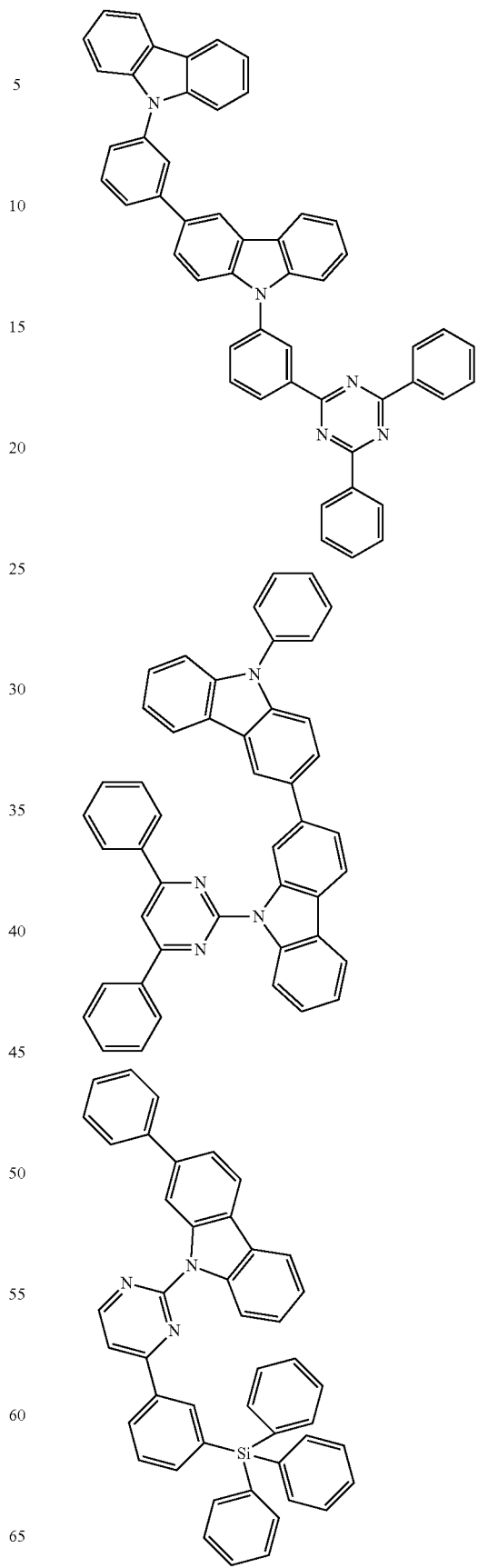

69
-continued
70
-continued
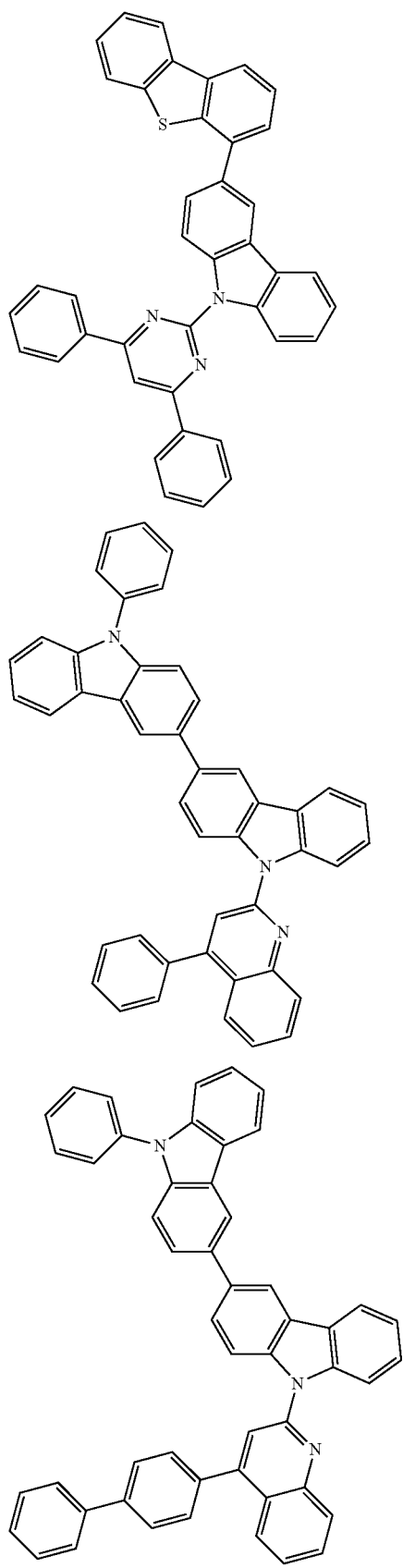
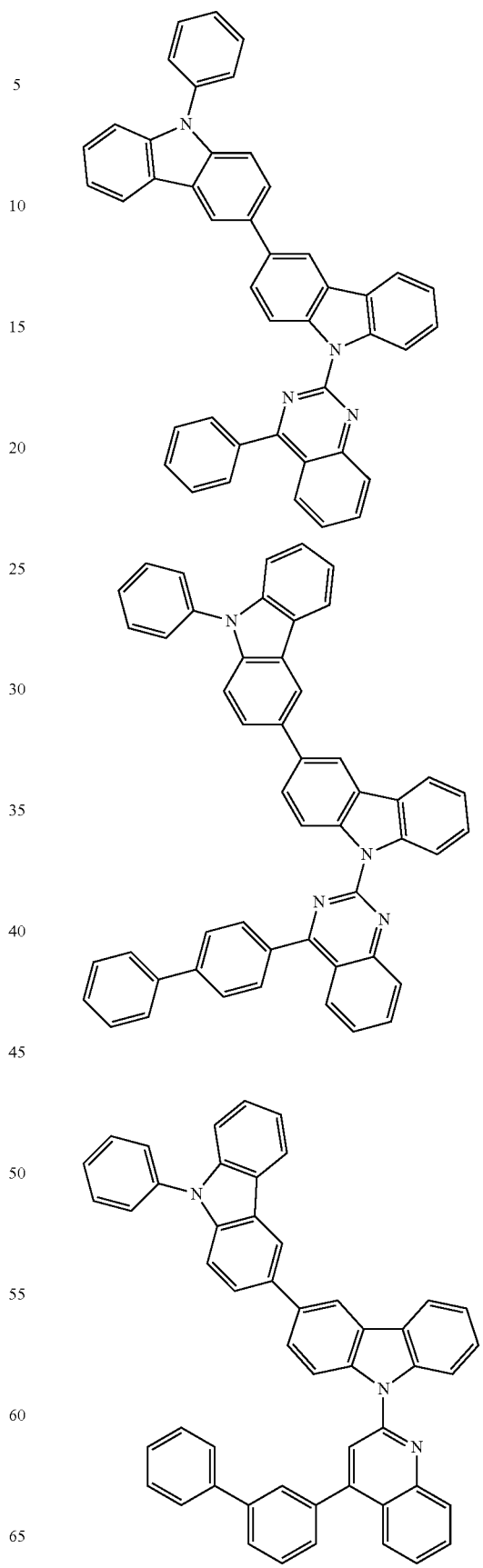

71
-continued
72
-continued
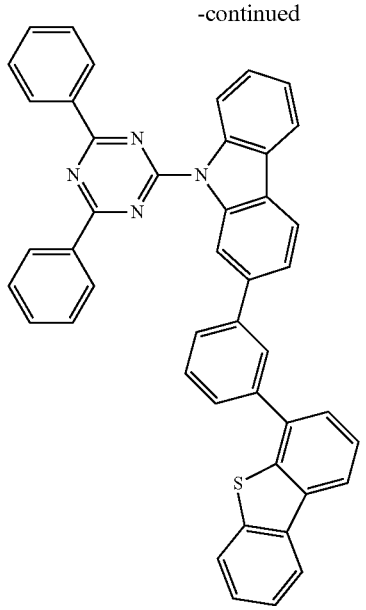
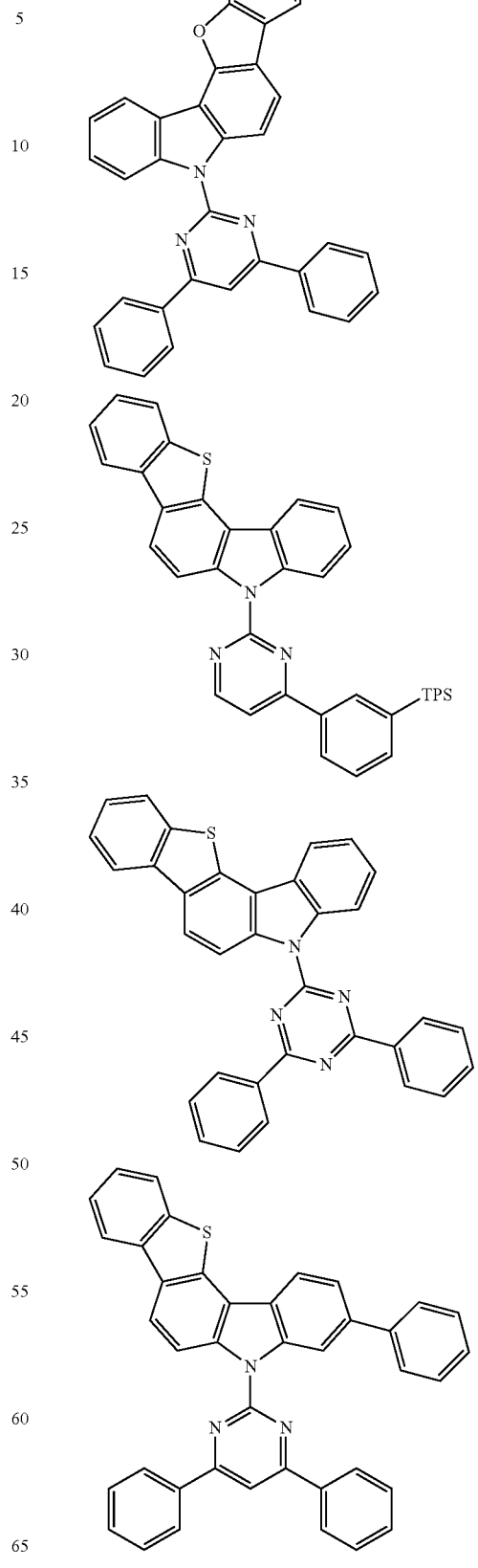

73
-continued
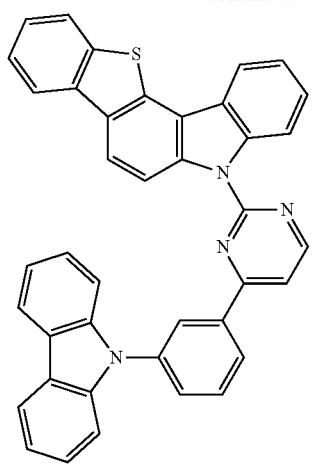
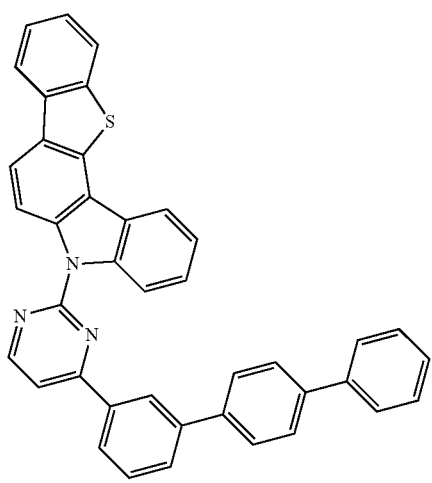
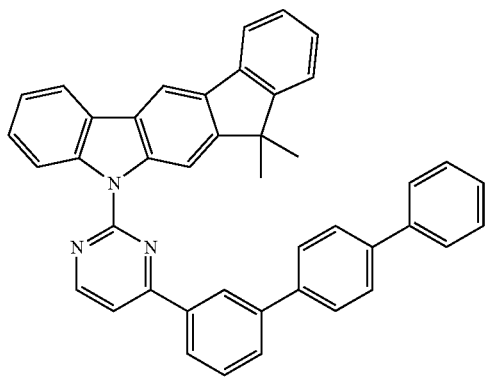
74
-continued
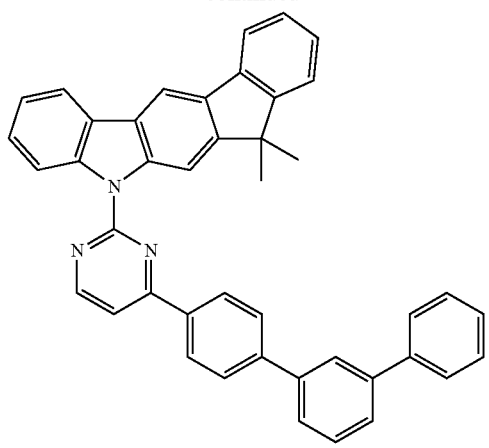
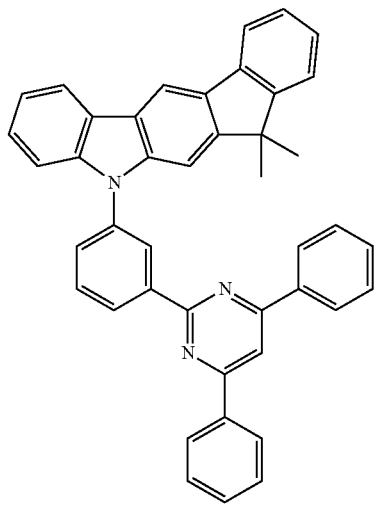
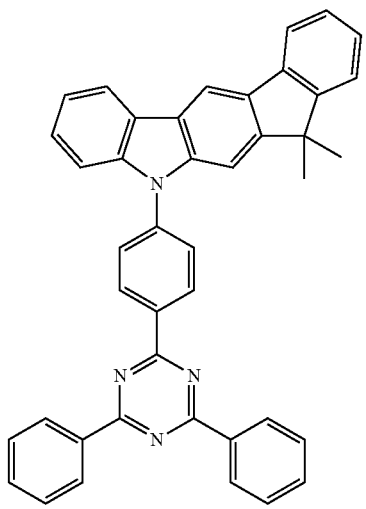

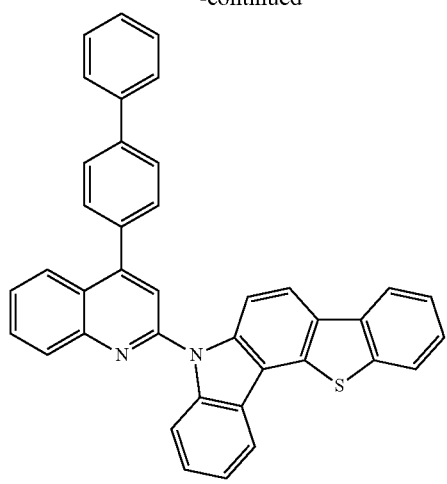
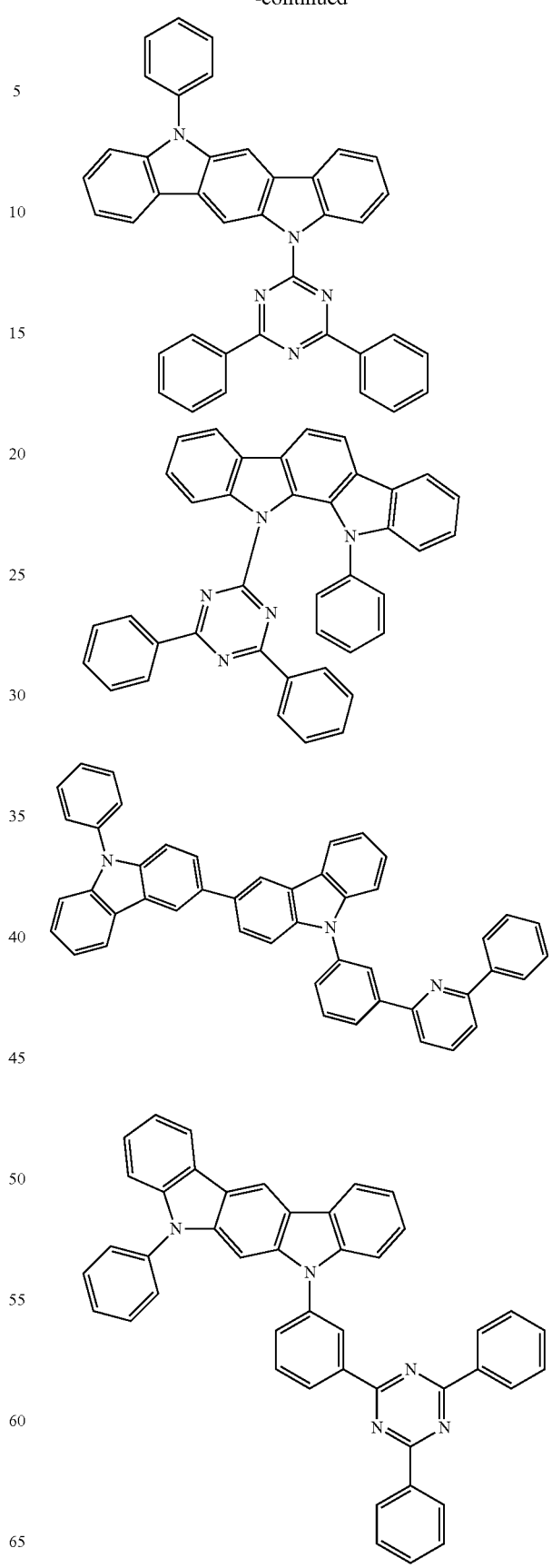

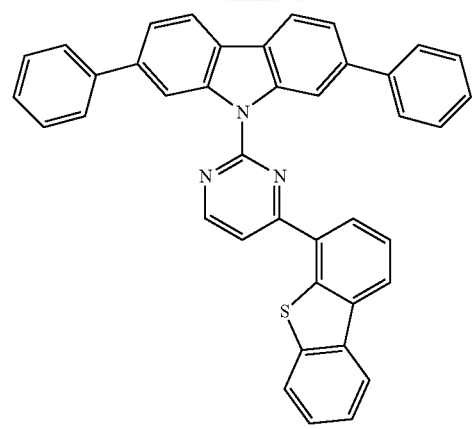
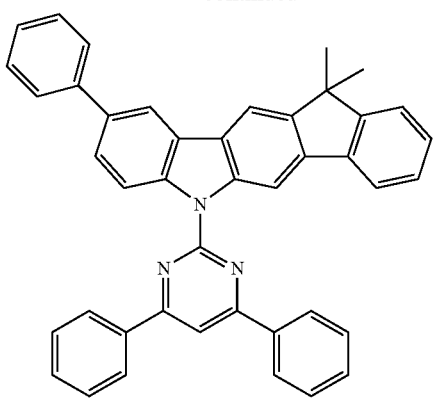

-continued

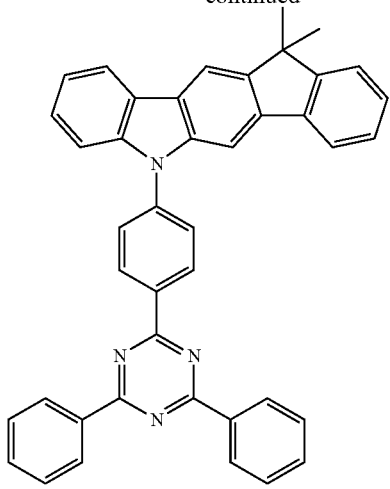

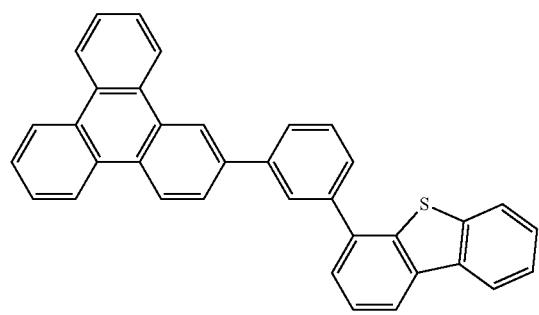

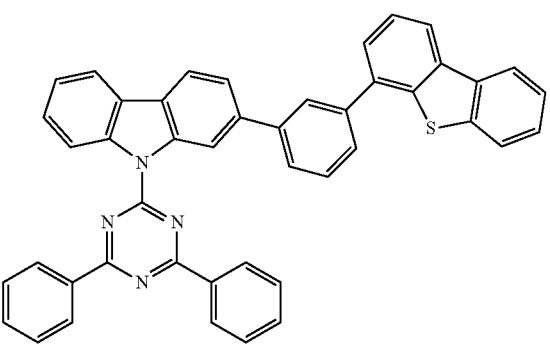

[wherein TPS represents a triphenylsilyl group]

The dopant comprised in the organic electroluminescent device according to the present invention is preferably at least one phosphorescent dopant. The dopant materials applied to the organic electroluminescent device according to the present invention are not limited, but may be preferably selected from metallated complex compounds of iridium, osmium, copper, and platinum, more preferably selected from ortho-metallated complex compounds of iridium, osmium, copper, and platinum, and even more preferably ortho-metallated iridium complex compounds.

The dopants comprised in the organic electroluminescent device of the present invention may be preferably selected from compounds represented by the following formulae 101 to 103.

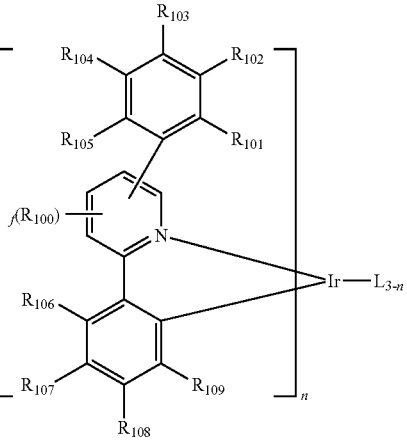

(101)

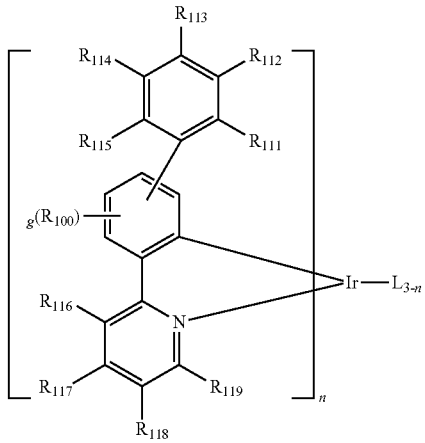

(102)

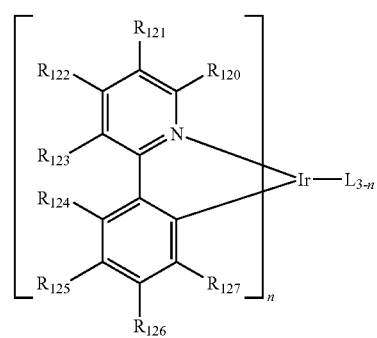

(103)

wherein L is selected from the following structures:

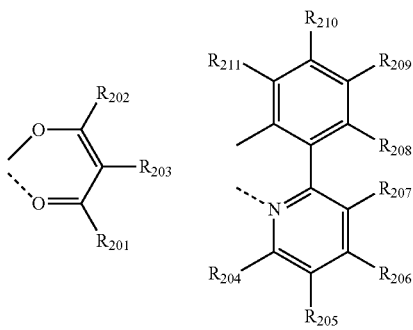

R_{100} represents hydrogen, a substituted or unsubstituted (C1-C30)alkyl, or a substituted or unsubstituted (C3-C30) cycloalkyl;

R_{101} to R_{109}, and R_{111} to R_{123} each independently represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a cyano, or a substituted or unsubstituted (C1-C30)alkoxy; adjacent substituents of R_{106} to R_{109} may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl; and adjacent substituents of R_{120} to R_{123} may be linked to each other to form a substituted or unsubstituted fused ring, e.g., quinoline unsubstituted or substituted with alkyl or aryl;

R_{124} to R_{127} each independently represent hydrogen, deuterium, a halogen, a substituted or unsubstituted (C1-C30) alkyl, or a substituted or unsubstituted (C6-C30)aryl; and adjacent substituents of R_{124} to R_{127} may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

R_{201} to R_{211} each independently represent hydrogen, deuterium, a halogen, a (C1-C30)alkyl unsubstituted or substituted with a halogen(s), a substituted or unsubstituted (C3-C30)cycloalkyl, or a substituted or unsubstituted (C6-C30) aryl, and adjacent substituents of R_{205} to R_{211} may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

f and g each independently represent an integer of 1 to 3; where f or g is an integer of 2 or more, each of R_{100} may be the same or different; and n represents an integer of 1 to 3.

Specifically, the dopant compounds include the following:

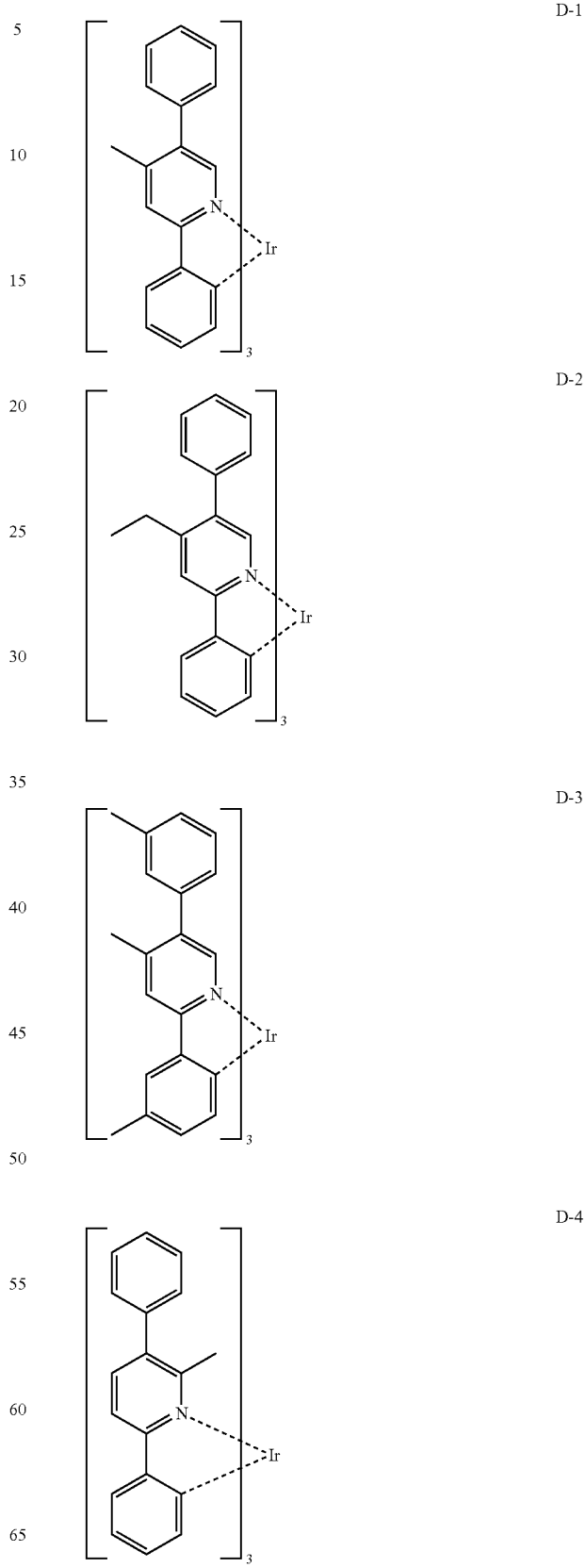

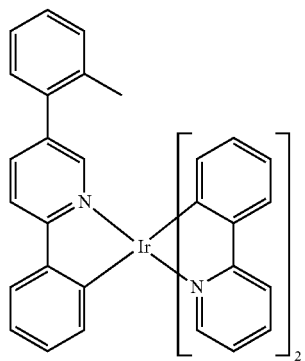
D-5
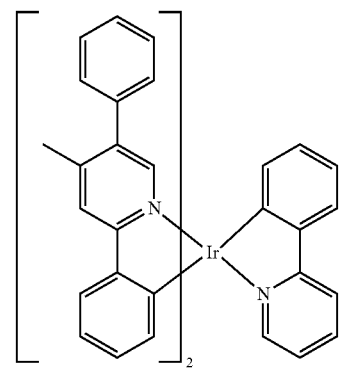
D-9
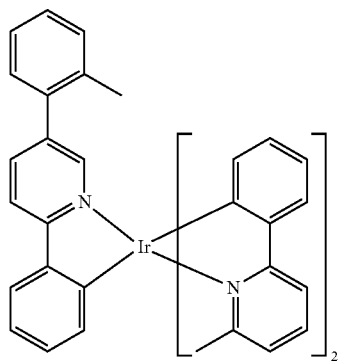
D-6
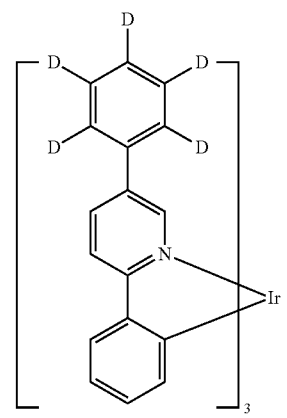
D-10
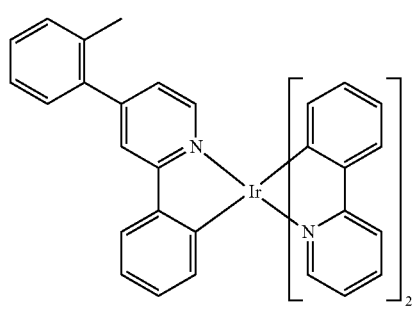
D-7
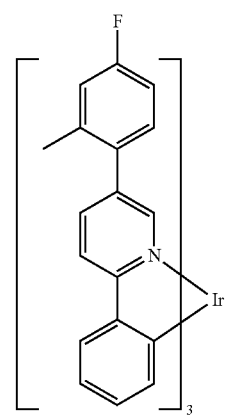
D-11
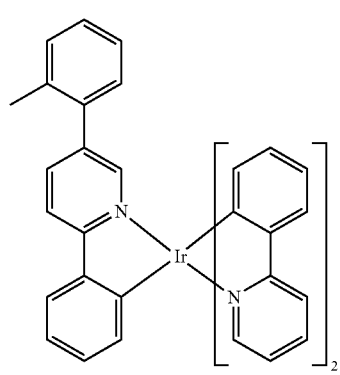
D-8
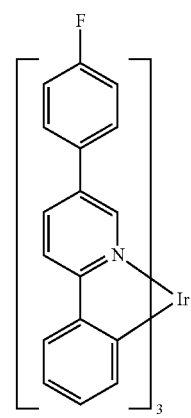
D-12

D-13 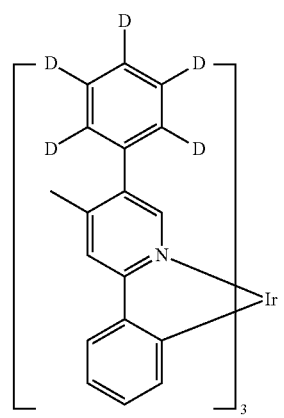
D-14 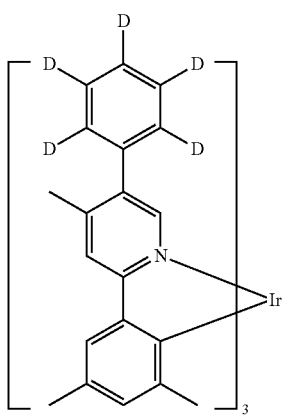
D-15 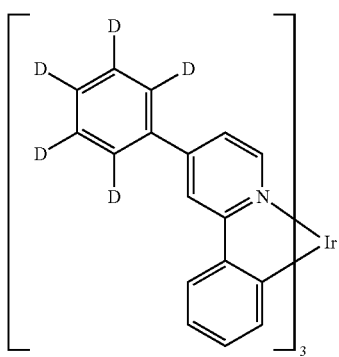
D-16 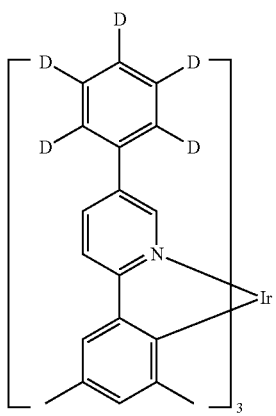
D-17 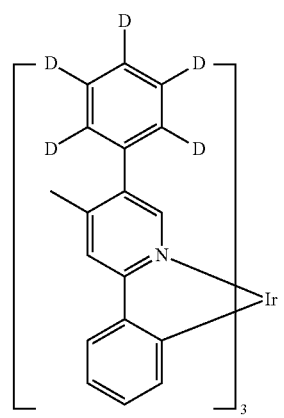
D-18 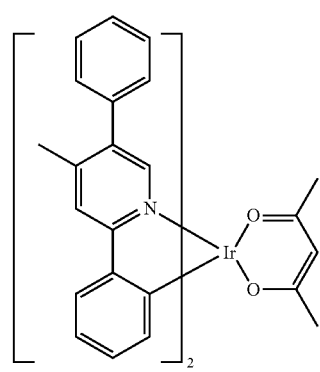
D-19 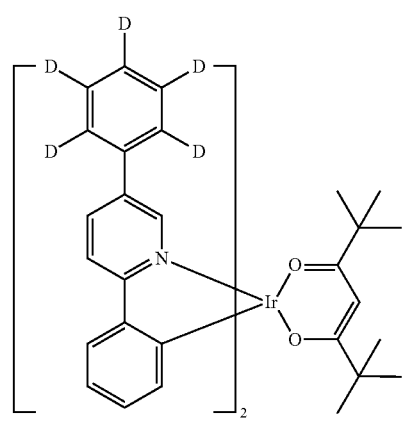
D-20 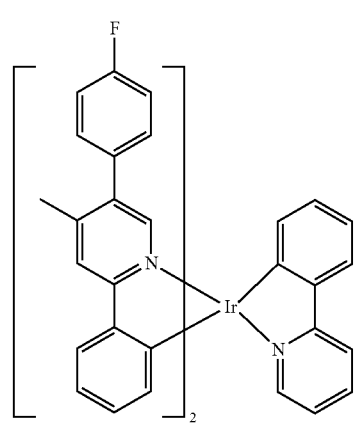

D-21
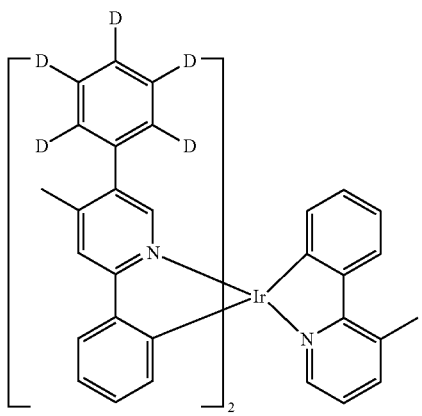
D-22
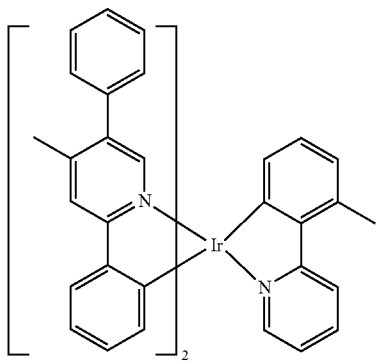
D-23
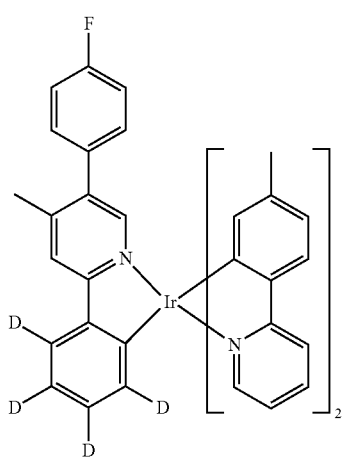
D-24
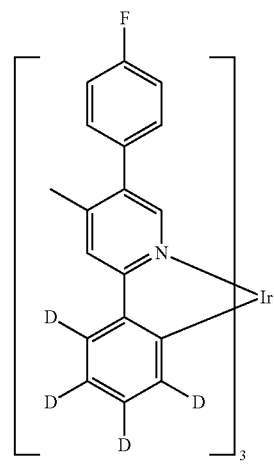
D-25
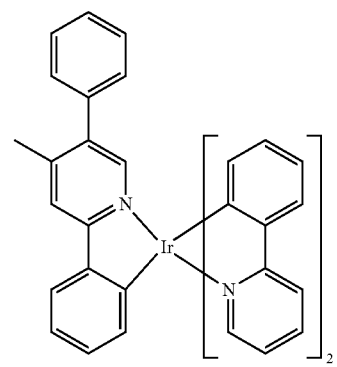
D-26
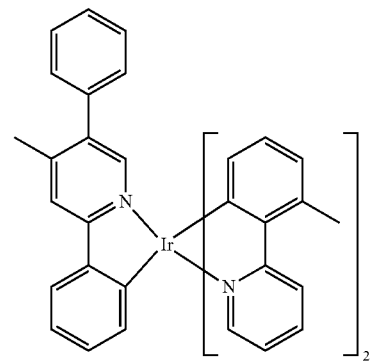
D-27
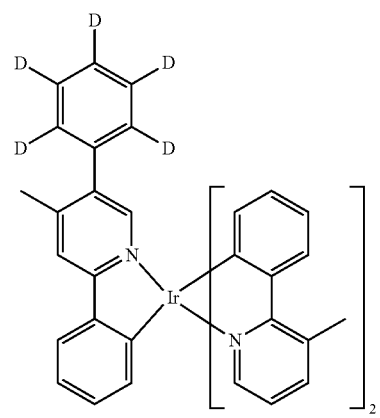

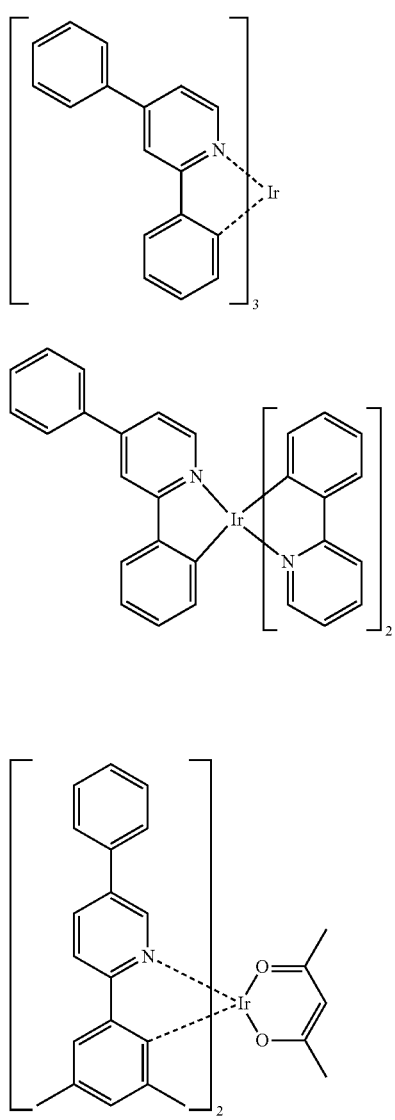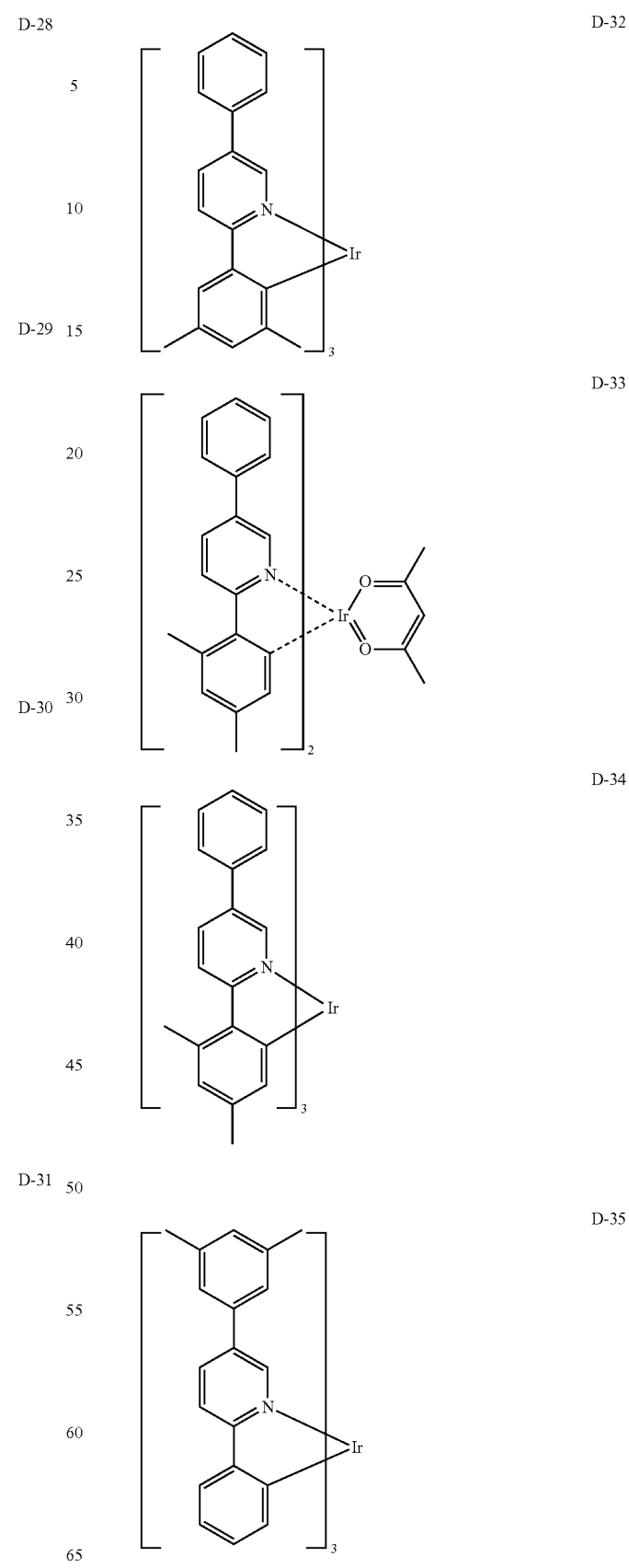

-continued
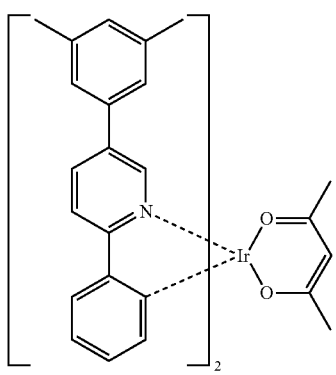
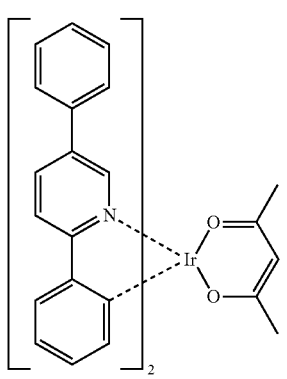
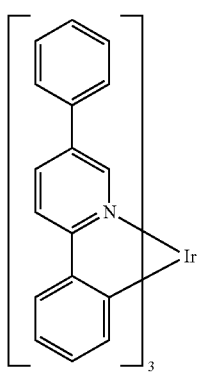
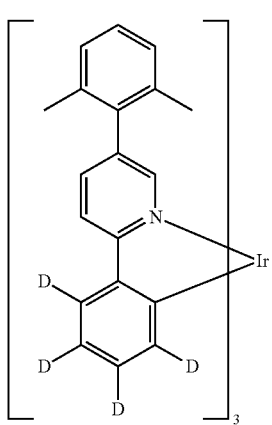
-continued
D-36
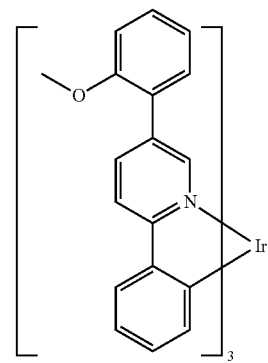
D-37
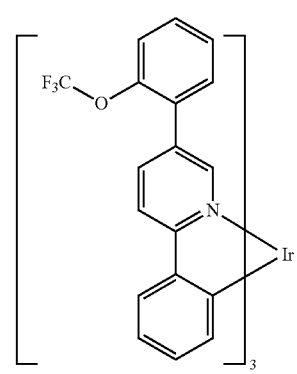
D-38
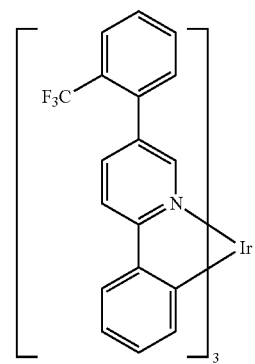
D-39
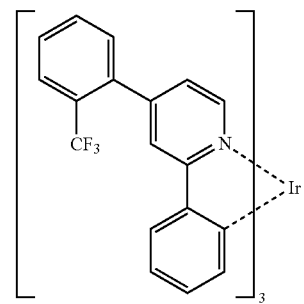
D-40
D-41
D-42
D-43

-continued
D-44
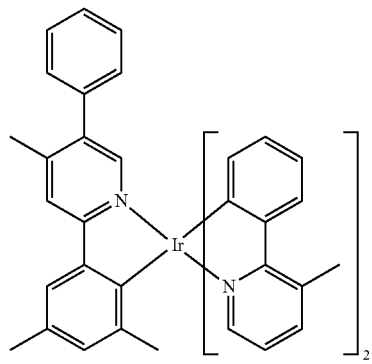
D-45
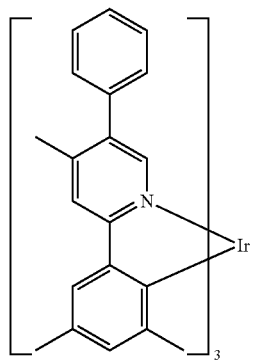
D-46
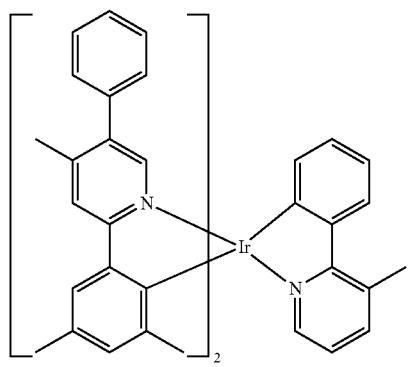
D-47
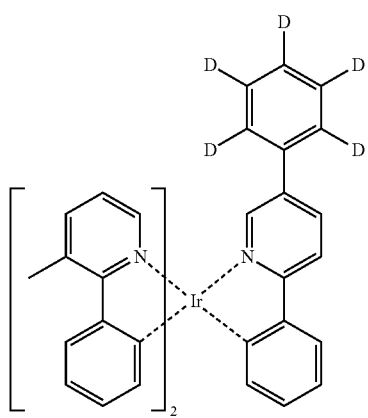
-continued
D-48
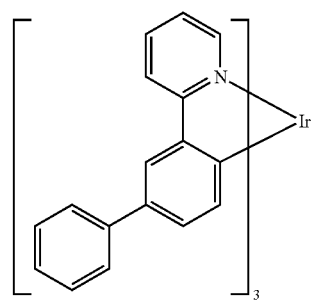
D-49
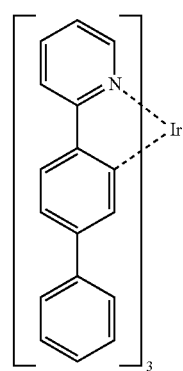
D-50
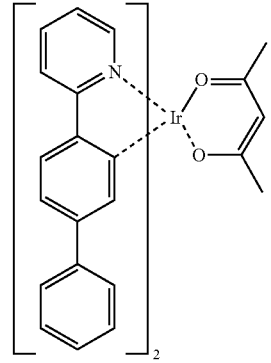
D-51
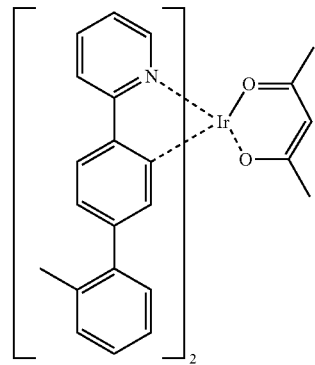

D-52 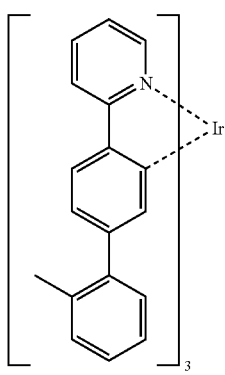
D-53 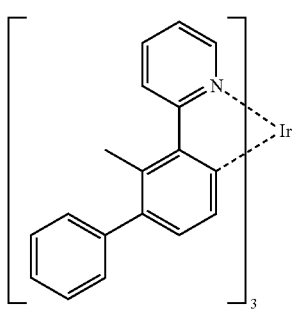
D-54 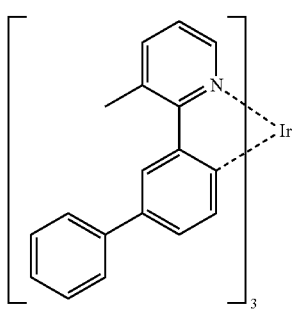
D-55 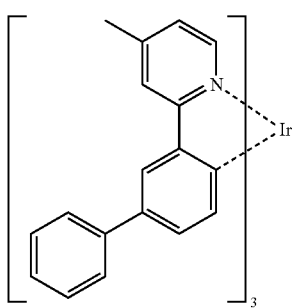
D-56 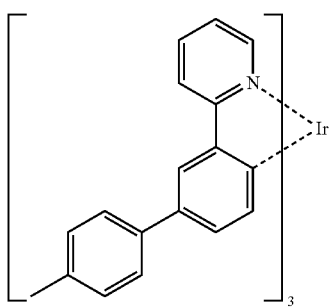
D-57 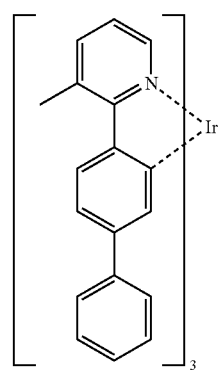
D-58 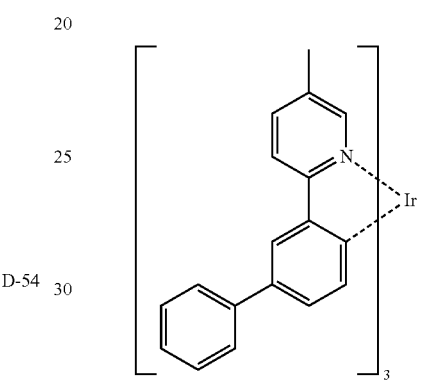
D-59 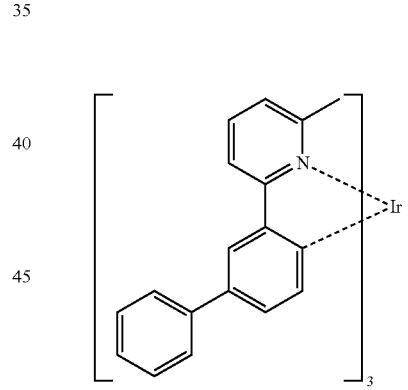
D-60 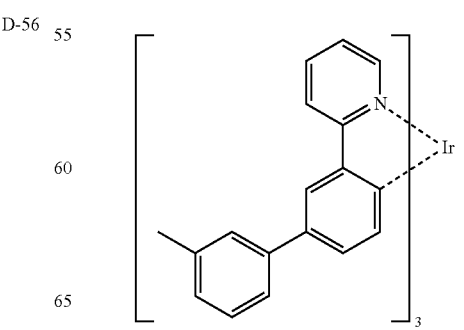

D-61 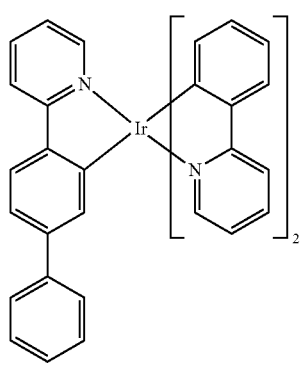
D-65 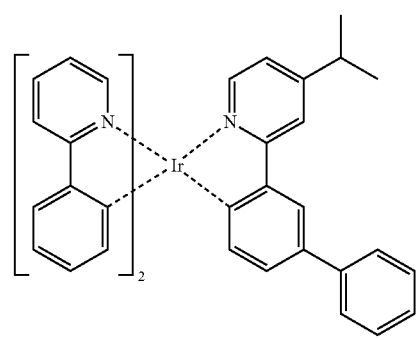
D-62 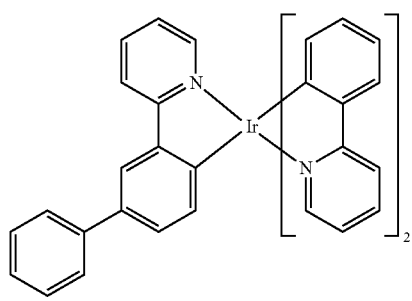
D-66 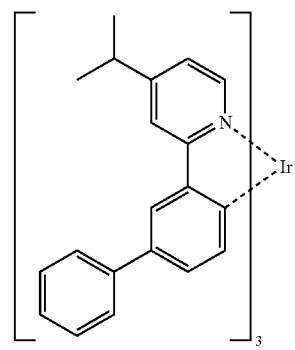
D-63 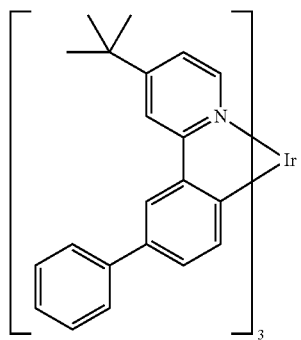
D-67 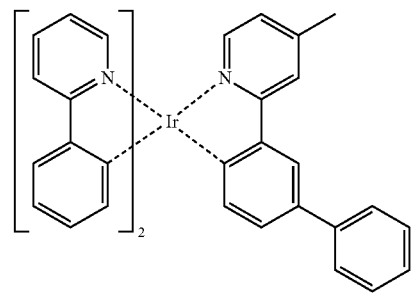
D-64 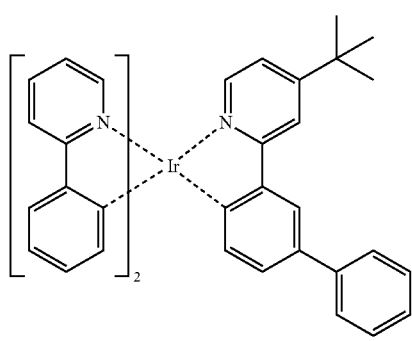
D-68 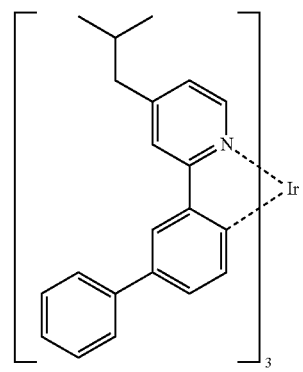

-continued
D-69
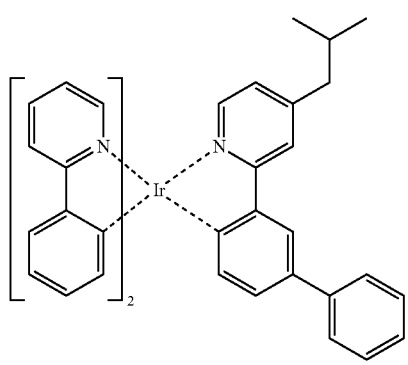
D-70
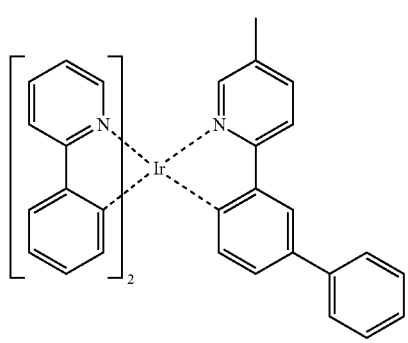
D-71
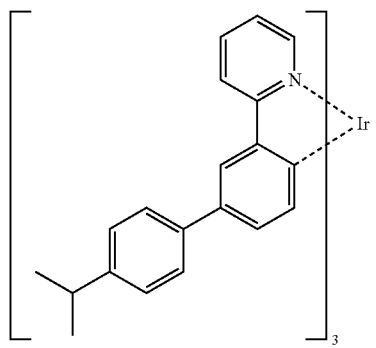
D-72
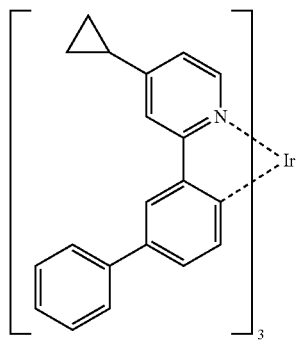
-continued
D-73
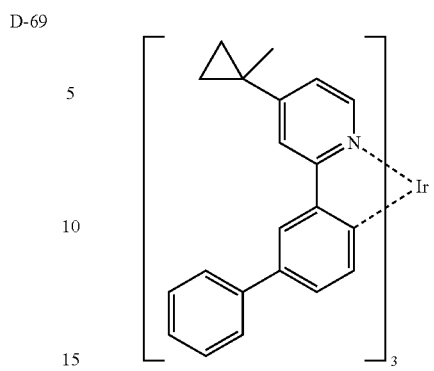
D-74
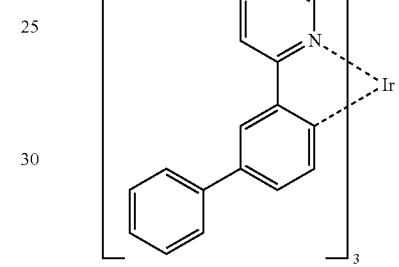
D-75
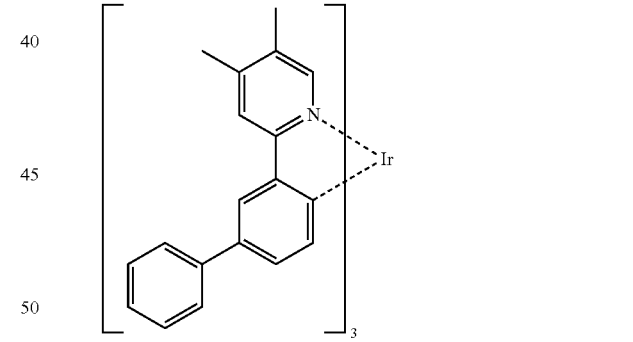
D-76
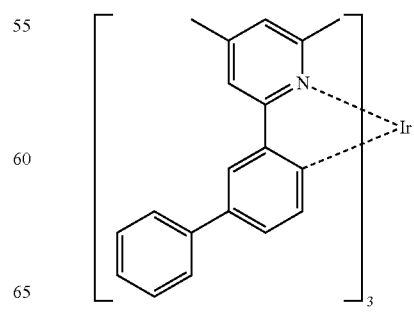

D-77 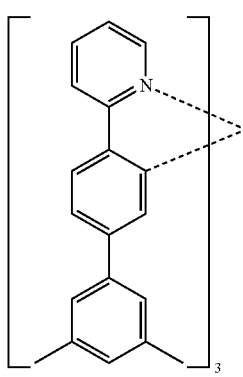
D-78 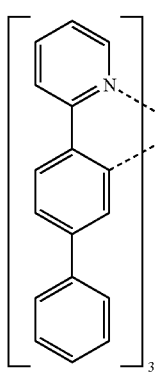
D-79 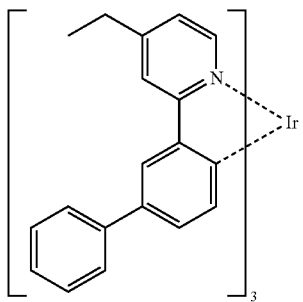
D-80 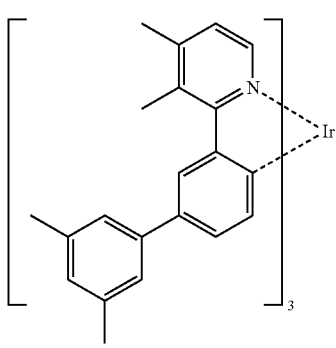
D-81 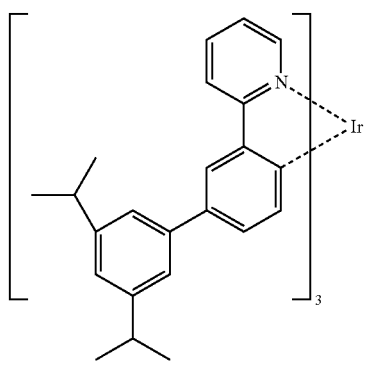
D-82 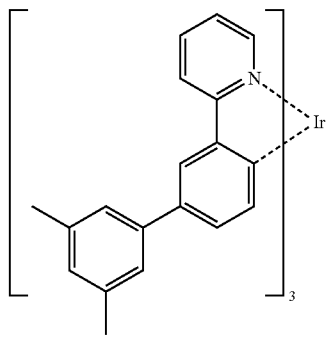
D-83 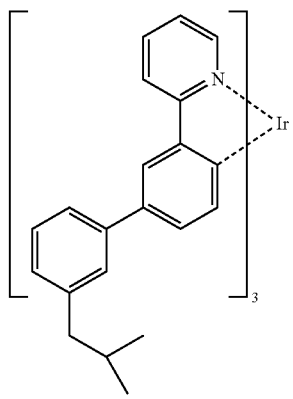
D-84 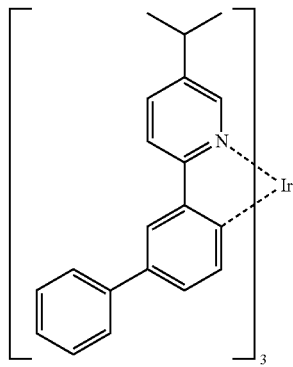

D-85
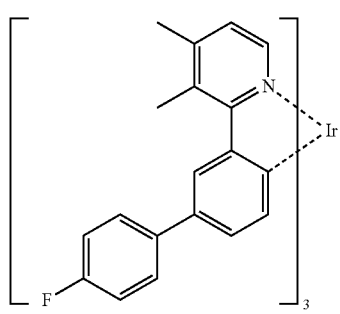
D-86
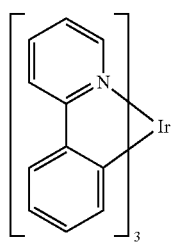
D-87
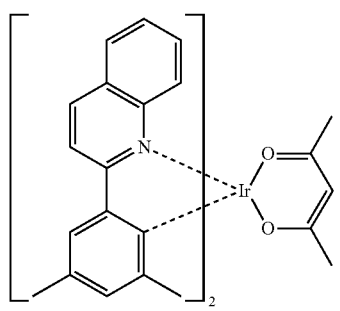
D-88
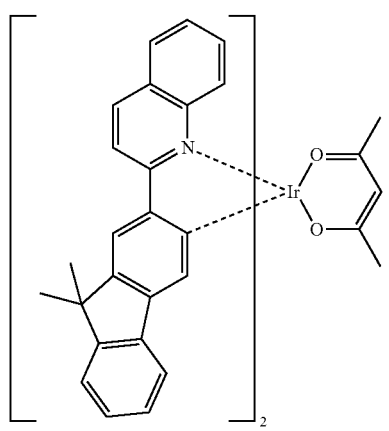
D-89
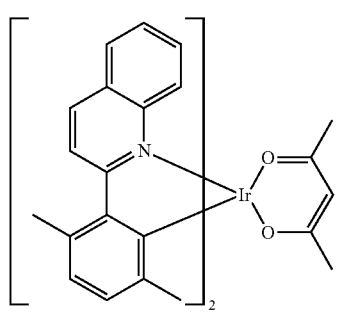
D-90
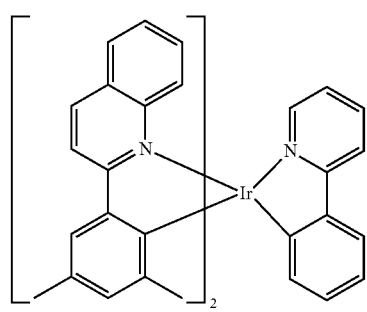
D-91
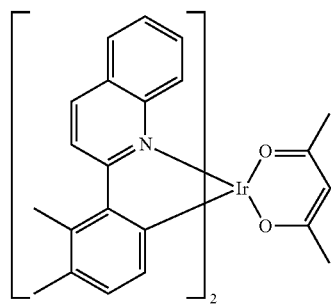
D-92
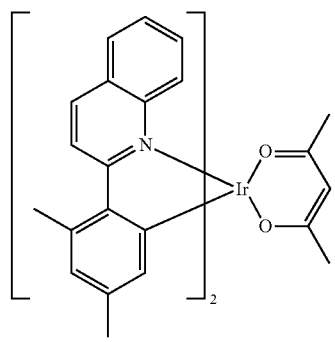
D-93
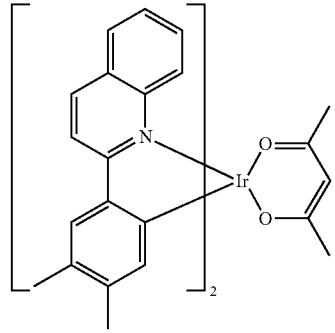

D-94
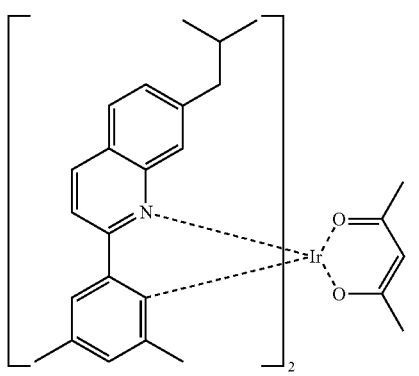
D-95
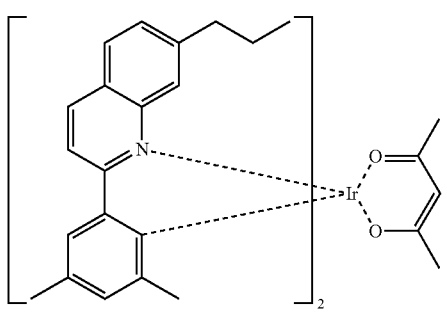
D-96
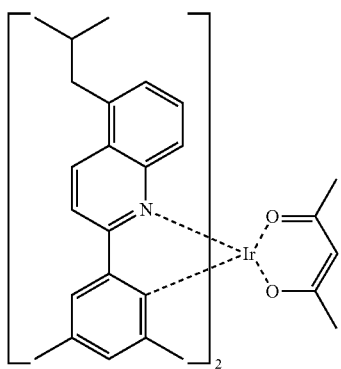
D-97
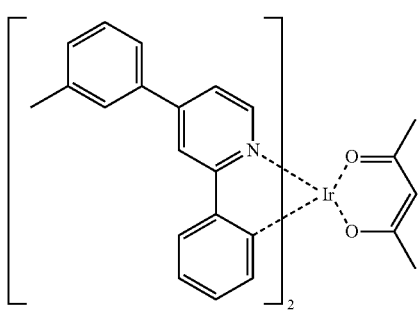
D-98
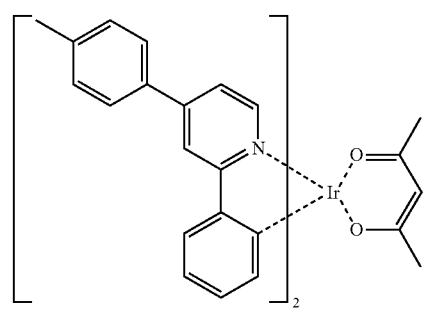
D-99
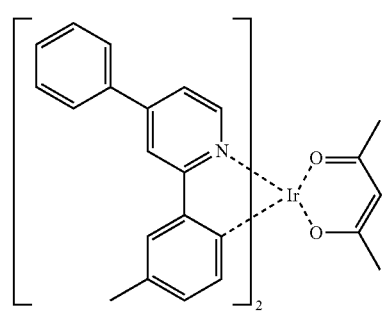
D-100
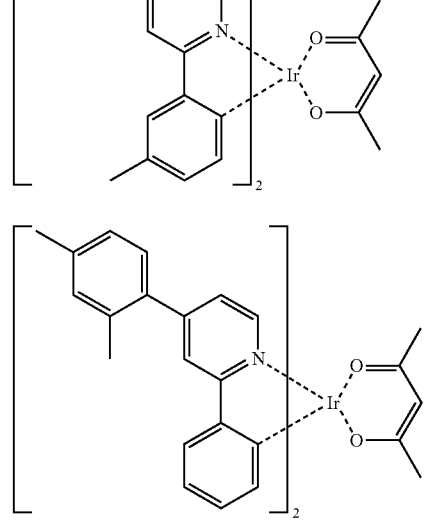
D-101
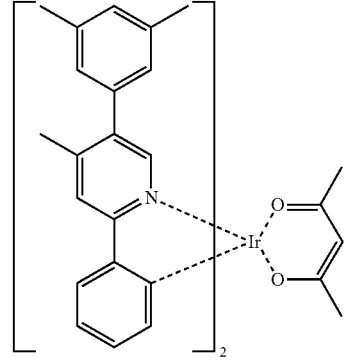
D-102
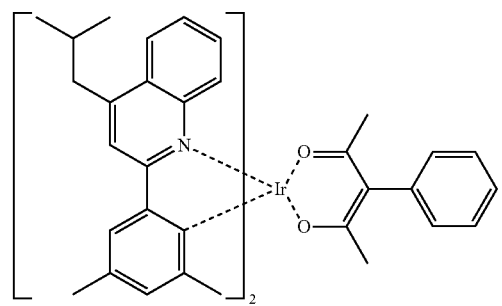

D-103
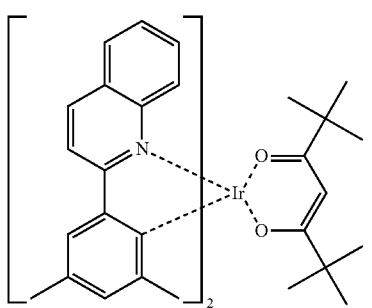
D-104
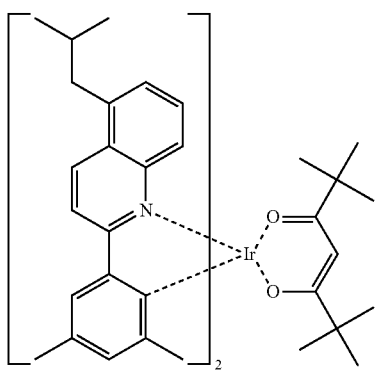
D-105
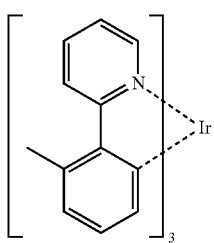
D-106
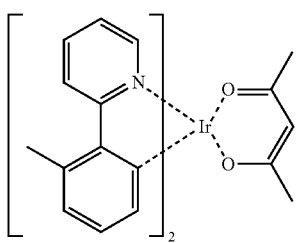
D-107
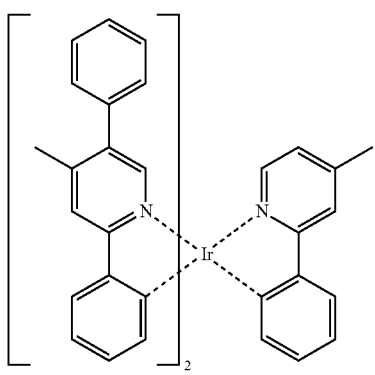
D-108
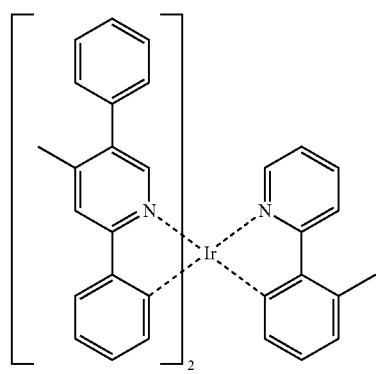
D-109
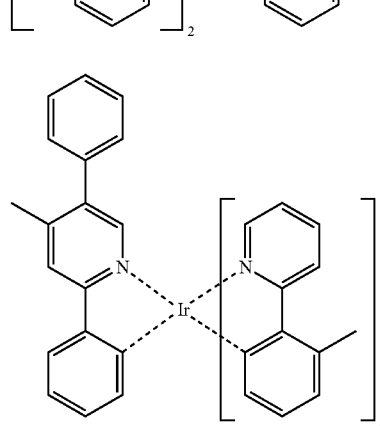
D-110
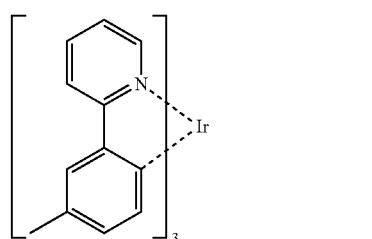
D-111
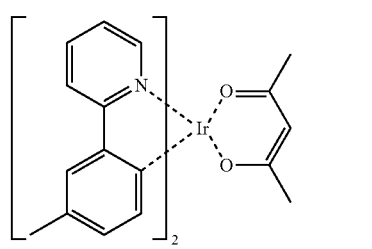
D-112
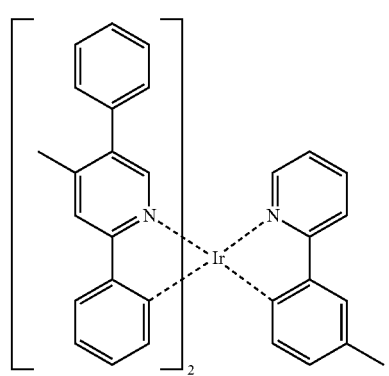

D-113
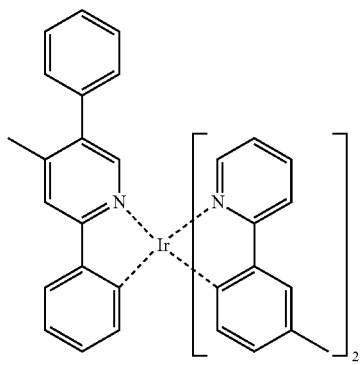
D-114
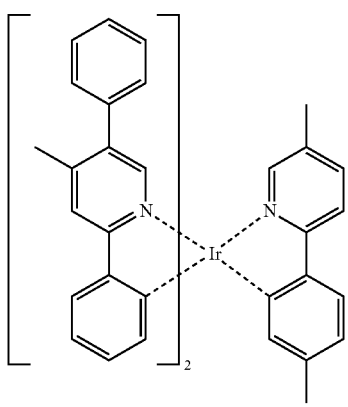
D-115
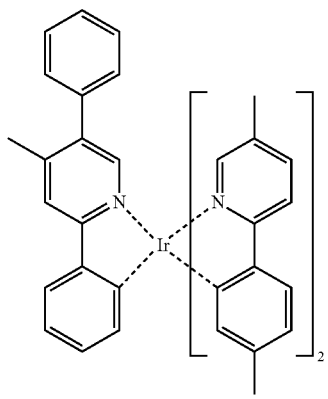
D-116
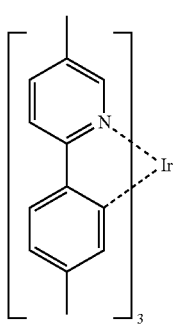
D-117
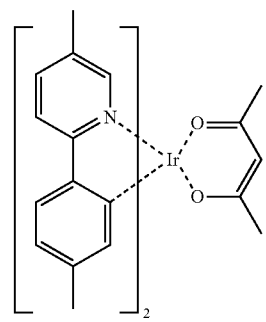
D-118
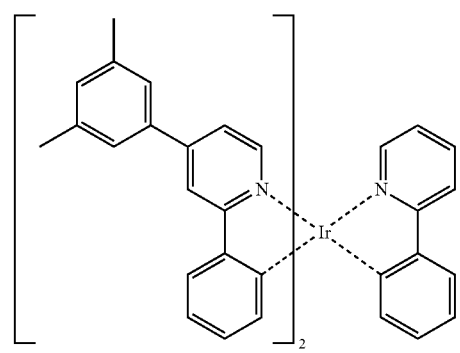
D-119
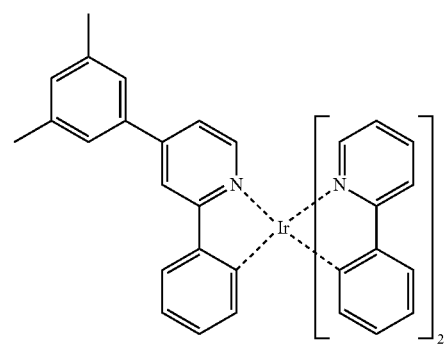
D-120
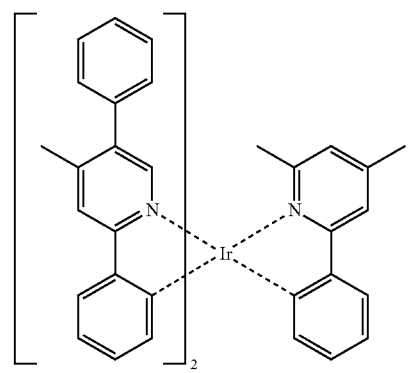

D-121 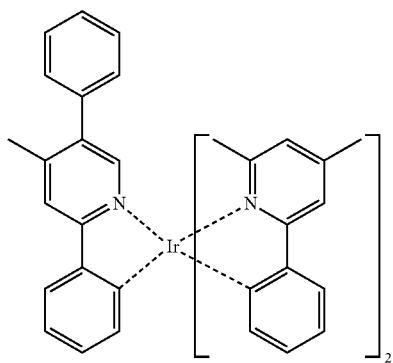
D-125 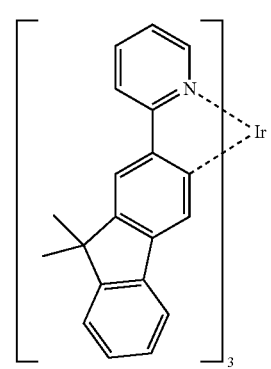
D-122 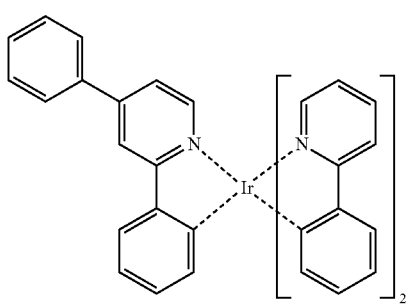
D-126 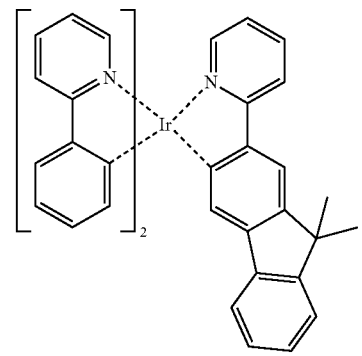
D-123 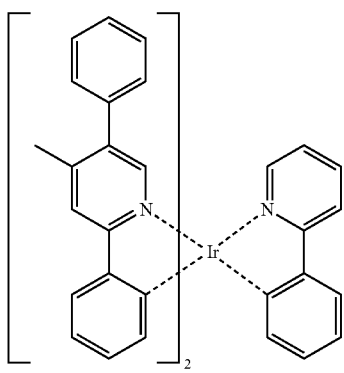
D-127 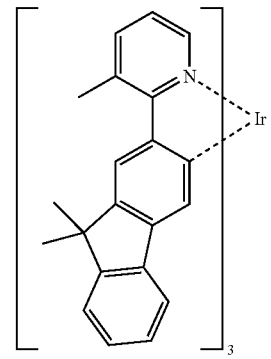
D-124 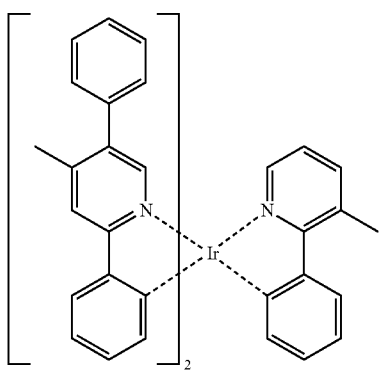
D-128 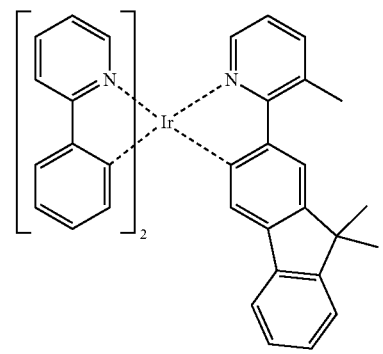

D-129 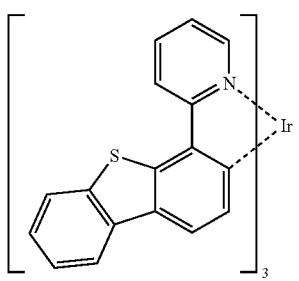
D-130 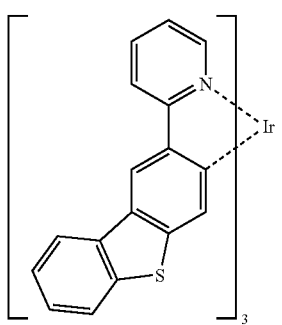
D-131 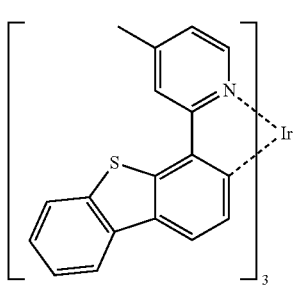
D-132 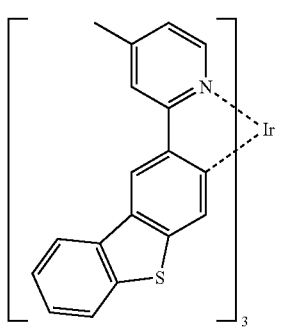
D-133 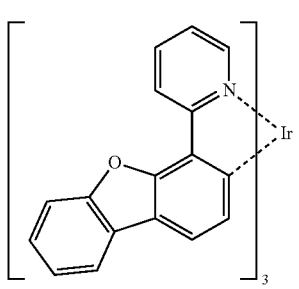
D-134 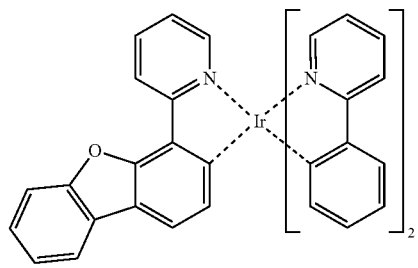
D-135 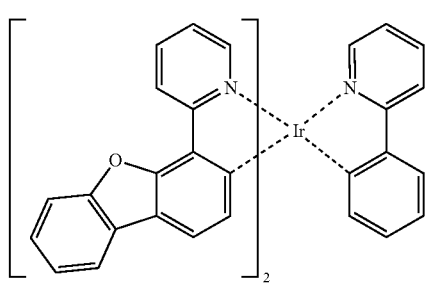
D-136 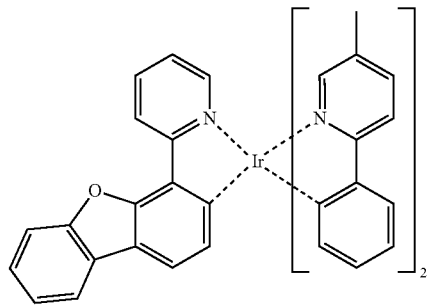
D-137 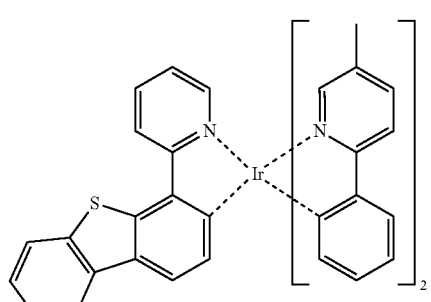
D-138 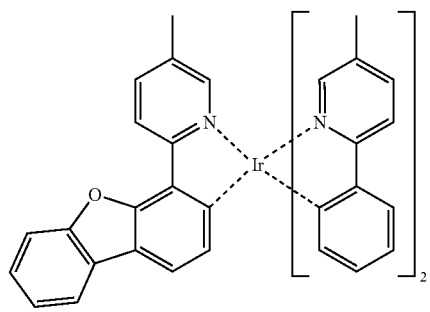

D-139
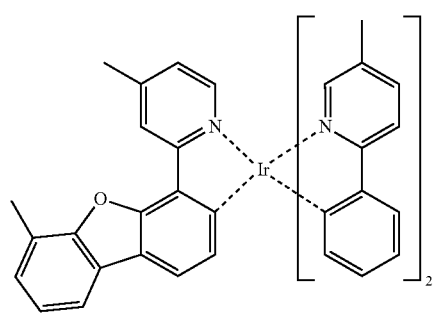
D-140
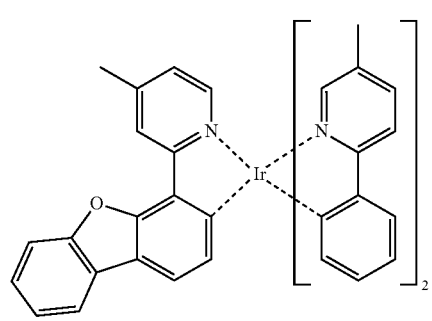
D-141
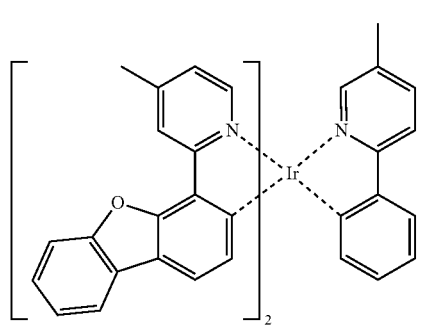
D-142
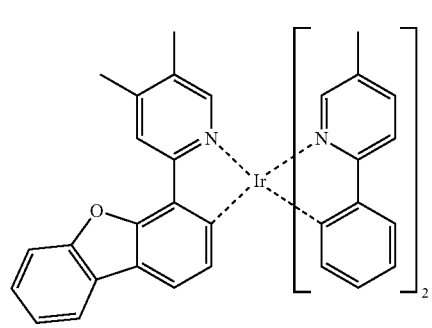
D-143
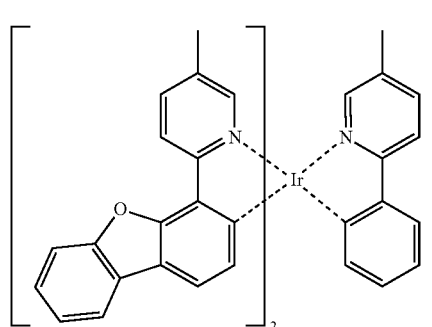
D-144
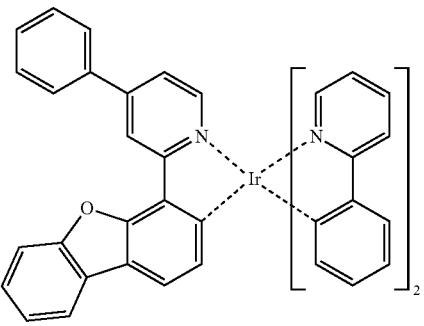
D-145
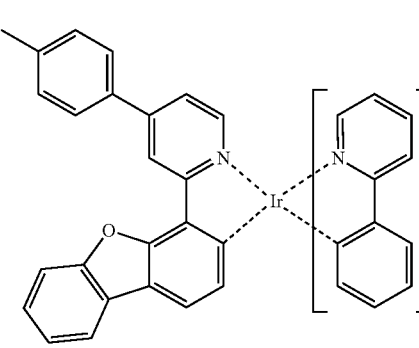
D-146
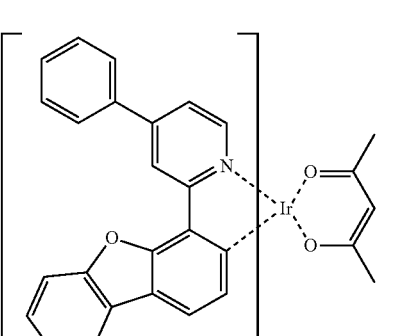
D-147
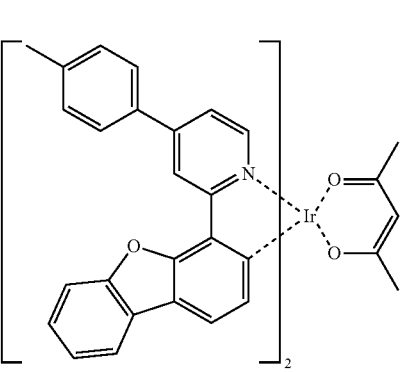

D-148
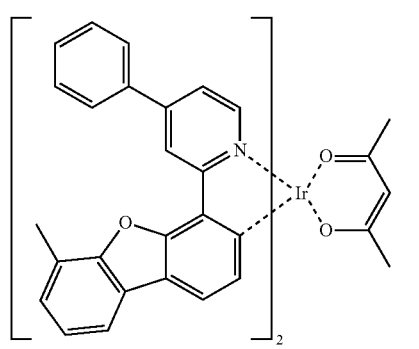
D-149
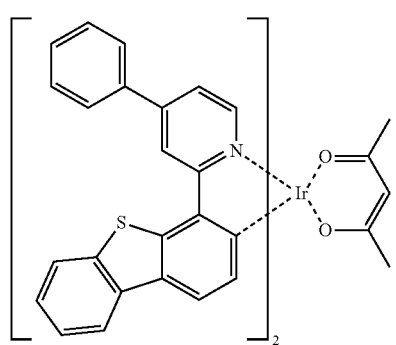
D-150
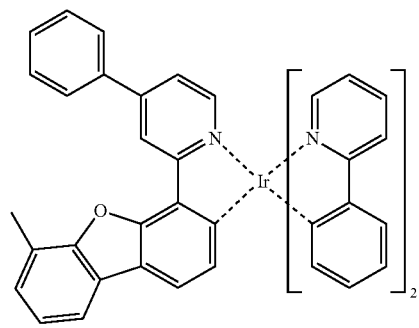
D-151
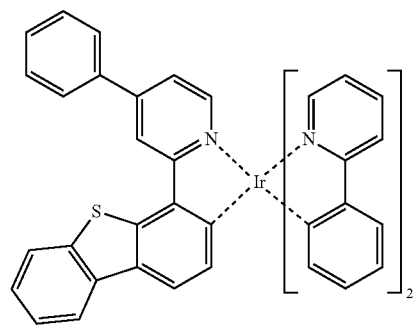
D-152
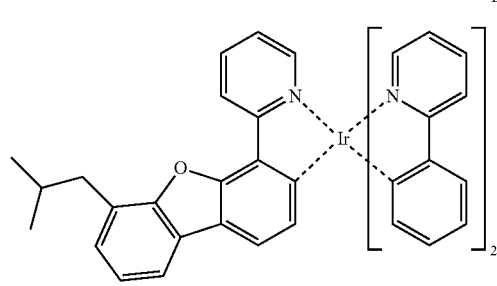
D-153
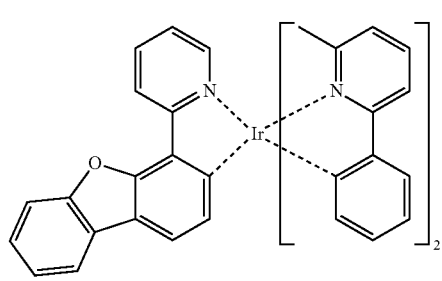
D-154
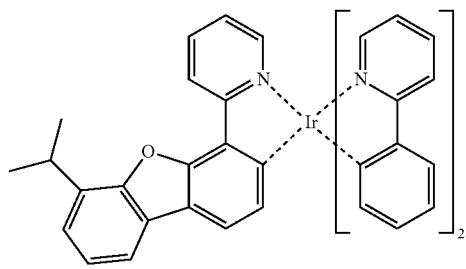
D-155
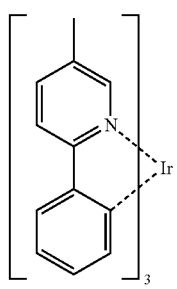
D-156
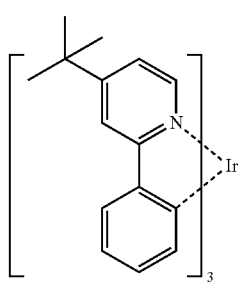
D-157
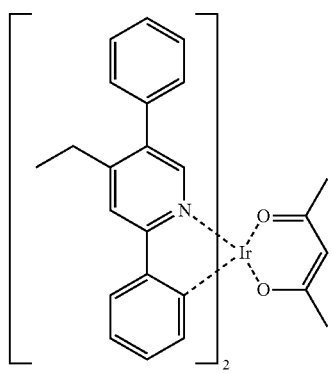

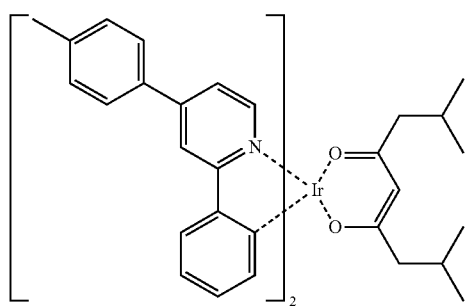
D-158
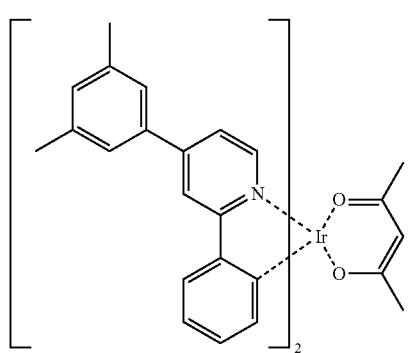
D-159
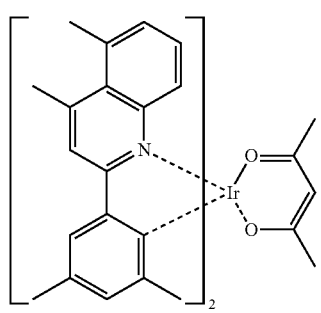
D-160
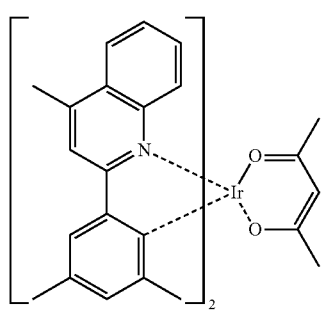
D-161
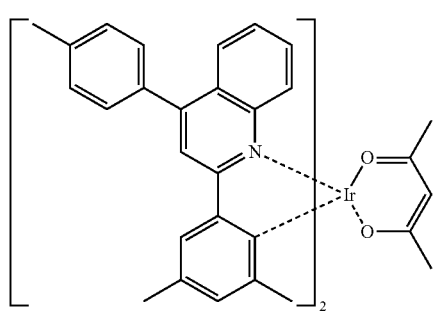
D-162
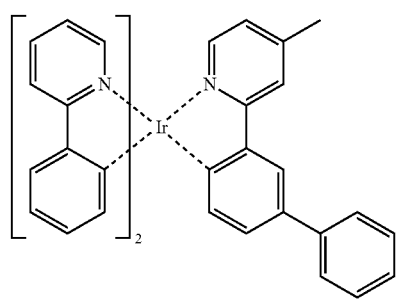
D-163
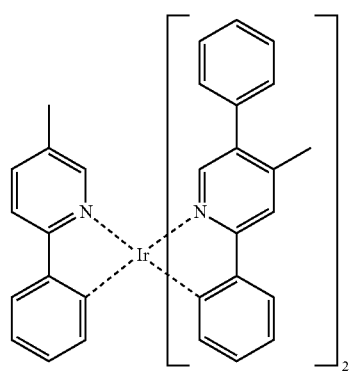
D-164
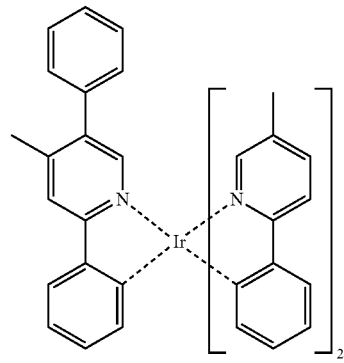
D-165
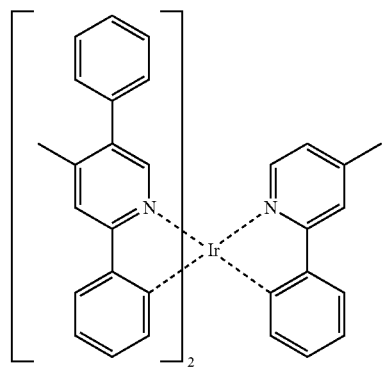
D-166

-continued
D-167
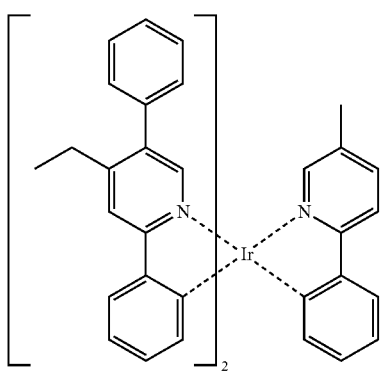
D-168
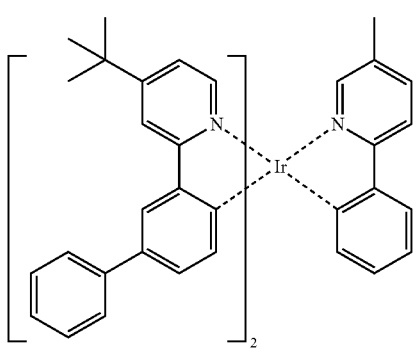
D-169
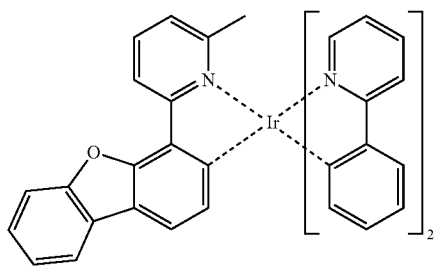
D-170
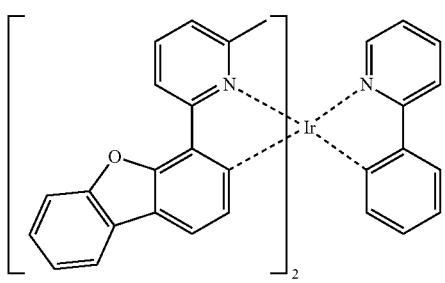
D-171
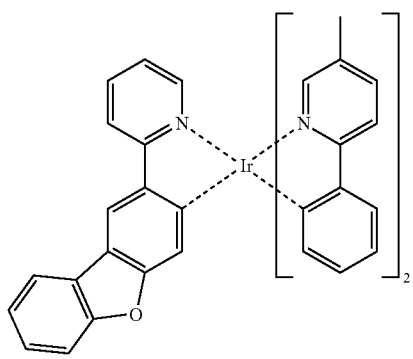
-continued
D-172
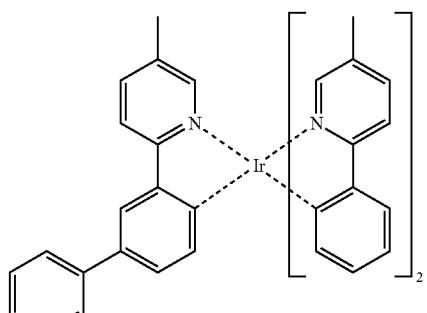
D-173
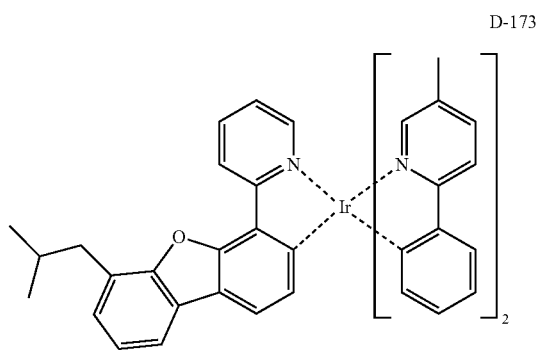
D-174
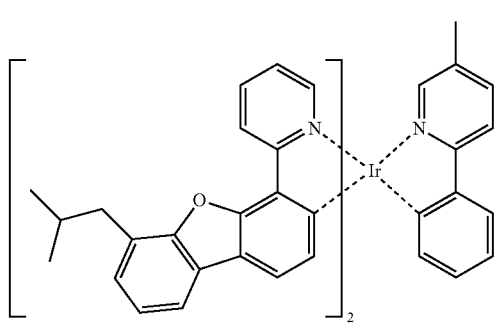
D-175
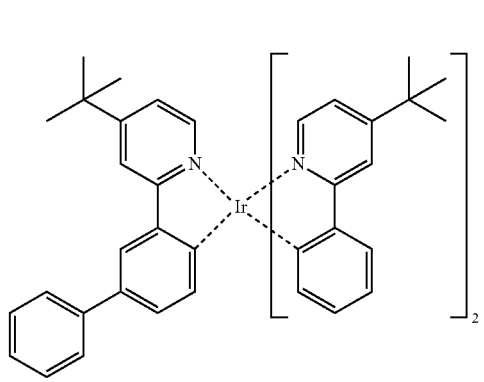

D-176
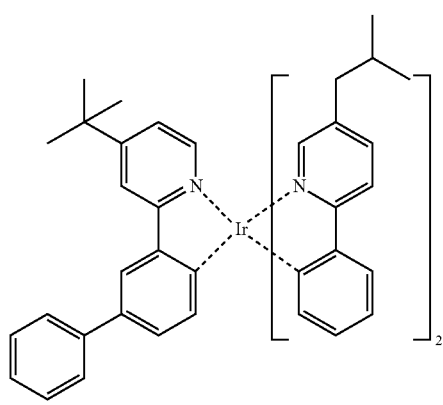
D-177
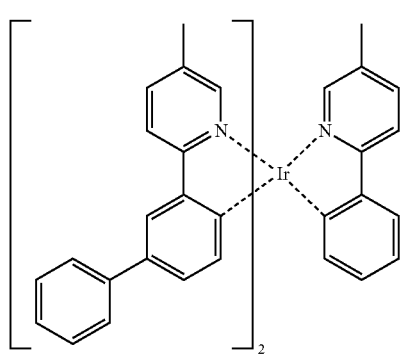
D-178
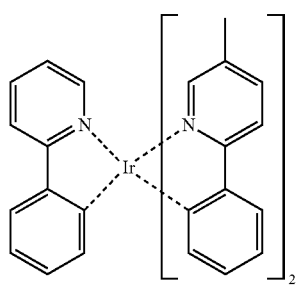
D-179
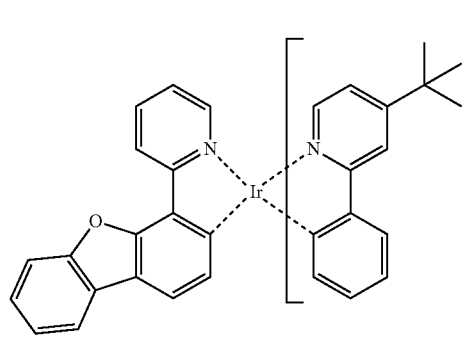
D-180
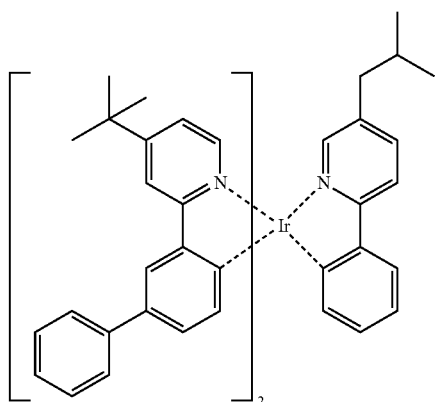
D-181
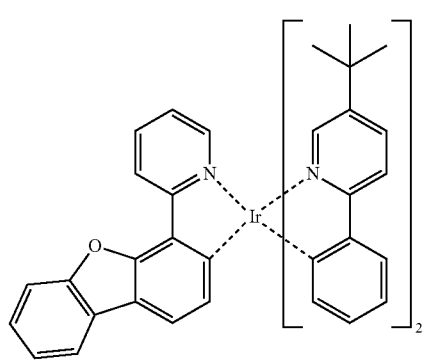
D-182
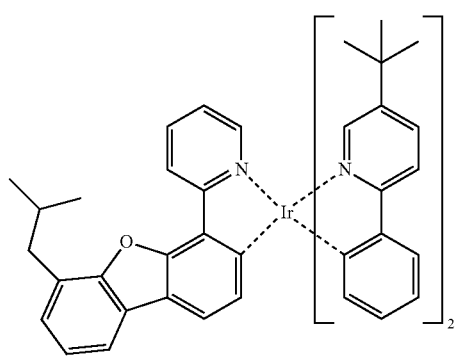
D-183
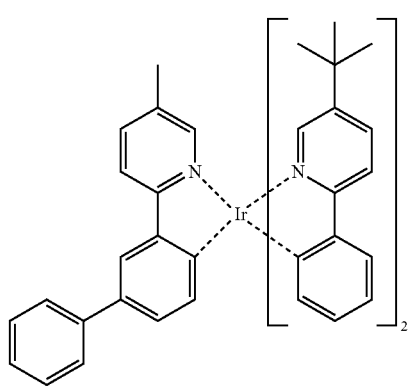

-continued
D-184
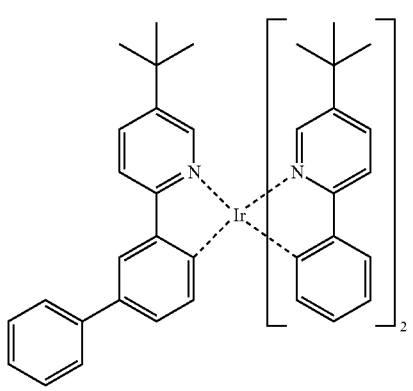
D-185
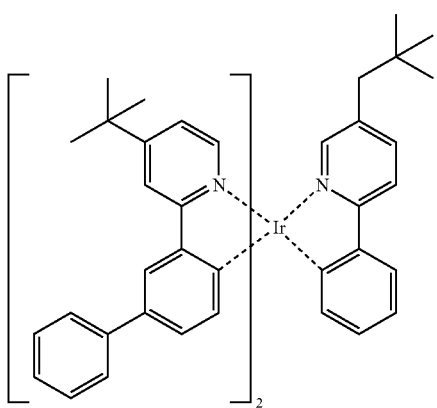
D-186
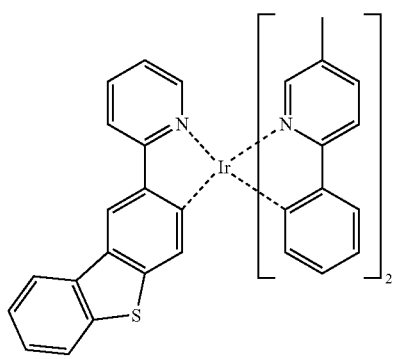
D-187
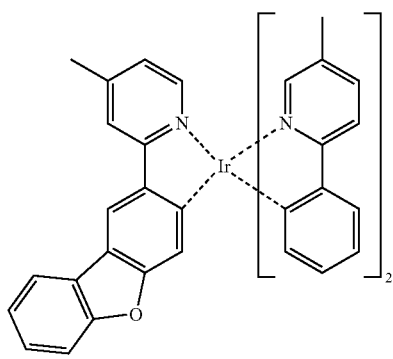
-continued
D-188
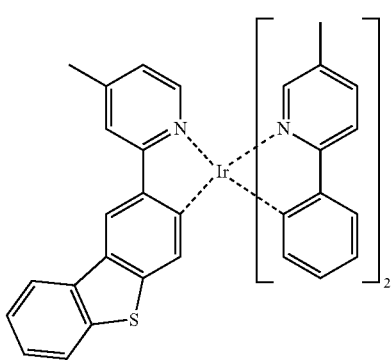
D-189
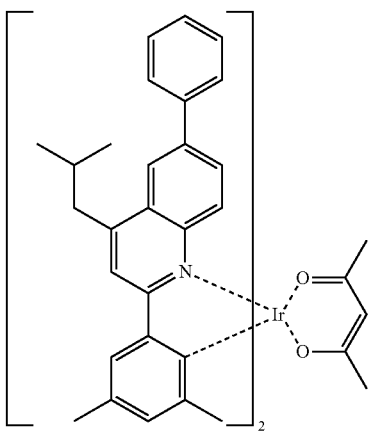
D-190
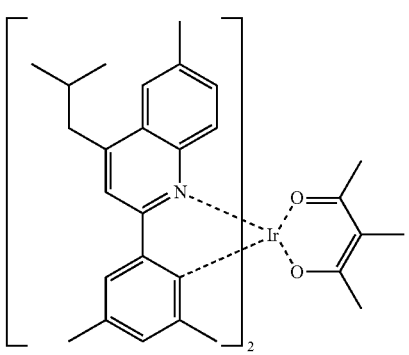
D-191
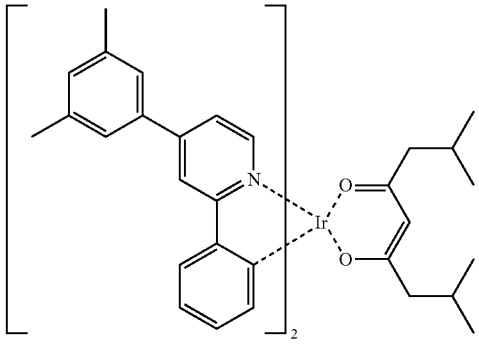

-continued

D-192
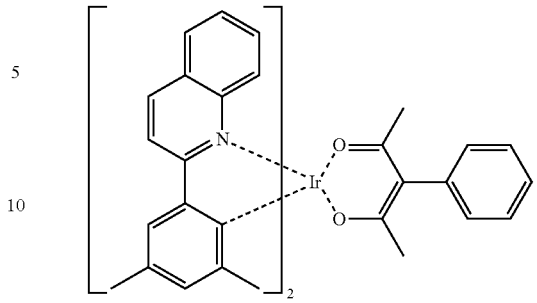

D-193
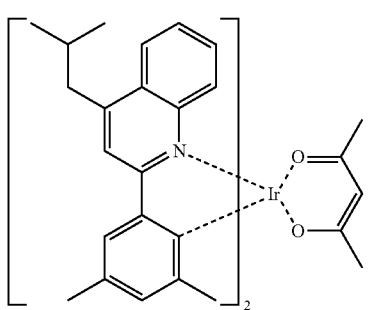

D-196
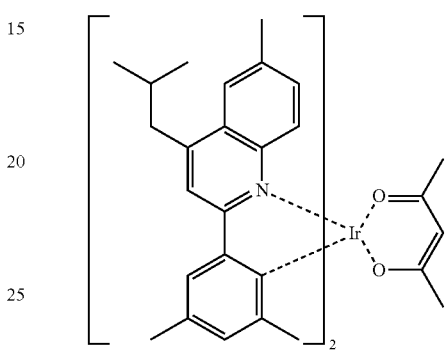

D-197
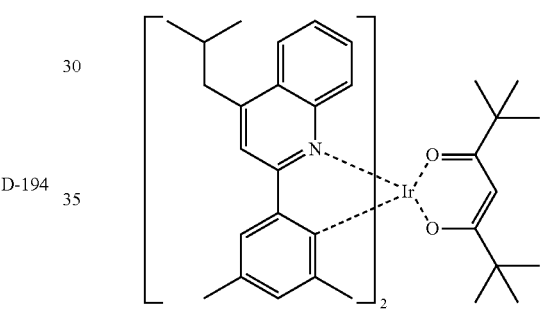

D-194
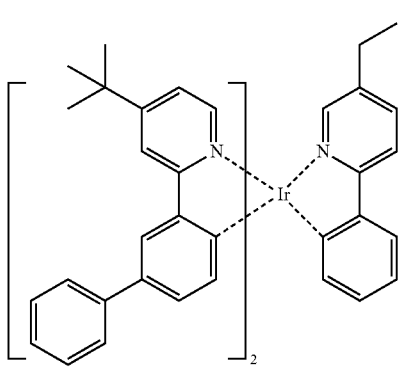

D-198
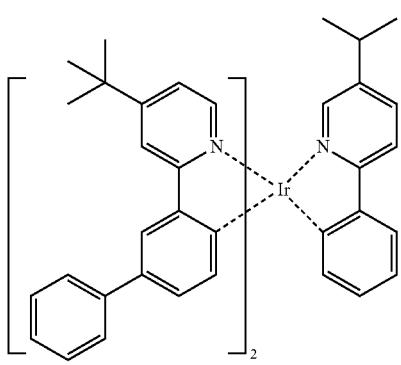

D-195
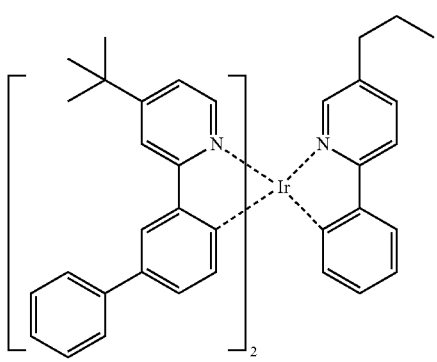

In another embodiment of the present invention, a composition for preparing an organic electroluminescent device is provided. The composition comprises the compound according to the present invention as a host material or a hole transport material.

In addition, the organic electroluminescent device according to the present invention comprises a first electrode; a second electrode; and at least one organic layer between the first and second electrodes. The organic layer comprises a light-emitting layer, and the light-emitting layer may comprise the composition for preparing the organic electroluminescent device according to the present invention.

The organic electroluminescent device according to the present invention may further comprise, in addition to the organic electroluminescent compound represented by formula 1 or 2, at least one compound selected from the group consisting of arylamine-based compounds and styrylarylamine-based compounds.

In the organic electroluminescent device according to the present invention, the organic layer may further comprise at least one metal selected from the group consisting of metals of Group 1, metals of Group 2, transition metals of the 4$^{th}$ period, transition metals of the 5$^{th}$ period, lanthanides and organic metals of d-transition elements of the Periodic Table, or at least one complex compound comprising said metal. The organic layer may further comprise a light-emitting layer and a charge generating layer.

In addition, the organic electroluminescent device according to the present invention may emit white light by further comprising at least one light-emitting layer which comprises a blue electroluminescent compound, a red electroluminescent compound or a green electroluminescent compound known in the field, besides the compound according to the present invention. Also, if necessary, a yellow or orange light-emitting layer can be comprised in the device.

According to the present invention, at least one layer (hereinafter, "a surface layer") is preferably placed on an inner surface(s) of one or both electrode(s); selected from a chalcogenide layer, a metal halide layer, and a metal oxide layer. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, said chalcogenide includes $SiO_x(1 \leq X \leq 2)$, $AlO_x(1 \leq X \leq 1.5)$, SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

In the organic electroluminescent device according to the present invention, a mixed region of an electron transport compound and reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge generating layer to prepare an electroluminescent device having two or more electroluminescent layers and emitting white light.

In order to form each layer of the organic electroluminescent device according to the present invention, dry film-forming methods such as vacuum evaporation, sputtering, plasma and ion plating methods, or wet film-forming methods such as spin coating, dip coating, and flow coating methods can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the organic electroluminescent compound, the preparation method of the compound, and the luminescent properties of the device will be explained in detail with reference to the following examples.

Example 1: Preparation of Compound A-1

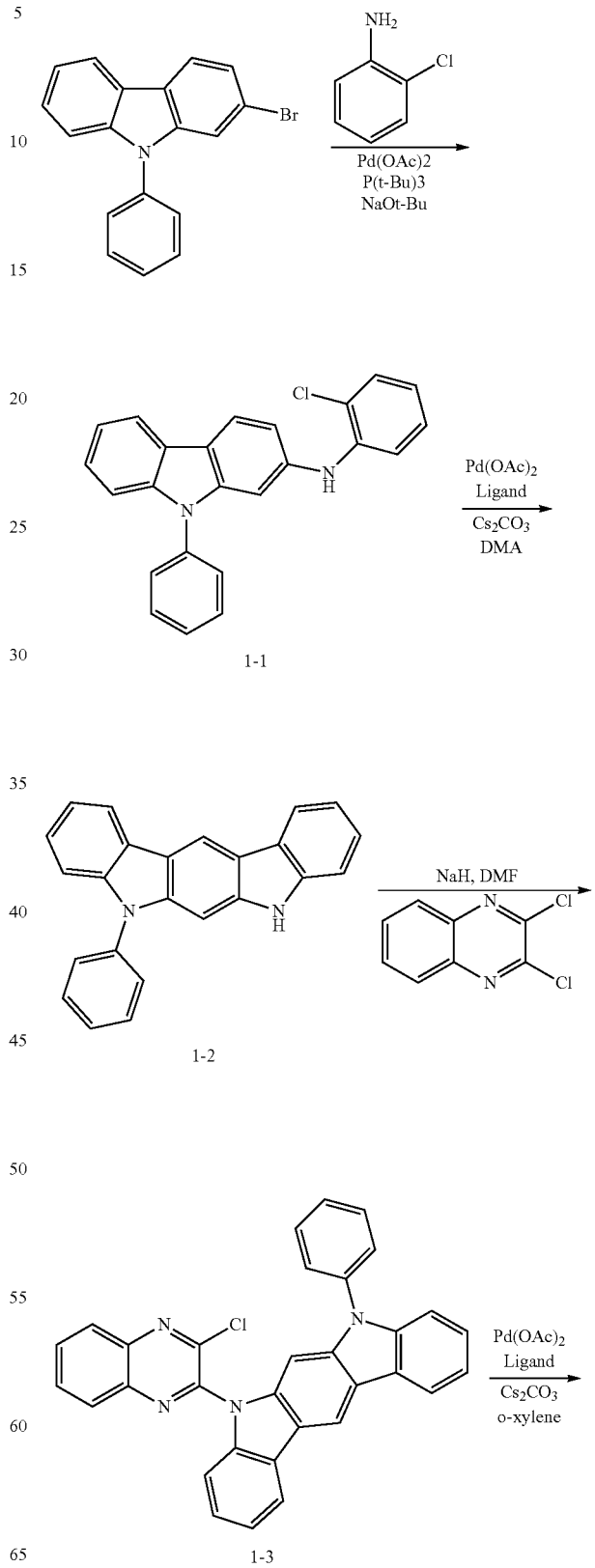

-continued

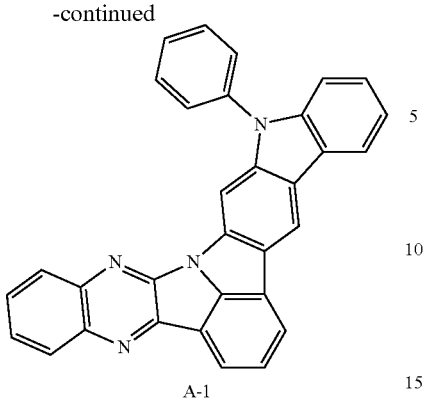

A-1

Preparation of Compound 1-1

After introducing 2-bromo-9-phenyl-9H-carbazole (56.4 g, 178 mmol), 2-chloroaniline (33.5 g, 262.6 mmol), Pd(OAc)$_2$ (3.93 g, 17.5 mmol), 50% P(t-Bu)$_3$ (17 mL, 35 mmol), NaOt-Bu (50.5 g, 525 mmol), and toluene 1000 mL in a flask, the resulting mixture was stirred. After stirring the mixture under reflux for 3 hours, the mixture was cooled to room temperature, and extracted with ethyl acetate and distilled water. The organic layer was dried with magnesium sulfate, and distilled under reduced pressure. The residue was separated by column chromatography to obtain compound 1-1 (30 g, yield: 46.5%).

Preparation of Compound 1-2

After introducing compound 1-1 (30 g, 81.3 mmol), Pd(OAc)$_2$ (1.83 g, 8.13 mmol), tricyclohexylphosphonium tetrafluoroborate (6 g, 16.26 mmol), Cs$_2$CO$_3$ (79.5 g, 244 mmol), and N,N-dimethylacetamide 400 mL in a flask, the reactant mixture was stirred under reflux for 4 hours. The mixture was cooled to room temperature, extracted with methylene chloride and distilled water, and dried with magnesium sulfate. The obtained product was distilled under reduced pressure, and the residue was separated by column chromatography to obtain compound 1-2 (16 g, yield: 59.2%).

Preparation of Compound 1-3

After introducing compound 1-2 (16 g, 48.1 mmol), sodium hydride (60%) (2.5 g, 62.5 mmol), 1,2-dichloroquinoxaline (10.5 g, 52.9 mmol), and N,N-dimethylformamide 250 mL in a flask, the reactant mixture was stirred at room temperature for 1 hour. Methanol and purified water were then added to the mixture to produce a solid. The solid was filtered, and dried under reduced pressure to obtain compound 1-3 (17 g, yield: 71.4%).

Preparation of Compound A-1

After introducing compound 1-3 (15 g, 30.3 mmol), Pd(OAc)$_2$ (1.0 g, 4.53 mmol), tricyclohexylphosphonium tetrafluoroborate (3.23 g, 9.09 mmol), Cs$_2$CO$_3$ (29.6 g, 90.9 mmol), and o-xylene 150 mL in a flask, the reactant mixture was stirred under reflux for 3 hours. The mixture was cooled to room temperature, extracted with ethyl acetate and distilled water, and dried with magnesium sulfate. The obtained product was distilled under reduced pressure, and the residue was separated by column chromatography to obtain compound A-1 (2.5 g, yield: 18%).

|     | MW    | UV     | PL     | M.P    |
| --- | ----- | ------ | ------ | ------ |
| A-1 | 458.51 | 360 nm | 493 nm | 367° C. |

Device Example 1: Production of an OLED Device Using the Organic Electroluminescent Compound According to the Present Invention An OLED device was produced using the organic electroluminescent compound according to the present invention. A transparent electrode indium tin oxide (ITO) thin film (10 Ω/sq) on a glass substrate for an organic light-emitting diode (OLED) device (Geomatec, Japan) was subjected to an ultrasonic washing with acetone, ethanol, and distilled water, sequentially, and was then stored in isopropanol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to 10$^{-6}$ torr. Thereafter, an electric current was applied to the cell to evaporate the above introduced material, thereby forming a first hole injection layer having a thickness of 80 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 10 nm on the second hole injection layer. Compound HT-2 was introduced into another cell of said vacuum vapor depositing apparatus, and was evaporated by applying an electric current to the cell, thereby forming a second hole transport layer having a thickness of 60 nm on the first hole transport layer. Thereafter, compound A-1 was introduced into one cell of the vacuum vapor depositing apparatus as a host material, and compound D-96 was introduced into another cell as a dopant. The two materials were evaporated at different rates and were deposited in a doping amount of 3 wt % (the amount of dopant) based on the total amount of the host and dopant to form a light-emitting layer having a thickness of 40 nm on the second hole transport layer. Compound ET-1 and compound EI-1 were then introduced into another two cells, evaporated at the rate of 1:1, and deposited to form an electron transport layer having a thickness of 30 nm on the light-emitting layer. Next, after depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced. All the materials used for producing the OLED device were purified by vacuum sublimation at 10$^{-6}$ torr prior to use.

HI-1

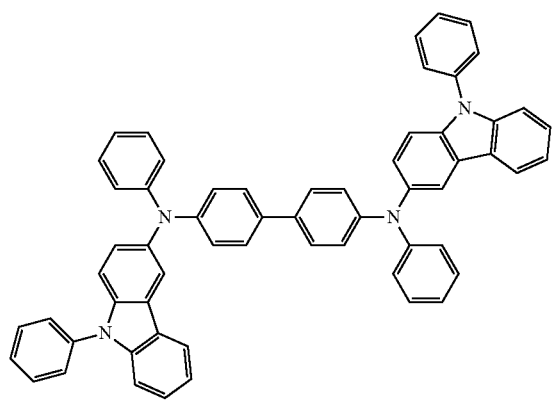

HI-2

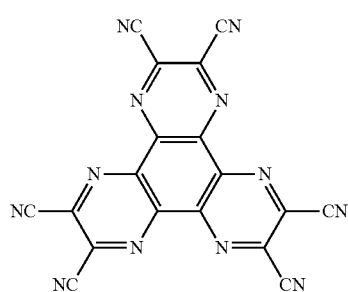

HT-1

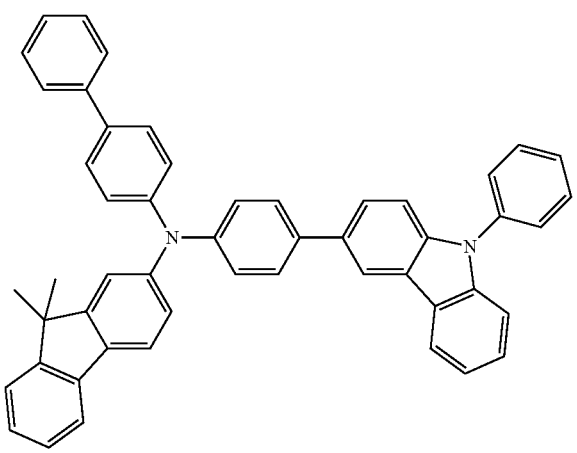

HT-2

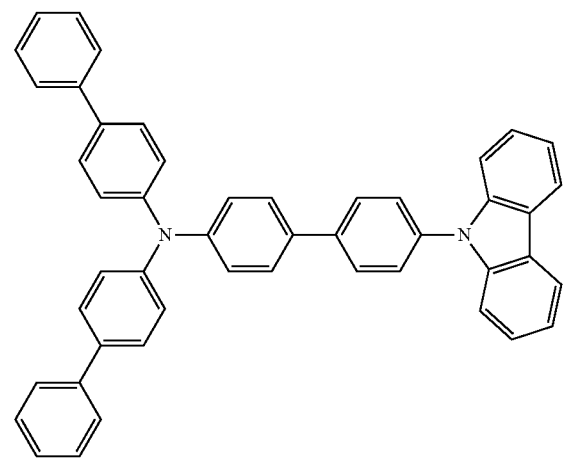

ET-1

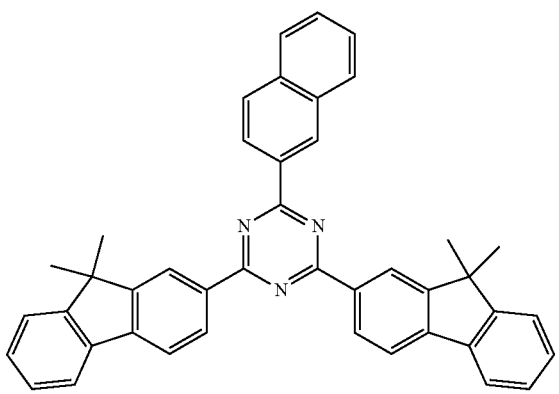

EI-1

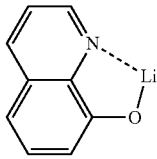

The produced OLED device showed a red emission having a luminance of 1000 cd/m² and a current density of 20.7 cd/A at 3.5 V. The time period for the luminance to decrease to 90% at 5,000 nit was 50 hours or longer.

Comparative Example 1: Production of an OLED Device Using a Conventional Organic Electroluminescent Compound An OLED device was produced in the same manner as in Device Example 1, except for using compound B-1 as below for the host as the light-emitting material.

The produced OLED device showed a red emission having a luminance of 1000 cd/m² and a current density of 1.8 cd/A at 8.1 V. The efficiency was too low to measure the lifespan.

B-1

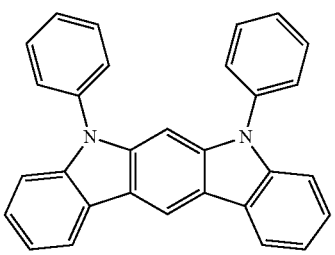

Compared to the conventional organic electroluminescent compound, the organic electroluminescent compound according to the present invention has excellent luminous characteristics, particularly, current/power efficiencies, and is capable of providing colors of high purity.

The invention claimed is:

1. A compound represented by the formula (1):

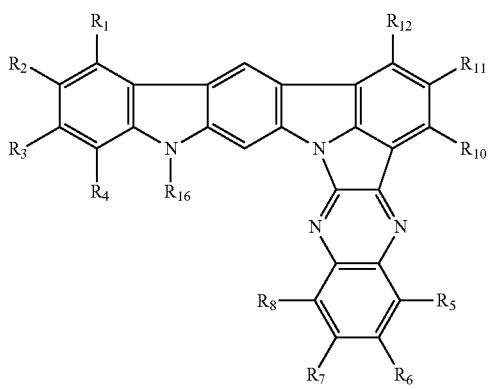

wherein:
R$_1$, R$_2$, R$_3$, R$_4$, R$_5$, R$_6$, R$_7$, R$_8$, R$_{10}$, R$_{11}$, R$_{12}$ and R$_{16}$ each independently represent hydrogen, deuterium, halogen, cyano, (C1-C30)alkyl, (C6-C30)aryl, 3- to 30-membered heteroaryl, (C3-C30)cycloalkyl, (C1-C30) alkoxy, tri(C1-C30)alkylsilyl, di(C1-C30)alkyl(C6-C30)arylsilyl, (C1-C30)alkyldi(C6-C30)arylsilyl, tri(C6-C30)arylsilyl, mono(C1-C30)alkylamino, di(C1-C30)alkylamino, mono(C6-C30)arylamino, di(C6-C30)arylamino, or (C1-C30)alkyl(C6-C30)arylamino;
where the heteroaryl contains at least one heteroatom selected from the group consisting of B, N, O, S, Si and P; and
where each (C1-C30)alkyl, (C6-C30)aryl, 3- to 30-membered heteroaryl, (C3-C30)cycloalkyl, (C1-C30) alkoxy, tri(C1-C30)alkylsilyl, di(C1-C30)alkyl(C6-C30)arylsilyl, (C1-C30)alkyldi(C6-C30)arylsilyl, tri(C6-C30)arylsilyl, mono(C1-C30)alkylamino, di(C1-C30)alkylamino, mono(C6-C30)arylamino, di(C6-C30)arylamino, or (C1-C30)alkyl(C6-C30)arylamino is optionally and independently substituted with a substituent selected from the group consisting of deuterium, halogen, cyano, carboxy, nitro, hydroxy, (C1-C30)alkyl, halo(C1-C30)alkyl, (C2-C30)alkenyl, (C2-C30)alkynyl, (C1-C30)alkoxy, (C1-C30)alkylthio, (C3-C30)cycloalkyl, (C3-C30)cycloalkenyl, 3- to 7-membered heterocycloalkyl, (C6-C30)aryloxy, (C6-C30)arylthio, 5- to 30-membered heteroaryl optionally substituted with (C6-C30)aryl, (C6-C30)aryl optionally substituted with 5- to 30-membered heteroaryl, tri(C1-C30)alkylsilyl, tri(C6-C30)arylsilyl, di(C1-C30)alkyl(C6-C30)arylsilyl, (C1-C30)alkyldi(C6-C30)arylsilyl, amino, mono(C1-C30)alkylamino, di(C1-C30)alkylamino, mono(C6-C30)arylamino, di(C6-C30)arylamino, (C1-C30)alkyl(C6-C30)arylamino, (C1-C30)alkylcarbonyl, (C1-C30)alkoxycarbonyl, (C6-C30)arylcarbonyl, di(C6-C30)arylboronyl, di(C1-C30)alkylboronyl, (C1-C30)alkyl(C6-C30)arylboronyl, (C6-C30)aryl(C1-C30)alkyl, and (C1-C30)alkyl(C6-C30)aryl.

2. The compound according to claim 1, wherein:
R$_1$, R$_2$, R$_3$, R$_4$, R$_5$, R$_6$, R$_7$, R$_8$, R$_{10}$, R$_{11}$, R$_{12}$ and R$_{16}$ each independently represent hydrogen, optionally substituted (C6-C20)aryl or optionally substituted 5- to 20-membered heteroaryl.

3. The compound according to claim 1, wherein:
R$_1$, R$_2$, R$_3$, R$_4$, R$_5$, Rb, R$_7$, R$_8$, R$_{10}$, R$_{11}$, R$_{12}$ and R$_{16}$ each independently represent hydrogen, optionally substituted (C6-C20)aryl or 5- to 20-membered heteroaryl optionally substituted with a (C6-C12)aryl.

4. The compound according to claim 1, wherein the compound is selected from the group consisting of:

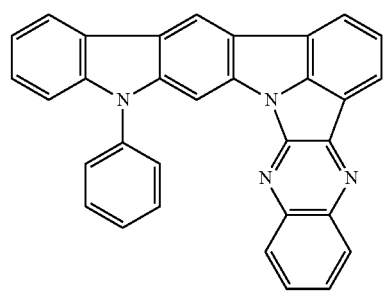

A-1

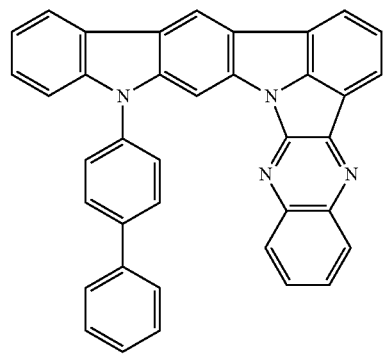

A-2

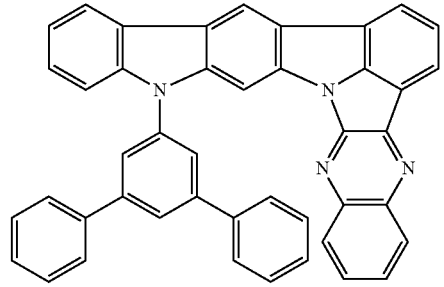

A-3

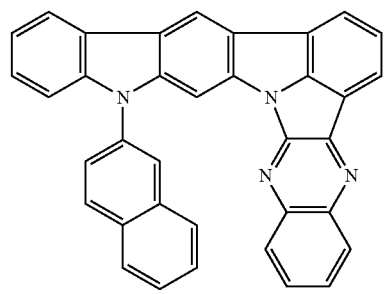

A-4

-continued
A-5
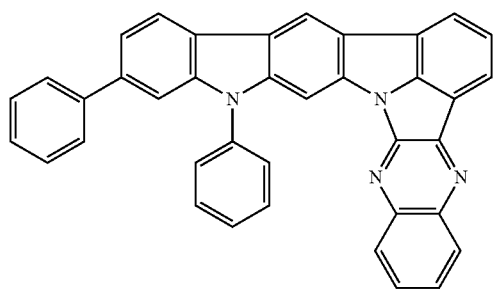
A-6
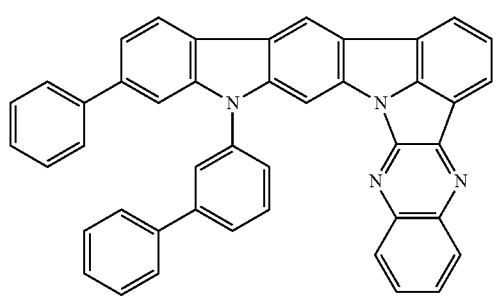
A-7
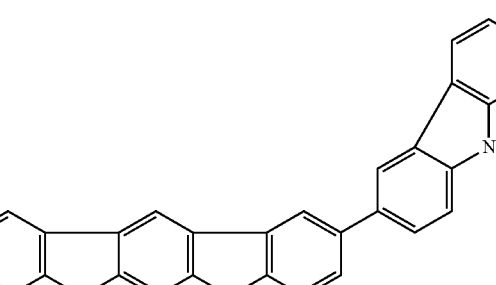
A-8
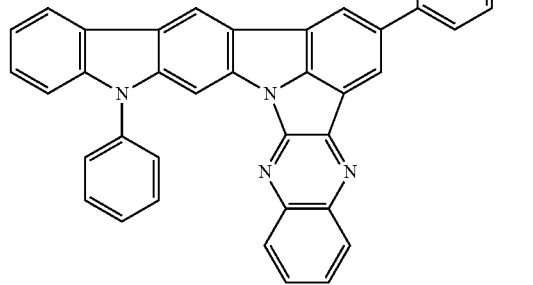
-continued
A-9
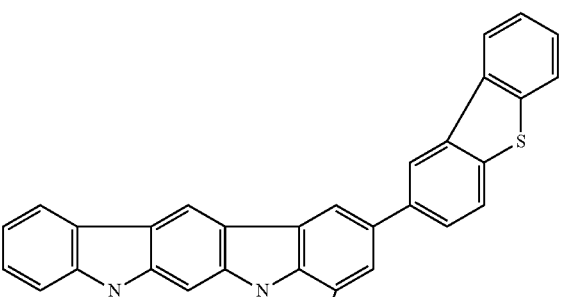
A-11
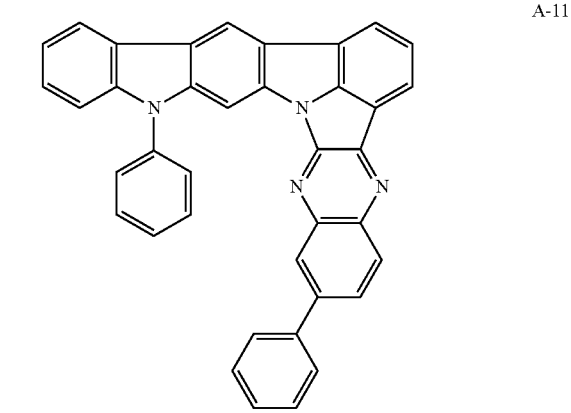
A-12
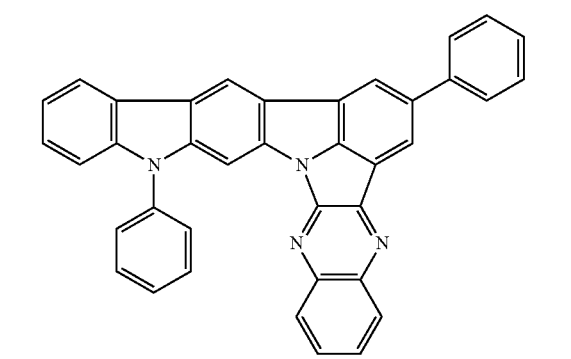
A-14
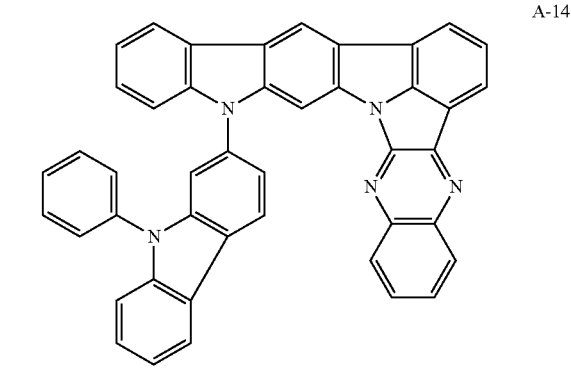

A-15
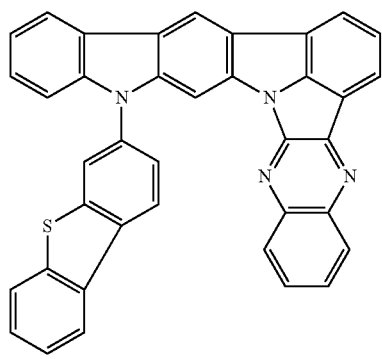
A-16
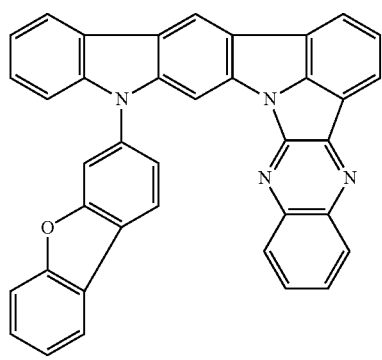
A-17
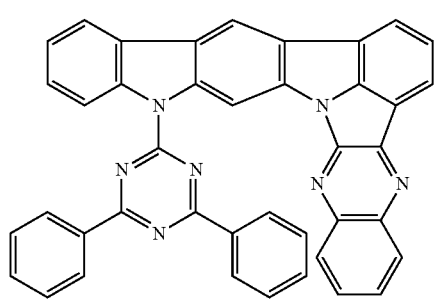
A-42
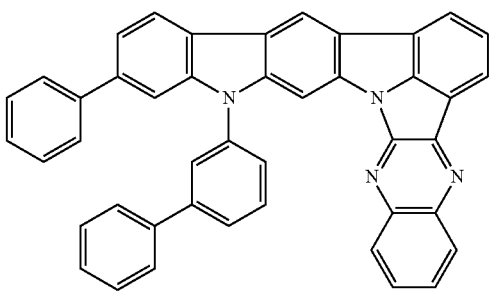
A-119
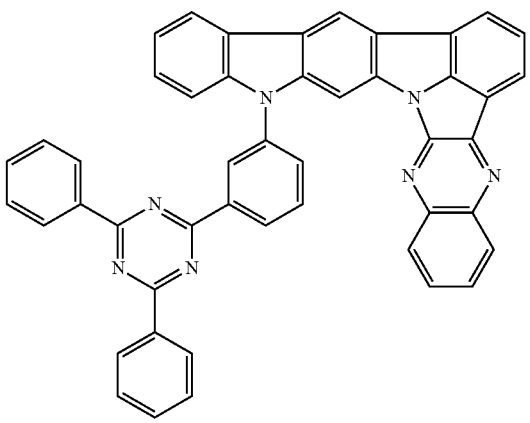
A-120
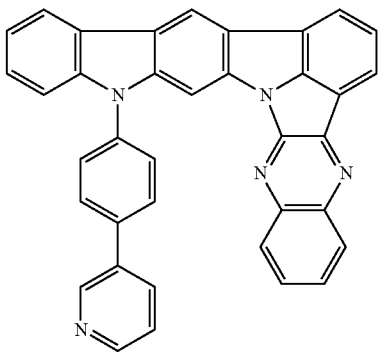

-continued
A-121
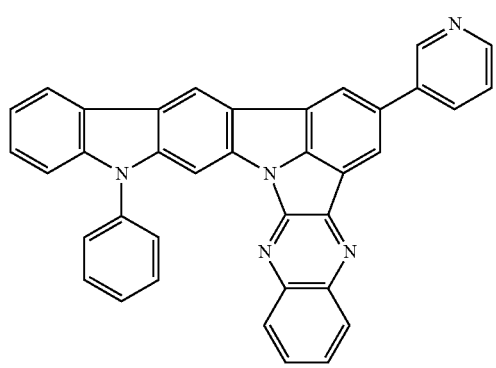
A-122
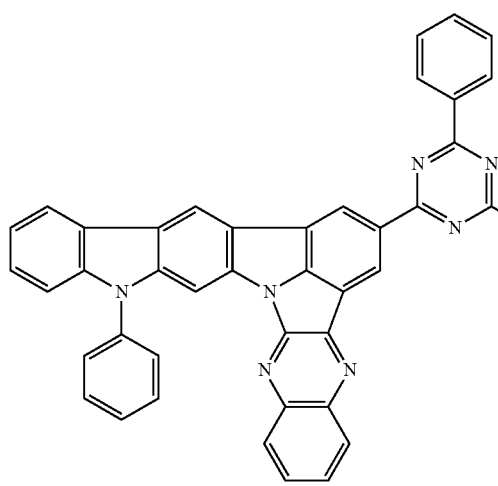
A-123
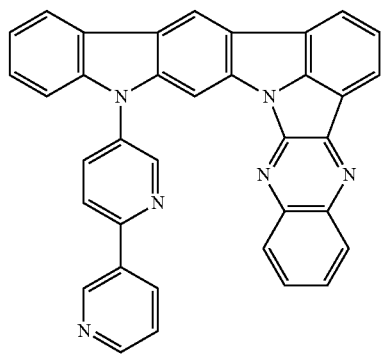
and
A-124
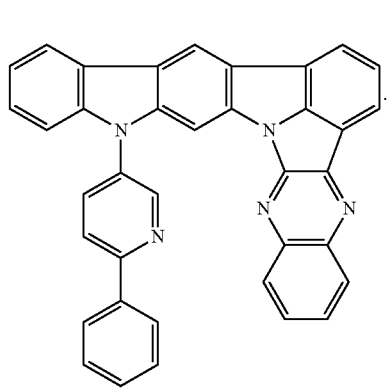
* * * * *